(12) United States Patent
Verhaert et al.

(10) Patent No.: US 10,876,113 B2
(45) Date of Patent: Dec. 29, 2020

(54) REGULATION OF TRANSLATION OF EXPRESSED GENES

(71) Applicant: Proteonic Biotechnology IP B.V, Leiden (NL)

(72) Inventors: Raymond Michael Dimphena Verhaert, Breda (NL); Pieter Victor Schut, Leiden (NL); Sharief Barends, Voorschoten (NL); Maurice Wilhelmus van der Heijden, Gouda (NL)

(*) Notice: Subject to any disclaimer, the term of this patent is extended or adjusted under 35 U.S.C. 154(b) by 382 days.

(21) Appl. No.: 15/720,428

(22) Filed: Sep. 29, 2017

(65) Prior Publication Data

US 2018/0044677 A1 Feb. 15, 2018

Related U.S. Application Data

(63) Continuation of application No. 13/877,259, filed as application No. PCT/NL2011/050664 on Sep. 30, 2011, now abandoned.

(60) Provisional application No. 61/388,668, filed on Oct. 1, 2010.

(30) Foreign Application Priority Data

Oct. 1, 2010 (EP) .................................... 10186102

(51) Int. Cl.
| | | |
|---|---|---|
| *C12N 15/113* | (2010.01) | |
| *C12P 21/00* | (2006.01) | |
| *A61K 48/00* | (2006.01) | |

(52) U.S. Cl.
CPC .......... *C12N 15/113* (2013.01); *A61K 48/005* (2013.01); *C12P 21/00* (2013.01)

(58) Field of Classification Search
None
See application file for complete search history.

(56) References Cited

U.S. PATENT DOCUMENTS 7,829,689 B2  11/2010  Van Herpen et al.

FOREIGN PATENT DOCUMENTS

WO  2009154454 A1  12/2009

OTHER PUBLICATIONS

Weterings et al., Dynamic 1-Aminocyclopropane-1-Carboxylate-Synthase and -Oxidase Transcript Accumulation Patterns During Pollen Tube Growth in Tobacco Styles, Plant Physiology, vol. 130, pp. 1190-1200, 2002.
Weterings et al., Functional Dissection of the Promoter of the Pollen-Specific Gene NTP303 Reveals a Novel Pollen-Specific, and Conserved Cis-Regulatory Element, The Plant Journal, vol. 8, pp. 55-63, 1995.
Weterings et al., Molecular Characterization of the Pollen-Specific Genomic Clone NTPg303 and In Situ Localization of Expression, Sexual Plant Reproduction, vol. 8(1), pp. 11-17, 1995.
Wittink et al., The Pollen-Specific Gene Ntp303 Encodes a 69-kDa Glycoprotein Associated with the Vegetative Membranes and the Cell Wall, Sexual Plant Reproduction, vol. 12, No. 5, pp. 276-284, 2000.
Xu et al., Isolation and Characterization of Male-Germ-Cell Transcripts in Nicotiana Tabacum, Sexual Plant Reproduction, vol. 14, pp. 339-346, 2002.
Yeakley, A complex of nuclear proteins mediates SR protein binding to a purine-rich splicing enhancer, Proc. Natl. Acad. Sci. USA (1996), vol. 93, pp. 7582-7587.
Zuker, Mfold web server for nucleic acid folding and hybridization prediction, Nuc. Acid. Res. 2003, 31, pp. 3406-3415.
International Search Report dated May 20, 2003 for PCT Application No. PCT/NL2002/000638.
Written Opinion dated Jul. 9, 2003 for PCT Application No. PCT/NL2002/000638.
International Preliminary Examination Report dated Dec. 29, 2003 for PCT Application No. PCT/NL2002/000638.
Preliminary Amendment filed Apr. 5, 2004 for U.S. Appl. No. 10/491,749.
Restriction Requirement dated Sep. 8, 2006 for U.S. Appl. No. 10/491,749.
Response to Restriction Requirement filed Dec. 8, 2006 for U.S. Appl. No. 10/491,749.
Restriction Requirement dated Mar. 7, 2007 for U.S. Appl. No. 10/491,749.
Response to Restriction Requirement filed Jun. 7, 2007 for U.S. Appl. No. 10/491,749.
Non-Final Office Action dated Sep. 18, 2007 for U.S. Appl. No. 10/491,749.
Response to Non-Final Office Action filed Mar. 18, 2008 for U.S. Appl. No. 10/491,749.
Response to Non-Final Office Action filed Apr. 7, 2008 for U.S. Appl. No. 10/491,749.
Final Office Action dated Jul. 9, 2008 for U.S. Appl. No. 10/491,749.
Response to Final Office Action filed Jan. 8, 2009 for U.S. Appl. No. 10/491,749.
Supplemental Response to Final Office Action filed Jan. 23, 2009 for U.S. Appl. No. 10/491,749.
Notice of Allowance dated Oct. 23, 2009 for U.S. Appl. No. 10/491,749.
Notice of Allowance dated Feb. 22, 2010 for U.S. Appl. No. 10/491,749.
Notice of Withdrawal from Issue issued Jul. 29, 2010 for U.S. Appl. No. 10/491,749.

(Continued)

*Primary Examiner* — James D Schultz

(57) ABSTRACT

The present invention describes mRNA usage improving and/or translation-enhancing nucleic acid sequences, nucleic acid constructs comprising such sequences, and host cells comprising such nucleic acid constructs. The invention further pertains to a method for expressing a protein of interest in a cell or organismusing such nucleic acid sequences, as well as their uses for increasing integration of such nucleic acid construct into a genome, for enhancing mRNA usage and/or translation of a recombinantly expressed polypeptide, and for increasing the number of transformants upon transformation of a cell with such nucleic acid construct.

18 Claims, 3 Drawing Sheets

Figure 1:
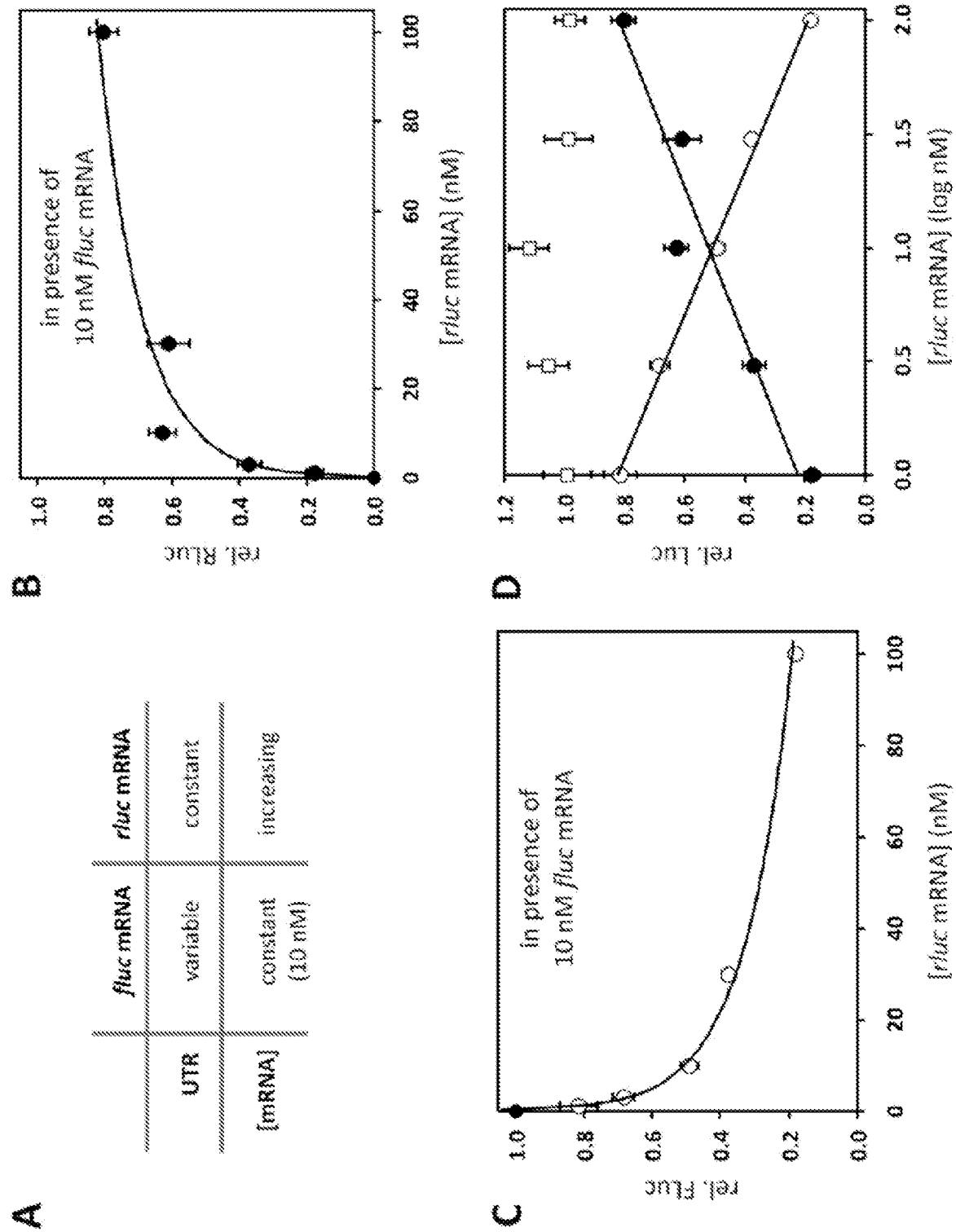

Specification includes a Sequence Listing.

(56) References Cited

OTHER PUBLICATIONS

Notice of Allowance dated Sep. 28, 2010 for U.S. Appl. No. 10/491,749.
Communication from the Examining Division dated Aug. 28, 2006 for European Application No. EP2002763110.
Response to Communication from the Examining Division filed Dec. 12, 2006 for European Application No. EP2002763110.
Communication from the Examining Division dated Apr. 20, 2007 for European Application No. EP2002763110.
Response to Communication from the Examining Division filed Aug. 2, 2007 for European Application No. EP2002763110.
Summons to Attend Oral Proceedings issued Apr. 8, 2008 for European Application No. EP2002763110.
Response to Summons filed Jun. 18, 2008 for European Application No. EP2002763110.
Communication from the Examining Division dated Jul. 3, 2008 for European Application No. EP2002763110.
Response to Communication from the Examining Division filed Dec. 16, 2008 for European Application No. EP2002763110.
Communication from the Examining Division dated Jan. 12, 2009 for European Application No. EP2002763110.
Response to Communication from the Examining Division filed Feb. 16, 2009 for European Application No. EP2002763110.
Summons to Attend Oral Proceedings issued Aug. 18, 2009 for European Application No. EP2002763110.
Response to Summons filed Sep. 28, 2009 for European Application No. EP2002763110.
Response to Summons filed Oct. 8, 2009 for European Application No. EP2002763110.
Record of Consultation issued Oct. 9, 2009 for European Application No. EP2002763110.
Intent to Grant Letter dated Nov. 26, 2009 for European Application No. EP2002763110.
Request for Further Processing and Amended Claims filed Jul. 16, 2010 for European Application No. EP2002763110.
Communication from the Examining Division dated Oct. 22, 2010 for European Application No. EP2002763110.
International Search Report dated Apr. 5, 2012 for PCT Application No. PCT/NL2011/050664.
Written Opinion dated Apr. 1, 2013 for PCT Application No. PCT/NL2011/050664.
Bailey-Serres, Selective Translation of Cytoplasmic mRNAs in Plants, Trends in Plant Science, vol. 4, pp. 142-148, 1999.
Bate et al., Maturation-Specific Translational Enhancement Mediated by the 5'-UTR of a Late Pollen Transcript, Plant Journal, vol. 10 No. 4, pp. 613-623, 1996.
Burd et al., Conserved Structures and Diversity of Functions of RNA-Binding Proteins, Science, vol. 265, pp. 615-621, Jul. 29, 1994.
Chang et al., Characterization and Translational Regulation of the Arginine Decarboxylase Gene in Carnation (*Dianthus caryophyllus* L.), Plant Journal, vol. 24, No. 1, pp. 45-56, Oct. 2000.
Chappell, Ribosomal tethering and clustering as mechanisms for translation initiation (2006) 103, pp. 18077-18082.
Chen et al., RNA secondary structure and compensatory evolution, Genes Genet. Syst. (1999) 74, pp. 271-286.
Costello et al., Global mRNA selection mechanisms for translation initiation, Genome Biology (2015) 16, pp. 1-21.
De Breyne et al., Direct functional interaction of initiation factor eIF4G with type 1 internal ribosomal entry sites, PNAS (2009) 106, pp. 9197-9202.
Delbecq et al., Functional Analysis of the Leader Peptide of the Yeast Gene CPA1 and Heterologous Regulation by Other Fungal Peptides, Current Genetics, vol. 38, No. 3, pp. 105-112, Oct. 2000.
Edwards et al., Cell-Specific Gene Expression in Plants, Annu. Rev. Genet., vol. 24, pp. 275-303, 1990.
Flinn et al., Potato expressed sequence tag generation and analysis using standard and unique cDNA libraries, Plant Molecular Biology 2005, 59(3), pp. 407-433.

Gallie, Identification of the motifs within the tobacco mosaic virus 5'-leader responsible for enhancing translation, Nucleic Acids Research (1992), vol. 20(17), pp. 4631-4638.
Hamilton et al., Dissection of a Pollen-Specific Promoter from Maize by Transient Transformation Assays, Plant Molecular Biology, vol. 18, pp. 211-218, 1992.
Herwig et al., Construction of a 'unigene' cDNA clone set by oligonucleotide fingerprinting allows access to 25000 potential sugar beet genes, Plant Journal 2002, 32(5), pp. 845-857.
Hofacker et al., Fast Folding and Comparison of RNA Secondary Structures, Chemical Monthly, vol. 125, pp. 167-188, 1994.
Honys et al., Translational Regulation of Pollen Tube-Wall Specific Glycoprotein P69, Plant Physiology and Biochemistry, vol. 38, Supplement, p. 63, Aug. 2000.
Honys et al., The Translationally Repressed Pollen-Specific ntp303 mRNA is Stored in Non-Polysomal mRNPs During Pollen Maturation, Sexual Plant Reproduction, vol. 13, No. 3, pp. 135-144, 2000.
Hulzink et al., The 5'-Untranslated Region of the ntp303 Gene Strongly Enhances Translation During Pollen Tube Growth, But Not During Pollen Maturation, Plant Physiology (2002), vol. 129, pp. 342-353.
Jackson et al., The mechanism of eukaryotic translation initiation and principles of its regulation, Molecular Cell Biology (2010) 10, pp. 113-127.
Jang et al., Cap-dependent translation is mediated by 'RNA looping' rather than 'ribosome scanning', RNA Biology (2016) 13, pp. 1-15.
Jang et al., A Segment of the 5' Nontranslated Region of Encephalomyocarditis Virus RNA Directs Internal Entry of Ribosomes during In Vitro Translation, Journal of Virology (1988), pp. 2636-2643.
Jefferson et al., GUS Fusions: β-glucuronidase as a Sensitive and Versatile Gene Fusion Marker in Higher Plants, The EMBO Journal, vol. 6, pp. 3901-3907, 1987.
Karthikeyan et al., Promoter deletion analysis elucidates the role of cis elements and 5'UTR intron in spatiotemporal regulation of AtPht1;4 expression in Arabidopsis, Physiologia Plantarum 2009, 136(1), pp. 10-18.
Kisselev et al., Translational termination comes of age, Trends in Biochem. Sci. (2000) 25, pp. 561-566.
Kozak, Circumstances and Mechanisms of Inhibition of Translation by Secondary Structure in Eucaryotic mRNAs, Molecular and Cellular Biology (1989), pp. 5134-5142.
Kozak, Initiation of Translation in Prokaryotes and Eukaryotes, Gene, Elsevier Biomedical Press, vol. 234, No. 2, pp. 187-208, Jul. 8, 1999.
Ladner et al., Structure of yeast phenylalanine transfer RNA at 2.5 Å resolution, Proc. Nat. Acad. Sci. USA (1975) 72, pp. 4414-4418.
Lu et al., Gene expression enhancement mediated by the 5' UTR intron of the rice rubi3 gene varied remarkably among tissues in transgenic rice plants, Molecular Genetics and Genomics (2008), vol. 279, pp. 563-572.
Mathews et al., Expanded Sequence Dependence of Thermodynamic Parameters Improves Prediction of RNA Secondary Structure, J. Mol. Biol. (1999) 288, pp. 911-940.
Murray et al., Codon Usage in Plant Genes, Nucleic Acids Research, vol. 17, No. 2, pp. 477-498, 1989.
Nottrott et al., Functional Interaction of a novel 15.5kD [U4/U6•U5] tri-snRNP protein with the 5' stem-loop of U4 snRNA, Eur. Mol. Bio. Org. Journal (1999) 18, pp. 6119-6133.
Ow et al., Transient and Stable Expression of the Firefly Luciferase Gene in Plant Cells and Transgenic Plants, Science, vol. 234, pp. 856-859, 1986.
Paek et al., Translation initiation mediated by RNA looping, PNAS (2105) 112, pp. 1041-1046.
Pesole et al., Structural and Functional Features of Eukaryotic mRNA Untranslated Regions, Gene, vol. 276, pp. 73-81, 2001.
Phillips et al., Identification of a stem-loop structure important for polyadenylation at the murine IgM secretory poly(A) site, Nuc. Acid. Res. (1999) 27, pp. 429-438.

(56) References Cited

OTHER PUBLICATIONS

Pratt et al., Sorghum Expressed Sequence Tags identify Signature Genes for Drought, Pathogenesis, and Skotomorphogenesis from a Milestone Set of 16,801 Unique Transcripts, Plant Physiology 2005, 139(2), pp. 869-884.

Read et al., Stimulation of Growth of Cultured Nicotiana tabacum W38 Pollen Tubes by Poly(ethylene glycol) and Cu(II) Salts, Protoplasma, vol. 177, pp. 1-14, 1993.

Rose, Intron-mediated regulation of gene expression, Current Topics in Microbiology and Immunology (2008), vol. 326, pp. 277-290.

Schrauwen et al., Mass Culture of Pollen Tubes, Acta Botanica Neerlandica, vol. 16(5), pp. 177-179, Nov. 1967.

Smith et al., Sno Storm in the Nucleolus: New Roles for Myriad Small RNPs, Cell (1997) 89, pp. 669-672.

Storchova et al., A Nicotiana Tabacum mRNA Encoding a 69-kDa Glycoprotein Occurring Abundantly in Pollen Tubes is Transcribed but not Translated During Pollen Development in the Anthers, Planta, vol. 192, No. 3, pp. 441-445, 1994.

Tam, Identification and characterization of human BIC, a gene on chromosome 21 that encodes a noncoding RNA, Gene (2001) 274, pp. 157-167.

Topfer et al., A Set of Plant Expression Vectors for Transcriptional and Translational Fusions, Nucleic Acids Research, vol. 15, No. 14, p. 5890, 1987.

Tupy et al., Production of Fertile Tobacco Pollen from Microspores in Suspension Culture and its Storage for In Situ Pollination, Sexual Plant Reproduction, vol. 4, pp. 284-287, 1991.

Twell et al., Isolation and Expression of an Anther-Specific Gene from Tomato, Molecular and General Genetics MGG, vol. 217, Issue 2-3, pp. 240-245 (EMBL Database, Abstract, Accession No. X15855), Jun. 1989.

Van Herpen et al., In-Vitro Culture of Tobacco Pollen: Gene Expression and Protein Synthesis, Sexual Plant Reproduction, vol. 5, pp. 304-309, 1992.

Wade et al., A cDNA microarray from the telecephalon of juvenile male and female zebra finches, Journal of Neuroscience Methods 138 (2004), pp. 199-206.

Wade et al., Erratum to "A cDNA microarray from the telecephalon of juvenile male and female zebra finches," Journal of Neuroscience Methods 2005, 142(2), p. 327.

Wang et al., Role of mRNA Secondary Structure in Translation Repression of the Maize Transcriptional Activator Lc1, 2, Plant Physiology, vol. 125, No. 3, pp. 1380-1387, Mar. 2001.

Weterings et al., Characterization of a Pollen-Specific cDNA Clone from Nicotiana Tabacum Expressed During Microgametogenesis and Germination, Plant Molecular Biology, vol. 18, pp. 1101-1111, 1992.

REGULATION OF TRANSLATION OF EXPRESSED GENES

CROSS REFERENCE TO RELATED APPLICATIONS

This application is a continuation of U.S. patent application Ser. No. 13/877,259 filed on Apr. 22, 2013, which is a national stage application under 35 U.S.C. § 371 of International Application No. PCT/NL2011/050664, filed on Sep. 30, 2011, which claims the benefit of U.S. Patent Application No. 61/388,668, filed on Oct. 1, 2010, all of which are hereby incorporated herein by reference in their entirety.

FIELD OF THE INVENTION

The invention relates to nucleic acid sequences that enhance mRNA usage and/or translation in a host cell and their use for regulating the expression of a protein in such host cell.

BACKGROUND OF THE INVENTION

The translation process in eukaryotes is a complex series of steps that involve a wide array of protein translation factors. These factors function in conjunction with the ribosome and tRNAs to decode an mRNA, thereby generating the encoded polypeptide chain. The translation process can be divided into three distinct stages: (i) initiation: the assembly of the ribosomal subunits at the initiation (AUG) codon of an mRNA; (ii) elongation: tRNA-dependend decoding of the mRNA to form a polypeptide chain; (iii) termination: a stop codon (UAA, UAG or UGA) signals the release of the polypeptide chain from the ribosome and subsequently the ribosomal subunits dissociate from the mRNA. Each of these stages requires a specific class of translation factors: eukaryotic initiation, elongation and termination factors (eIF, eEF and eRF, respectively). The same principle is applicable to prokaryotes.

Translation initiation is an important step in both global and mRNA-specific gene regulation and therefore constitutes a target for translational control. Global regulation of protein synthesis is generally achieved by the modification of eukaryotic initiation factors (eIFs), several of which are phosphoproteins, e.g., eIF4E and eIF2. Translational control of individual mRNAs often depends upon the structural properties of the transcript itself. These may include properties in the 5' untranslated region of the mRNA that can affect initiation either directly, for example by impeding 40S subunit binding or scanning, or indirectly by acting as receptors for a regulating RNA-binding protein. The role of that sequence in the control of translation has been reviewed by Day and Tuite (1998, J. of Endocrinology 157; 361-371).

Structural properties of the 5' end of an mRNA transcript that may affect translation initiation of that transcript include, but are not limited to the presence of an m7G cap structure, the primary sequence context of the initiation codon, the presence of upstream AUGs, the stability and position of secondary structures, and/or the length of the 5' UTR.

The RNA secondary structure positioned between the cap structure and the AUG codon may typically be inhibitory to translation initiation (Kozak 1989, Molecular and Cellular Biology 9:5134-5142). For example, the inhibition can be by steric hindrance preventing the binding of the 43S preinitiation complex to the cap structure. In contrast, increasing the length of the 5' sequence may lead to a proportional increase in translational efficiency (Kozak 1991, Gene Expression 1:117-125), which may simply be due to increased loading of the 40S subunits on the longer 5' sequences. In addition, mRNA secondary structures can also have a regulating role. For example, RNA structural elements can provide sites for the binding of regulating proteins and RNA molecules and, by forming a stable structure, they typically impede binding or scanning of the 40S ribosomal subunit (Goossen et al. 1990, Goossen & Hentze 1992).

It has previously been demonstrated that cis-acting elements in the npt303 mRNA are responsible for this mechanism of translational regulation (WO03/031613). Moreover, expression of proteins other than NPT303, such as heterologous proteins, could be regulated using these cis-acting elements.

However, it was found that the 5'-UTR of NPT303 may have a limiting effect on transcription. There is still a need in the art for alternative and preferably improved methods for regulating the expression of a protein of interest in host cells.

SUMMARY OF THE INVENTION

The present invention relates to a method for expressing a protein of interest in a cell or organism, said organism not being a human, said method comprising the steps of: a) providing a nucleic acid construct comprising: i) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence; ii) a first nucleotide sequence that comprises: a TC-rich nucleotide sequence comprising at least 8 consecutive C or T nucleotides, at least 3 A-rich nucleotide sequences comprising at least 5 consecutive A nucleotides, and a GT-rich nucleotide sequence comprising at least 10 nucleotides, at least 80% of which are G or T nucleotides, said first nucleotide sequence not comprising a GAA repeat nucleotide sequence; iii) a first nucleotide sequence that comprises: a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, said first nucleotide sequence not comprising a GAA repeat nucleotide sequence; iv) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence; or v) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, wherein said GAA repeat nucleotide sequence is located 3' of any one or more of said TC-rich nucleotide sequence, A-rich nucleotide sequences, and/or GT-rich nucleotide sequence; operably linked to a second nucleotide sequence encoding a protein or polypeptide of interest, and further operably linked to a promoter, b) contacting a cell with said nucleic acid construct to obtain a transformed cell, and c) allowing said transformed cell to express the protein or polypeptide of interest, for example, by subjecting said transformed cell to conditions leading to expression of the protein or polypeptide of interest, and optionally recovering said protein or polypeptide.

The cell may be selected from the group consisting of an animal, such as mammalian, including human, or insect, cell, plant cell, fungal cell, and yeast cell.

In another aspect, the invention is concerned with a method for expressing a protein of interest in an organism, said organism not being a human, comprising the steps of: a) providing a nucleic acid construct comprising: i) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence; ii) a first nucleotide sequence that comprises: a TC-rich nucleotide sequence comprising at least 8 consecutive C or T nucleotides, at least 3 A-rich nucleotide sequences comprising at least 5 consecutive A nucleotides, and a GT-rich nucleotide sequence comprising at least 10 nucleotides, at least 80% of which are G or T nucleotides, said first nucleotide sequence not comprising a GAA repeat nucleotide sequence; iii) a first nucleotide sequence that comprises: a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, said first nucleotide sequence not comprising a GAA repeat nucleotide sequence; iv) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence; or v) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, wherein said GAA repeat nucleotide sequence is located 3' of any one or more of said TC-rich nucleotide sequence, A-rich nucleotide sequences, and/or GT-rich nucleotide sequence; operably linked to a second nucleotide sequence encoding a protein or polypeptide of interest and further operably linked to a promoter, b) contacting a target cell and/or target tissue of an organism, said organism not being a human, with said nucleic acid construct to obtain a transformed target cell and/or transformed target tissue, and c) optionally, allowing said transformed target cell to develop into a transformed organism, and d) allowing said transformed organism to express the protein or polypeptide of interest, for example, by subjecting said transformed cell to conditions leading to expression of the protein or polypeptide of interest, and optionally recovering said protein or polypeptide.

The organism may be selected from the group consisting of a non-human animal, an insect, a fungus, a yeast, and a plant.

The invention also pertains to a method for expressing a protein of interest in a yeast or yeast cell, said method comprising the steps of: a) providing a nucleic acid construct comprising: i) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence; ii) a first nucleotide sequence that comprises: a TC-rich nucleotide sequence comprising at least 8 consecutive C or T nucleotides, at least 3 A-rich nucleotide sequences comprising at least 5 consecutive A nucleotides, and a GT-rich nucleotide sequence comprising at least 10 nucleotides, at least 80% of which are G or T nucleotides, said first nucleotide sequence not comprising a GAA repeat nucleotide sequence; or iii) a first nucleotide sequence that comprises: a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, said first nucleotide sequence not comprising a GAA repeat nucleotide sequence; operably linked to a second nucleotide sequence encoding a protein or polypeptide of interest, and further operably linked to a promoter, b) contacting a cell with said nucleic acid construct to obtain a transformed cell, and c) allowing said transformed cell to express the protein or polypeptide of interest, for example, by subjecting said transformed cell to conditions leading to expression of the protein or polypeptide of interest, and optionally recovering said protein or polypeptide.

Also, the invention is concerned with a method for expressing a protein of interest in a fungus or fungal cell, said method comprising the steps of: a) providing a nucleic acid construct comprising: i) a first nucleotide sequence that comprises: a TC-rich nucleotide sequence comprising at least 8 consecutive C or T nucleotides, at least 3 A-rich nucleotide sequences comprising at least 5 consecutive A nucleotides, and a GT-rich nucleotide sequence comprising at least 10 nucleotides, at least 80% of which are G or T nucleotides, said first nucleotide sequence not comprising a GAA repeat nucleotide sequence, ii) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence, or iii) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, wherein said GAA repeat nucleotide sequence is located 3' of any one or more of said TC-rich nucleotide sequence, A-rich nucleotide sequences, and/or GT-rich nucleotide sequence; operably linked to a second nucleotide sequence encoding a protein or polypeptide of interest, and further operably linked to a promoter, b) contacting a cell with said nucleic acid construct to obtain a transformed cell, and c) allowing said transformed cell to express the protein or polypeptide of interest, for example, by subjecting said transformed cell to conditions leading to expression of the protein or polypeptide of interest, and optionally recovering said protein or polypeptide.

The invention further deals with a method for expressing a protein of interest in a non-human animal or an animal cell, said method comprising the steps of: a) providing a nucleic acid construct comprising: i) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence; ii) a first nucleotide sequence that comprises: a TC-rich nucleotide sequence comprising at least 8 consecutive C or T nucleotides, at least 3 A-rich nucleotide sequences comprising at least 5 consecutive A nucleotides, and a GT-rich nucleotide sequence comprising at least 10 nucleotides, at least 80% of which are G or T nucleotides, said first nucleotide sequence not comprising a GAA repeat nucleotide sequence; or iii) a first nucleotide sequence that comprises: a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, said first nucleotide sequence not comprising a GAA repeat nucleotide sequence; operably linked to a second nucleotide sequence encoding a protein or polypeptide of interest, and further operably linked to a promoter, b) contacting a cell with said nucleic acid construct to obtain a transformed cell, and c) allowing said transformed cell to express the protein or polypeptide of interest, for example, by subjecting said transformed cell to conditions leading to expression of the protein or polypeptide of interest, and optionally recovering said protein or polypeptide.

In addition, the invention is concerned with a method for expressing a protein of interest in a plant or plant cell, said method comprising the steps of: a) providing a nucleic acid construct comprising: i) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence; or ii) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, wherein said GAA repeat nucleotide sequence is located 3' of any one or more of said TC-rich nucleotide sequence, A-rich nucleotide sequences, and/or GT-rich nucleotide sequence; operably linked to a second nucleotide sequence encoding a protein or polypeptide of interest, and further operably linked to a promoter, b) contacting a cell with said nucleic acid construct to obtain a transformed cell, and c) allowing said transformed cell to express the protein or polypeptide of interest, for example, by subjecting said transformed cell to conditions leading to expression of the protein or polypeptide of interest, and optionally recovering said protein or polypeptide.

In an embodiment, the second nucleotide sequence encodes a protein or polypeptide that is heterologous to the cell or organism. Alternatively, the second nucleotide sequence may encode a protein or polypeptide that is endogenous to the cell or organism. The second nucleotide sequence may encode a newly designed or created protein, for example, derived from phage display libraries.

In an embodiment, the GAA repeat nucleotide sequence comprises at least 3 GAA repeats. The GAA repeat nucleotide sequence may comprise an imperfect GAA repeat. The GAA repeat nucleotide sequence may have at least about 50% sequence identity or at least 50% sequence identity, or at least 60% sequence identity, or at least 70% sequence identity, or at least 80% sequence identity, or at least 90% sequence identity or 100% sequence identity with nucleotides 14-50 of SEQ ID NO: 1. The imperfect GAA repeat may comprise the nucleotide sequence $(GAA)_3ATAA(GAA)_8$.

In an embodiment, the TC-rich nucleotide sequence has at least about 70% sequence identity or at least 70% sequence identity, or at least 80% sequence identity, or at least 90% sequence identity or 100% sequence identity with nucleotides 54-68 of SEQ ID NO:1.

In an embodiment, the A-rich nucleotide sequences have at least about 80% sequence identity, or at least 80% sequence identity, or at least 90% sequence identity or 100% sequence identity with any one of nucleotides 77-87, nucleotides 93-105, nucleotides 111-121, nucleotides 126-132, or nucleotides 152-169 of SEQ ID NO:1, respectively.

In an embodiment, the GT-rich nucleotide sequence has at least about 70% sequence identity or at least 70% sequence identity, or at least 80% sequence identity, or at least 90% sequence identity or 100% sequence identity with nucleotides 133-148 of SEQ ID NO:1.

The intron sequence may comprise the splice site GT at the 5' end of the nucleotide sequence, and the splice site AG at the 3' end of the nucleotide sequence, which splice site AG is preceded by a TC-rich nucleotide sequence, optionally separated from splice site AG by about 1-50 nucleotides or by 1-50 nucleotides. The intron sequence may further comprise a branch site comprising the sequence (C/T)T(A/G)A (C/T), at the 5' side of the TC-rich nucleotide sequence. The branch site may have the nucleotide sequence CTGAC. The intron sequence may comprises a nucleotide sequence having about 80% sequence identity, or 80% sequence identity, or at least 90% sequence identity or 100% sequence identity with nucleotides 171-277 of SEQ ID NO:2, nucleotides 171-274 of SEQ ID NO:7, nucleotides 133-210 of SEQ ID NO:8, nucleotides 134-211 of SEQ ID NO:9, nucleotides 134-226 of SEQ ID NO:10, nucleotides 134-226 of SEQ ID NO:11, nucleotides 133-225 of SEQ ID NO:12, nucleotides 134-226 of SEQ ID NO:13, nucleotides 146-257 of SEQ ID NO:14, or nucleotides 147-223 of SEQ ID NO:15.

In an embodiment, the nucleic acid construct comprises a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, in which first nucleotide sequence the order of the nucleotide sequences is the following: 5' GAA repeat nucleotide sequence-TC-rich nucleotide sequence-A-rich nucleotide sequence-A-rich nucleotide sequence-A-rich nucleotide sequence-A-rich nucleotide sequence-GT-rich nucleotide sequence-A-rich nucleotide sequence-intron sequence 3', which nucleotide sequences may be separated from each other by 1-50 nucleotides.

In an aspect, the nucleic acid construct comprises a first nucleotide sequence that comprises: a TC-rich nucleotide sequence comprising at least 8 consecutive C or T nucleotides, at least 3 A-rich nucleotide sequences comprising at least 5 consecutive A nucleotides, and a GT-rich nucleotide sequence comprising at least 10 nucleotides, at least 80% of which are G or T nucleotides, said first nucleotide sequence lacking a GAA repeat nucleotide sequence. The first nucleotide sequence may have at least about 50% nucleotide sequence identity, or at least 50% nucleotide sequence identity, or at least 60% sequence identity, or at least 70% sequence identity, or at least 80% sequence identity, or at least 90% sequence identity or 100% sequence identity with the nucleotide sequence of SEQ ID No. 3, 16, 17, 18, 19, or 20. In an embodiment, such nucleic acid construct further comprises an intron sequence comprising at least splice sites required for splicing of the intron sequence, said first nucleotide sequence not comprising a GAA repeat nucleotide sequence. In the latter case, the first nucleotide sequence may have at least about 60% sequence identity, or at least 60% sequence identity, or at least 70% sequence identity, or at least 80% sequence identity, or at least 90% sequence identity or 100% sequence identity with the nucleotide sequence of SEQ ID No. 4, 21, 22, or 23.

In a further embodiment, said nucleic acid construct comprises a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence. In the first nucleotide sequence the order of the nucleotide sequences may be the following: 5' TC-rich nucleotide sequence-A-rich nucleotide sequence-A-rich nucleotide sequence-A-rich nucleotide sequence-GT-rich nucleotide sequence-A-rich nucleotide sequence-GAA repeat nucleotide sequence 3', which nucleotide sequences may be separated from each other by 1-50 nucleotides. In this case, the first nucleotide sequence may have at least about 60% sequence identity or at least 60% sequence identity, or at least 70% sequence identity, or at least 80% sequence identity, or at least 90% sequence identity or 100% sequence identity with the nucleotide sequence of SEQ ID No. 5, 24, 25, 26, 27, 28, or 29.

Alternatively, said nucleic acid construct may comprise a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, wherein said GAA repeat nucleotide sequence is located 3' of any one or more of said TC-rich nucleotide sequence, A-rich nucleotide sequences, and/or GT-rich nucleotide sequence. In the first nucleotide sequence the order of the nucleotide sequences may be the following: 5' TC-rich nucleotide sequence-A-rich nucleotide sequence-A-rich nucleotide sequence-A-rich nucleotide sequence-A-rich nucleotide sequence-GT-rich nucleotide sequence-A-rich nucleotide sequence-GAA repeat nucleotide sequence-intron sequence 3', which nucleotide sequences may be separated from each other by 1-50 nucleotides. Such first nucleotide sequence may have at least about 60% sequence identity or at least 60% sequence identity, or at least 70% sequence identity, or at least 80% sequence identity, or at least 90% sequence identity or 100% sequence identity with the nucleotide sequence of SEQ ID NO:30. Alternatively, in the first nucleotide sequence the order of the nucleotide sequences may be the following: 5' TC-rich nucleotide sequence-A-rich nucleotide sequence-A-rich nucleotide sequence-A-rich nucleotide sequence-A-rich nucleotide sequence-GT-rich nucleotide sequence-A-rich nucleotide sequence-intron sequence-GAA repeat nucleotide sequence 3', which nucleotide sequences may be separated from each other by 1-50 nucleotides. Such first nucleotide sequence may have at least about 60% sequence identity or at least 60% sequence identity, or at least 70% sequence identity, or at least 80% sequence identity, or at least 90% sequence identity or 100% sequence identity with the nucleotide sequence of SEQ ID NO: 31.

In a further aspect, the invention pertains to a nucleic acid construct that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence.

In another aspect, the invention is related to a nucleic acid construct that comprises: a TC-rich nucleotide sequence comprising at least 8 consecutive C or T nucleotides, at least 3 A-rich nucleotide sequences comprising at least 5 consecutive A nucleotides, and a GT-rich nucleotide sequence comprising at least 10 nucleotides, at least 80% of which are G or T nucleotides, said first nucleotide sequence not comprising a GAA repeat nucleotide sequence.

In yet another aspect, the invention is concerned with a nucleic acid construct that comprises: a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, said first nucleotide sequence not comprising a GAA repeat nucleotide sequence.

The invention also relates to a nucleic acid construct that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence.

In a further aspect, the invention is directed to a nucleic acid construct that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, wherein said GAA repeat nucleotide sequence is located 3' of any one or more of said TC-rich nucleotide sequence, A-rich nucleotide sequences, and/or GT-rich nucleotide sequence.

In further aspects, the invention provides for a chimeric gene comprising a nucleic acid construct of the present invention, a vector comprising a nucleic acid construct of the present invention or a chimeric gene of the present invention, and a host cell comprising a nucleic acid construct, chimeric gene, or vector of the present invention.

The invention also provides for a non-human transformed organism which is transformed with a nucleic acid construct according to the present invention, a chimeric gene according to the present invention, or a vector according to the present invention, preferably comprising such nucleic acid construct, chimeric gene, or vector. In an embodiment, such organism may be a plant, or a non-human mammal.

The target cell in the method of the invention may be an embryonal target cell. The target cell and/or target tissue may be a plant cell and/or plant tissue, step c) comprising regenerating said transformed target cell and/or target tissue into a transformed plant.

In another aspect, the invention is directed to the use of a nucleotide sequence comprising a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, and, optionally, a GAA repeat nucleotide sequence, in a nucleic acid construct for increasing integration of said nucleic acid construct into a genome.

Said nucleotide sequence may be operably linked to a second nucleotide sequence encoding a protein or polypeptide of interest, and may further be operably linked to a promoter.

In yet another aspect, the invention relates to the use of a nucleotide sequence having at least about 50% sequence identity or at least 50% sequence identity or at least 60% sequence identity, or at least 70% sequence identity, or at least 80% sequence identity, or at least 90% sequence identity or 100% sequence identity to any one of SEQ ID NOS: 1-39 or a nucleotide sequence according to the present invention, said nucleotide sequence being operably linked to a promoter but not to a second nucleotide sequence encoding a protein or polypeptide, for enhancing translation and/or mRNA usage of a recombinantly expressed polypeptide.

In a further aspect, the invention relates to the use of a nucleotide sequence having at least about 50% sequence identity or at least 50% sequence identity or at least 60% sequence identity, or at least 70% sequence identity, or at least 80% sequence identity, or at least 90% sequence identity or 100% sequence identity to any one of SEQ ID NOS: 1-39, or a nucleotide sequence according to the present invention, for increasing the number of transformants upon transformation of a eukaryotic cell with a nucleic acid construct comprising a nucleotide sequence according to the invention.

DESCRIPTION OF THE INVENTION

Definitions

Below follow definitions of terms as used in the invention.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA, ssRNA, dsRNA, non coding RNAs, hnRNA, pre-mRNA, matured mRNA or any combination thereof. The terms "nucleic acid sequence" and "nucleotide sequence" as used herein are interchangeable, and have their usual meaning in the art. The term refers to a DNA or RNA molecule in single or double stranded form. An "isolated nucleic acid sequence" refers to a nucleic acid sequence which is no longer in the natural environment from which it was isolated.

The term "gene" means a DNA sequence comprising a region (transcribed region), which is transcribed into an RNA molecule (e.g. an mRNA) in a cell, operably linked to suitable transcription regulating regions (e.g. a promoter, and/or a translation-enhancing element of the present invention). A gene may thus comprise several operably linked sequences, such as a promoter, a 5' non-translated sequence (also referred to as 5'UTR, which corresponds to the transcribed mRNA sequence upstream of the translation start codon) comprising, for example, sequences involved in translation initiation, a (protein) coding region (cDNA or genomic DNA) and a 3'non-translated sequence (also referred to as 3' untranslated region, or 3'UTR) comprising e.g. transcription termination sites and polyadenylation site (such as e.g. AAUAAA or variants thereof).

A "chimeric gene" (or recombinant gene) refers to any gene, which is not normally found in nature in a species, in particular a gene in which one or more parts of the nucleic acid sequence are present that are not associated with each other in nature. For example, the promoter is not associated in nature with part or all of the transcribed region or with another regulating region. The term "chimeric gene" is understood to include expression constructs in which a promoter or transcription regulating sequence is operably linked to one or more sense sequences (e.g. coding sequences) or to an antisense (reverse complement of the sense strand) or inverted repeat sequence (sense and antisense, whereby the RNA transcript forms double stranded RNA upon transcription).

A "nucleic acid construct" or "vector" or "plasmid" is herein understood to mean a man-made (usually circular) nucleic acid molecule resulting from the use of recombinant DNA technology and which is used to deliver exogenous DNA into a host cell. Vectors usually comprise further genetic elements to facilitate their use in molecular cloning, such as e.g. selectable markers, multiple cloning sites and the like (see below). A nucleic acid construct may also be part of a recombinant viral vector for expression of a protein in a plant or plant cell (e.g. a vector derived from cauliflower mosaic virus, CaMV, or tobacco mosaic virus, TMV) or in a mammalian organism or mammalian cell system (e.g. a vector derived from Moloney murine leukemia virus (MMLV; a Retrovirus) a Lentivirus, an Adeno-associated virus (AAV) or an adenovirus (AdV)).

A "host cell" or a "recombinant host cell" or "transformed cell" are terms referring to a new individual cell (or organism), arising as a result of the introduction into said cell of at least one nucleic acid molecule, especially comprising a chimeric gene encoding a desired protein or a nucleic acid sequence which upon transcription yields an antisense RNA for silencing of a target gene/gene family. The host cell may be a plant cell, a bacterial cell (e.g. an *Agrobacterium* strain), a fungal cell (including a yeast cell), an animal (including insect, mammalian) cell, etc. The host cell may contain the nucleic acid construct as an extra-chromosomally (episomal) replicating molecule, as a non-replicating molecule or comprises the chimeric gene integrated in the nuclear or organellar DNA of the host cell. The term "organism" as used herein, encompasses all organisms consisting of more than one cell, i.e., multicellular organisms, and includes multicellular fungi.

"Transformation" and "transformed" refers to the transfer of a nucleic acid sequence, generally a nucleic acid sequence comprising a chimeric gene of interest (GOI), into the nuclear genome of a cell to create a "transgenic" cell or organism comprising a transgene. The introduced nucleic acid sequence is generally, but not always, integrated in the host genome. When the introduced nucleic acid sequence is not integrated in the host genome, one may speak of "transfection", "transiently transfected", and "transfected". For the purposes of the present patent specification, the terms "transformation", "transiently transfected", and "transfection" are used interchangeably, and refer to stable or transient presence of a nucleic acid sequence into a cell or organism.

As used herein, the term "operably linked" refers to two or more nucleic acid sequence elements that are physically linked and are in a functional relationship with each other. For instance, a promoter is operably linked to a coding sequence if the promoter is able to initiate or regulate the transcription or expression of a coding sequence, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one skilled in the art to act directly or indirectly to regulate the amount of transcription from the promoter. The promoter does not include the transcription start site (TSS) but rather ends at nucleotide −1 of the transcription site, and does not include nucleotide sequences that become untranslated regions in the transcribed mRNA such as the 5'UTR. The "5'UTR" is the sequence starting with nucleotide 1 of the mRNA and ending with nucleotide −1 of the start codon. It is possible that a regulating part of the promoter is comprised within the nucleotide sequence becoming a 5'UTR; however, in such case, the 5'UTR is still not part of the promoter as herein defined.

"Expression of a gene" refers to the process wherein a DNA region, which is operably linked to appropriate regulating regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). An active protein in certain embodiments refers to a protein being constitutively active. The coding sequence is preferably in sense-orientation and encodes a desired, biologically active protein or peptide, or an active peptide fragment, said active peptide fragment having the same type of activity as the peptide is has been derived from.

Any nucleotide sequences capable of hybridising to the nucleotide sequences of the invention are defined as being part of the cis-acting elements of the invention.

Stringent hybridisation conditions are herein defined as conditions that allow a nucleic acid sequence of at least 25, preferably 50, 75 or 100, and most preferably 150 or more nucleotides, to hybridise at a temperature of about 65° C. or of 65° C. in a solution comprising about 1 M salt or 1 M salt, preferably 6×SSC or any other solution having a comparable ionic strength, and washing at 65° C. in a solution comprising about 0.1 M salt, or 0.1 M salt or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity or at least 90% sequence identity. Moderate hybridization conditions are herein defined as conditions that allow a nucleic acid sequence of at least 50, preferably 150 or more nucleotides, to hybridise at a temperature of about 45° C. or of 45° C. in a solution comprising about 1 M salt or 1 M salt, preferably 6×SSC or any other solution having a comparable ionic strength, and washing at room temperature in a solution comprising about 1 M salt, or 1 M salt preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically be operably linked to another promoter sequence or, if applicable, another secretory signal sequence and/or terminator sequence than in its natural environment.

When used to indicate the relatedness of two nucleic acid sequences the term "homologous" means that one single-stranded nucleic acid sequence may hybridise to a complementary single-stranded nucleic acid sequence. The degree of hybridisation may depend on a number of factors including the extent of identity between the sequences and the hybridisation conditions such as temperature and salt concentration as discussed later. Preferably the region of identity is greater than 5 bp, more preferably the region of identity is greater than 10 bp.

The term "heterologous" when used with respect to a nucleic acid or polypeptide molecule refers to a nucleic acid or polypeptide from a foreign cell which does not occur naturally as part of the organism, cell, genome or DNA or RNA sequence in which it is present, or which is found in a cell or location or locations in the genome or DNA or RNA sequence that differ from that in which it is found in nature. Heterologous nucleic acids or proteins are not endogenous to the cell into which they are introduced, but have been obtained from another cell or synthetically or recombinantly produced. Generally, though not necessarily, such nucleic acids encode proteins that are not normally produced by the cell in which the DNA is transcribed or expressed, similarly exogenous RNA codes for proteins not normally expressed in the cell in which the exogenous RNA is present. Furthermore, it is known that a heterologous protein or polypeptide can be composed of homologous elements arranged in an order and/or orientation not normally found in the host organism, tissue or cell thereof in which it is transferred, i.e. the nucleotide sequence encoding said protein or polypeptide originates from the same species but is substantially modified from its native form in composition and/or genomic locus by deliberate human intervention. Heterologous nucleic acids and proteins may also be referred to as foreign nucleic acids or proteins. Any nucleic acid or protein that one of skill in the art would recognise as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

The term "endogenous" when used with respect to a nucleic acid or polypeptide molecule refers to a nucleic acid or polypeptide as natively expressed in a cell or in an organism as identified herein.

"Sequence identity", as known in the art, is a relationship between two or more amino acid (polypeptide or protein) sequences or two or more nucleic acid (polynucleotide) sequences, as determined by comparing the sequences. In the art, the percentage of "identity" indicates the degree of sequence relatedness between amino acid or nucleic acid sequences as determined by the match between strings of such sequences. In an embodiment, sequence identity is assessed on a whole SEQ ID NO as defined herein or on a part thereof. Part thereof preferably means at least 50%, 60%, 70%, 80%, 90% or 100% of the length of said sequence identified by its SEQ ID NO.

"Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1):387 (1984)), BestFit and FASTA (Altschul, S. F. et al., J. Mol. Biol. 215:403-410 (1990). The BLAST 2.0 family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. The BLASTX program is publicly available from NCBI and other sources (BLAST Manual, Altschul, S., et al., NCBI NLM NIH Bethesda, Md. 20894; Altschul, S., et al., J. Mol. Biol. 215:403-410 (1990)). The well-known Smith Waterman algorithm may also be used to determine identity.

Preferred parameters for nucleic acid comparison include the following: Algorithm: Needleman and Wunsch, J. Mol. Biol. 48:443-453 (1970). Needle reads two input sequences and writes their optimal global sequence alignment to file. It uses the Needleman-Wunsch alignment algorithm to find the optimum alignment (including gaps) of two sequences along their entire length. The algorithm uses a dynamic programming method to ensure the alignment is optimum, by exploring all possible alignments and choosing the best. A scoring matrix is read that contains values for every possible residue or nucleotide match. Needle finds the alignment with the maximum possible score where the score of an alignment is equal to the sum of the matches taken from the scoring matrix, minus penalties arising from opening and extending gaps in the aligned sequences. The substitution matrix and gap opening and extension penalties are user-specified.

The Needleman-Wunsch algorithm is a member of the class of algorithms that can calculate the best score and alignment of two sequences in the order of mn steps, where n and m are the sequence lengths. These dynamic programming algorithms were first developed for protein sequence comparison by Needleman and Wunsch, though similar methods were independently devised during the late 1960's and early 1970's for use in the fields of speech processing and computer science. An important problem is the treatment of gaps, i.e., spaces inserted to optimize the alignment score. A penalty is subtracted from the score for each gap opened (the 'gap open' penalty) and a penalty is subtracted from the score for the total number of gap spaces multiplied by a cost (the 'gap extension' penalty). Typically, the cost of extending a gap is set to be 5-10 times lower than the cost for opening a gap. There are two ways to compute a penalty for a gap of n positions: "gap opening penalty+(n−1)*gap extension penalty" or "gap penalty+n*gap length penalty". The two methods are basically equivalent. The first way is used by EMBOSS and WU-BLAST. The second way is used by NCBI-BLAST, GCG, Staden and CLUSTAL. In a Needleman-Wunsch global alignment, the entire length of each sequence is aligned. The sequences might be partially overlapping or one sequence might be aligned entirely internally to the other. There is no penalty for the hanging ends of the overlap. In bioinformatics, it is usually reasonable to assume that the sequences are incomplete and there should be no penalty for failing to align the missing nucleotides. Needle is a true implementation of the Needleman-Wunsch algorithm and so produces a full path matrix. It therefore cannot be used with genome sized sequences unless you've a lot of memory and a lot of time.

"Messenger RNA (mRNA)" as used herein refers to a temporary complementary copy of RNA of the antisense strand (anticoding strand or template) of protein coding DNA. In eukaryotes it is usually transcribed as a relatively long pre-mRNA (also called primary transcript or hnRNA) which is then processed, still within the nucleus, to remove introns. Further post-transcriptional modifications can also occur. The mature mRNA is then transported into the cytoplasm where it is translated into protein on the ribosome. Furthermore, an mRNA generally comprises a region that specifies the protein sequence, flanked on either side by untranslated regions called 5' and 3'untranslated regions (5'UTR and 3'UTR).

"Antisense nucleic acid" as used herein refers to a RNA, DNA or PNA molecule that is complementary to all or part of a target primary transcript or mRNA and that blocks the translation of a target nucleotide sequence.

As used herein, the term "plant" refers to either a whole plant, including in general the class of higher plants amenable to transformation techniques, including both monocotyledonous and dicotyledonous plants or a part of a plant such as e.g. roots, stems, stalks, leaves, petals, fruits, seeds, tubers, pollen, meristems, callus, sepals, bulbs and flowers. The term plant as used herein further refers, without limitations, to plant cells in seeds, suspension cultures, embryos, meristematic regions, callus tissue, leaves, roots, shoots, gametophytic and sporophytic tissue, pollen, protoplasts and microspores. Furthermore, all plant tissues in all organs are included in the definition of the term plant as used herein. Plant tissues include, but is not limited to, differentiated and undifferentiated tissues of a plant, including pollen, pollen tubes, pollen grains, roots, shoots, shoot meristems, coleoptilar nodes, tassels, leaves, cotyledonous petals, ovules, tubers, seeds, kernels. Tissues of plants may be in planta, or in organ, tissue or cell culture. As used herein, monocotyledonous plant refers to a plant whose seeds have only one cotyledon, or organ of the embryo that stores and absorbs food. As used herein, dicotyledonous plant refers to a plant whose seeds have two cotyledons. Plants included in the invention are all plants amenable to transformation. The term "plant" as used herein includes algae and micro-algae. In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements.

The indefinite article "a" or "an" thus usually means "at least one". It is further understood that, when referring to "sequences" herein, generally the actual physical molecules with a certain sequence of units or subunits (e.g. nucleic acids or amino acids) are referred to.

The word "about" when used in association with an integer (about 10) preferably means that the value may be the given value of 10 more or less 1 of the value: about 10 preferably means from 9 to 11. The word "about" when used in association with a numerical value (about 10.6) preferably means that the value may be the given value of 10.6 more or less 1% of the value 10.6.

DETAILED DESCRIPTION OF THE INVENTION

Isolated Nucleic Acid Sequences of the Invention, Nucleic Acid Constructs, Vectors and Host Cells The nucleotide sequences of the present invention originate from the 5'UTR sequence of the *Nicotiana tabacum* ntp303 gene. This 172 nucleotide long 5'UTR sequence (SEQ ID NO:1) comprises several distinct areas: a GAA repeat (nt 14-50 of SEQ ID NO:1), followed by a TC-rich repeat (nt 54-68 of SEQ ID NO:1), 4 A-rich areas (nt 77-87, 93-105, 111-121, and 126-132 of SEQ ID NO:1, respectively), a GT-rich area (nt 133-148 of SEQ ID NO:1), and another A-rich area (nt 152-169 of SEQ ID NO:1). In the 5'UTR sequence of the *Nicotiana tabacum* ntp303 gene, these areas are separated from one another by from between 0-8 nucleotides. Calculations on the energetically most stable structure have revealed that the energetically most stable structure assumed by a nucleotide sequence having SEQ ID NO:1 would comprise 2 hairpins; the first hairpin encompassing nt 4-76 of SEQ ID NO:1, and the second hairpin encompassing nt 104-151 of SEQ ID NO:1. However, in nature a nucleotide sequence does not necessarily adopt the energetically most stable structure, and as such the structure of the 5'UTR sequence of the *Nicotiana tabacum* ntp303 gene remains unresolved.

The present inventors have now identified novel mRNA usage and/or translation-enhancing nucleotide sequences that enhance mRNA usage and do not inhibit transcription to the same extent as the 5'UTR sequence of the *Nicotiana tabacum* ntp303 gene. The nucleotide sequences may be isolated nucleotide sequences.

In an aspect, the present invention provides an nucleotide sequence that comprises at least the following nucleotide regions: a GAA repeat nucleotide sequence, a TC-rich nucleotide sequence comprising at least about 8 or at least 8 consecutive C or T nucleotides, at least three A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing the intron sequence. Preferably, the intron sequence is not preceded by an exon nucleotide sequence, and is part of an untranslated region.

The invention also provides for a nucleotide sequence comprising at least the following nucleotide regions: a TC-rich nucleotide sequence comprising at least 8 consecutive C or T nucleotides, at least three A-rich nucleotide sequences comprising at least 5 consecutive A nucleotides, and a GT-rich nucleotide sequence comprising at least 10 nucleotides, at least 80% of which are G or T nucleotides, said nucleotide sequence not comprising a GAA repeat nucleotide sequence.

The invention further provides a nucleotide sequence that comprises: a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, said first nucleotide sequence not comprising a GAA repeat nucleotide sequence.

Also, the invention is directed to a nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence.

Another nucleotide sequence of the invention comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, wherein said GAA repeat nucleotide sequence is located 3' of any one or more of said TC-rich nucleotide sequence, A-rich nucleotide sequences, and/or GT-rich nucleotide sequence.

The nucleotide sequences of the invention are not limited to a specific number of nucleotides. They may comprise between about 40 and about 3,000 nucleotides, such as between about 45 and about 2,500 nucleotides, about 50 and about 2,000 nucleotides, about 55 and about 1,500 nucleotides, about 60 and about 1,000 nucleotides, about 75 and about 800 nucleotides, about 85 and about 600 nucleotides, about 100 and about 500 nucleotides, about 120 and about 450 nucleotides, about 130 and about 300 nucleotides, about 135 and about 250 nucleotides, or about 140 and 200 nucleotides.

They may also comprise from 40 to 3,000 nucleotides, such as from 45 to 2,500 nucleotides, from 50 to 2,000 nucleotides, from 55 to 1,500 nucleotides, from 60 to 1,000 nucleotides, from 75 to 800 nucleotides, from 85 to 600 nucleotides, from 100 to 500 nucleotides, from 120 to 450 nucleotides, from 130 to 300 nucleotides, from 135 to 250 nucleotides, from 140 to 200 nucleotides.

Thus, in an aspect, the present invention provides translation-enhancing and/or mRNA usage improving nucleotide sequences based on the 5'UTR sequence of the *Nicotiana tabacum* ntp303 gene further comprising an intron (nucleotide) sequence. Such translation-enhancing and/or mRNA usage improving nucleotide sequences may or may not comprise a GAA repeat nucleotide sequence. If a translation-enhancing and/or mRNA usage improving nucleotide sequence comprises a GAA repeat nucleotide sequence, such GAA repeat nucleotide sequences may be located in any location in the nucleotide sequence, e.g., it may be located 5' of the TC-rich, A-rich, and GT-rich nucleotide sequences as is the case for SEQ ID NO:1, or it may be located 3' of all of the TC-rich, A-rich, and GT-rich nucleotide sequences. Alternatively, such GAA repeat nucleotide sequences may be located in between any of the TC-rich, A-rich, and GT-rich nucleotide sequences.

In another aspect, the present invention provides translation-enhancing nucleotide sequences lacking a GAA repeat nucleotide sequence, but comprising the TC-rich, A-rich, and GT-rich nucleotide sequences referred to above.

In yet another aspect, the present invention provides for translation-enhancing and/or mRNA usage improving nucleotide sequences comprising a GAA repeat nucleotide sequence, wherein such GAA repeat nucleotide sequences is located 3' of all of the TC-rich, A-rich, and GT-rich nucleotide sequences, or in between any of the TC-rich, A-rich, and GT-rich nucleotide sequences.

A nucleotide sequence according to the invention can be present in the form of RNA or in the form of DNA including genomic DNA, i.e. DNA including the introns, cDNA or synthetic DNA. The DNA may be double-stranded or single-stranded and if single-stranded may be the coding strand or non-coding (anti-sense) strand. DNA or RNA with a backbone modified for stability or for other reasons are a further part of the invention. Moreover, DNA or RNA comprising unusual nucleotides, such as inosine, or modified nucleotides, such as tritylated nucleotides are also a part of the invention. The nucleotide sequence may also be a allelic variant of the nucleotide sequence according to the invention. If desired, the nucleotide sequence can be prepared or altered synthetically so the known codon preferences of the intended expression host can advantageously be used. It has been shown for instance that the codon preferences and GC content preferences of monocotyledons and dicotyledons differ (Murray et al., Nucl. Acids Res. 17: 477-498 (1989)). The nucleotide sequences may be isolated nucleotide sequences. The nucleotide sequence may be part of a chimeric gene.

The various nucleotide sequence regions (including TC-rich, A-rich, GT-rich, GAA repeat, intron, CAA repeat, and/or TATA nucleotide sequences) making up the nucleic acid sequences of the present invention may be separated from each other by about 0-100 nucleotides, preferably by about 0-75, 0-65, 1-55, 1-50, 1-45, 1-40, 1-35, 1-30, 1-25, 1-20, 1-15, 2-10, 2-9, 2-8, 2-7, 2-6, 2-5, or 2-4 or preferably by 0-75, 0-65, 1-55, 1-50, 1-45, 1-40, 1-35, 1-30, 1-25, 1-20, 1-15, 2-10, 2-9, 2-8, 2-7, 2-6, 2-5, or 2-4 nucleotides.

The GAA repeat nucleotide sequence may be a perfect GAA repeat having the structure $(GAA)_n$, wherein n is an integer being 3, 4, 5, 6, 7, 8, 9, 10, or more. A non-limiting example of such perfect GAA repeat nucleotide sequence is SEQ ID NO: 41. Alternatively, the GAA repeat nucleotide sequence may be an imperfect GAA repeat having the structure $(GAA)_k(X)_l(GAA)_m$, wherein k is an integer being 3, 4, 5, 6, 7, 8, 9, 10, or more, X may be A, C, G, or T, however, preferably A, and l is an integer being 1, 2, 3, 4, 5, 6, 7, 8, or more, and m is an integer being 3, 4, 5, 6, 7, 8, 9, 10, or more. Preferably, said GAA repeat nucleotide sequence comprises 10, 9, 8, 7, 6, 5, 4 or 3 GAA units. The GAA repeat nucleotide sequence may have at least about 50, 55, 60, 65, 70, 75, 80, 85, 90, 95, 96, 97, 98, 99, 100% or at least 50, 55, 60, 65, 70, 75, 80, 85, 90, 95, 96, 97, 98, 99, 100% sequence identity with nucleotides 14-50 of SEQ ID NO:1. In an embodiment, the GAA repeat nucleotide sequence may be an imperfect GAA repeat having the structure $(GAA)_3A(T/G)AA(GAA)_8$ (SEQ ID NO: 40).

The TC-rich nucleotide sequence of the present invention comprises at least about 8, 9, 10, 11, 12, 13, 14, 15, 16, 17, 18, 19, 20, or more, or 8, 9, 10, 11, 12, 13, 14, 15, 16, 17, 18, 19, 20, or more consecutive C or T nucleotides. The TC-rich nucleotide sequence may be the sequence of nucleotides 54-68 of SEQ ID NO:1, or any sequence having at least about 70, 75, 80, 85, 90, 95, 96, 97, 98, 99, 100% or at least 70, 75, 80, 85, 90, 95, 96, 97, 98, 99, 100% sequence identity to nucleotides 54-68 of SEQ ID NO:1. For example, the TC-rich nucleotide sequence may comprise a nucleotide sequence similar to nucleotides 54-68 of SEQ ID NO:1, comprising one or more insertions, deletions and/or replacements.

The A-rich nucleotide sequences of the present invention comprise at least 5 consecutive A nucleotides. Preferably, the A-rich nucleotide sequences comprise at least about 7, 8, 9, or 10 A nucleotides or at least 7, 8, 9, or 10 A nucleotides in a stretch of about 10 nucleotides or of 10 nucleotides. The A-rich nucleotides may comprise any nucleotide sequence selected from the group of nucleotides 77-87, nucleotides 93-105, nucleotides 111-121, nucleotides 126-132, or nucleotides 152-169 of SEQ ID NO:1, or any nucleotide sequence having at least about 80, 85, 90, 95, 96, 97, 98, 99, 100% sequence identity or at least 80, 85, 90, 95, 96, 97, 98, 99, 100% sequence identity with either one of said nucleotides of SEQ ID NO:1. For example, an A-rich nucleotide sequence may comprise a nucleotide sequence similar to nucleotides 77-87, nucleotides 93-105, nucleotides 111-121, nucleotides 126-132, or nucleotides 152-169 of SEQ ID NO:1, respectively, comprising one or more insertions, deletions and/or replacements. It is to be noted that a T nucleotide amidst A nucleotides can function as a polyadenylation signal and may result in cleavage of RNA. Nucleic acid sequences of the invention may be corrected for such polyadenylation signal by replacement of the T nucleotide by, for example, a G nucleotide.

The GT-rich nucleotide sequence of the present invention comprising at least 10, such as at least 11, at least 12, at least 13, or more, nucleotides, at least 80%, preferably at least 90%, most preferably at least 100%, of which are G or T nucleotides. The GT-rich nucleotide sequence may comprise nucleotides 133-148 of SEQ ID NO:1, or a nucleotide sequence having at least about 70, 75, 80, 85, 90, 95, 96, 97, 98, 99, 100% sequence identity or at least 70, 75, 80, 85, 90, 95, 96, 97, 98, 99, 100% sequence identity with nucleotides 133-148 of SEQ ID NO:1. For example, the GT-rich nucleotide sequence may comprise a nucleotide sequence similar to nucleotides 133-148 of SEQ ID NO:1, comprising one or more insertions, deletions and/or replacements.

The intron sequence comprising at least splice sites required for splicing of the intron sequence. Introns result in the formation of a spliceosome, a complex with multiple RNA and protein molecules. The splicing process results in an increased stability, nucleolar export and translatability of (pre-)mRNA. In an embodiment, the intron sequence comprises a splice site GT at the 5' end of the nucleotide sequence, and a splice site AG at the 3' end of the nucleotide sequence, which splice site AG is preferably preceded by a TC-rich nucleotide sequence, optionally separated from said splice site AG by about 1-50 nucleotides or by 1-50 nucleotides. The splice site at the 5'end of the nucleotide sequence may comprise the sequence 5'-AGGT(A/G)AG-3', or 5'-AGGTAAGT-3'. The splice site at the 3'end of the nucleotide sequence may comprise the sequence 5'-(C/T)$_n$AGG-3'. The intron sequence may further comprise a branch (splice) site comprising the nucleotide sequence (C/T)T(A/G)A(C/T), at the 5' side of the TC-rich nucleotide sequence. In an embodiment, the branch site comprises the nucleotide sequence CTGAC. Alternatively, the branch site comprises the nucleotide sequence CTAAC. A non-limiting example of a branch site may be TACTAACTCTT. The intron sequence may comprise a nucleotide sequence having at least about 80, 85, 90, 95, 96, 97, 98, 99, 100% sequence identity or at least 80, 85, 90, 95, 96, 97, 98, 99, 100% sequence identity with nucleotides 171-277 of SEQ ID NO:2, nucleotides 171-274 of SEQ ID NO:7, nucleotides 133-210 of SEQ ID NO:8, nucleotides 134-211 of SEQ ID NO:9, nucleotides 134-226 of SEQ ID NO:10, nucleotides 134-226 of SEQ ID NO:11, nucleotides 133-225 of SEQ ID NO:12, nucleotides 134-226 of SEQ ID NO:13, nucleotides 146-257 of SEQ ID NO:14, or nucleotides 147-223 of SEQ ID NO:15.

All nucleic acid sequences of the present invention preferably comprise a TC-rich nucleotide sequence, at least 3 A-rich nucleotide sequences, and a GT-rich nucleotide sequence as described above. In one embodiment, these various nucleotide sequences are present in the following order: TC-rich nucleotide sequence-A-rich nucleotide sequence-A-rich nucleotide sequence-GT-rich nucleotide sequence-A-rich nucleotide sequence. When a GAA repeat nucleotide sequence is included in the nucleic acid sequence of the present invention, it may be included anywhere in the preferred order, i.e., in between the TC-rich nucleotide sequence, A-rich nucleotide sequences, and TC-rich nucleotide sequence, or 5' or 3' of all of the TC-rich nucleotide sequence, A-rich nucleotide sequences, and TC-rich nucleotide sequence.

In one embodiment, as described above, the nucleic acid sequence of the invention comprises a GAA repeat nucleotide sequence, a TC-rich nucleotide sequence, at least 3, such as 4 or 5, or more, A-rich nucleotide sequences, a GT-rich nucleotide sequence, and an intron sequence. The intron sequence may be located 3' of all of the GAA repeat nucleotide sequence, the TC-rich nucleotide sequence, the at least 3 A-rich nucleotide sequences, and the GT-rich nucleotide sequence. Alternatively, the intron sequence may be located 5' of all of the GAA repeat nucleotide sequence, the TC-rich nucleotide sequence, the at least 3 A-rich nucleotide sequences, and the GT-rich nucleotide sequence. The intron sequence may also be located in between any of the GAA repeat nucleotide sequence, the TC-rich nucleotide sequence, the at least 3 A-rich nucleotide sequences, and the GT-rich nucleotide sequence. In an embodiment, the order of the various nucleotide sequences is any of the following (in the direction of the 5'end to the 3'end): GAA repeat-TC-rich sequence-A-rich sequence-A-rich sequence-GT-rich sequence-A-rich sequence-intron sequence; intron sequence-GAA repeat-TC-rich sequence-A-rich sequence-A-rich sequence-GT-rich sequence-A-rich sequence; GAA repeat-intron sequence-TC-rich sequence-A-rich sequence-A-rich sequence-GT-rich sequence-A-rich sequence; GAA repeat-TC-rich sequence-intron sequence-A-rich sequence-A-rich sequence-GT-rich sequence-A-rich sequence; GAA repeat-TC-rich sequence-A-rich sequence-intron sequence-A-rich sequence-GT-rich sequence-A-rich sequence; GAA repeat-TC-rich sequence-A-rich sequence-A-rich sequence-intron sequence-GT-rich sequence-A-rich sequence; GAA repeat-TC-rich sequence-A-rich sequence-A-rich sequence-GT-rich sequence-intron sequence-A-rich sequence. In an embodiment, such nucleotide sequence has at least about 50, 55, 60, 65, 70, 75, 80, 85, 90, 95, 96, 97, 98, 99, 100% nucleotide sequence identity or at least 50, 55, 60, 65, 70, 75, 80, 85, 90, 95, 96, 97, 98, 99, 100% nucleotide sequence identity with the nucleotide sequence of SEQ ID NOs:2, 7, 8, 9, 10, 11, 12, 13, 14, or 15.

In another embodiment, as described above, the nucleic acid sequence of the invention comprises a TC-rich nucleotide sequence, at least 3 A-rich nucleotide sequences, and a GT-rich nucleotide sequence, and does not comprise a GAA repeat nucleotide sequence. In an embodiment, such nucleotide sequence has at least about 50, 55, 60, 65, 70, 75, 80, 85, 90, 95, 96, 97, 98, 99, 100% nucleotide sequence identity or at least 50, 55, 60, 65, 70, 75, 80, 85, 90, 95, 96, 97, 98, 99, 100% nucleotide sequence identity with the nucleotide sequence of SEQ ID NOs:3, 16, 17, 18, 19, or 20. Said isolated nucleic acid sequence may further comprise an intron sequence. The intron sequence may be located 3' of all of the the TC-rich nucleotide sequence, the at least 3 A-rich nucleotide sequences, and the GT-rich nucleotide sequence. Alternatively, the intron sequence may be located 5' of all of the TC-rich nucleotide sequence, the at least 3 A-rich nucleotide sequences, and the GT-rich nucleotide sequence. The intron sequence may also be located in between any of the the TC-rich nucleotide sequence, the at least 3 A-rich nucleotide sequences, and the GT-rich nucleotide sequence. In an embodiment, the order of the various nucleotide sequences is any of the following (in the direction from the 5' end to the 3' end): TC-rich sequence-A-rich sequence-A-rich sequence-GT-rich sequence-A-rich sequence-intron sequence; intron sequence-TC-rich sequence-A-rich sequence-A-rich sequence-GT-rich sequence-A-rich sequence; intron sequence-TC-rich sequence-A-rich sequence-A-rich sequence-GT-rich sequence-A-rich sequence; TC-rich sequence-intron sequence-A-rich sequence-A-rich sequence-GT-rich sequence-A-rich sequence; TC-rich sequence-A-rich sequence-intron sequence-A-rich sequence-GT-rich sequence-A-rich sequence; TC-rich sequence-A-rich sequence-A-rich sequence-intron sequence-GT-rich sequence-A-rich sequence; TC-rich sequence-A-rich sequence-GT-rich sequence-intron sequence-A-rich sequence. In an embodiment, such nucleotide sequence lacking a GAA repeat nucleotide sequence but comprising an intron sequence has at least about 50, 55, 60, 65, 70, 75, 80, 85, 90, 95, 96, 97, 98, 99, 100% nucleotide sequence identity or at least 50, 55, 60, 65, 70, 75, 80, 85, 90, 95, 96, 97, 98, 99, 100% nucleotide sequence identity with the nucleotide sequence of SEQ ID NOs:4, 21, 22, or 23.

In a further embodiment, the present invention relates to a nucleic acid sequence comprising: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence. The order of the nucleotide sequences may be the following (from the 5' end to the 3' end): TC-rich nucleotide sequence-A-rich nucleotide sequence-A-rich nucleotide sequence-GT-rich nucleotide sequence-A-rich nucleotide sequence-GAA repeat nucleotide sequence; TC-rich nucleotide sequence-GAA repeat nucleotide sequence-A-rich nucleotide sequence-A-rich nucleotide sequence-GT-rich nucleotide sequence-A-rich nucleotide sequence; TC-rich nucleotide sequence-A-rich nucleotide sequence-GAA repeat nucleotide sequence-A-rich nucleotide sequence-GT-rich nucleotide sequence-A-rich nucleotide sequence; TC-rich nucleotide sequence-A-rich nucleotide sequence-A-rich nucleotide sequence-GAA repeat nucleotide sequence-GT-rich nucleotide sequence-A-rich nucleotide sequence; TC-rich nucleotide sequence-A-rich nucleotide sequence-A-rich nucleotide sequence-GT-rich nucleotide sequence-GAA repeat nucleotide sequence-A-rich nucleotide sequence. Said nucleic acid sequence may have at least about 50, 55, 60, 65, 70, 75, 80, 85, 90, 95, 96, 97, 98, 99, or 100% sequence identity or at least 50, 55, 60, 65, 70, 75, 80, 85, 90, 95, 96, 97, 98, 99, or 100% sequence identity with the nucleotide sequence of SEQ ID NOs:5, 24, 25, 26, 27, 28, or 29. The GAA repeat nucleotide sequence may also be located to the 3' untranslated region. Said nucleic acid sequence may further comprise an intron sequence as described above. The intron sequence may be located 3' of all of the TC-rich nucleotide sequence, the at least 3 A-rich nucleotide sequences, GAA repeat nucleotide sequence and the GT-rich nucleotide sequence. Alternatively, the intron sequence may be located 5' of all of the TC-rich nucleotide sequence, the at least 3 A-rich nucleotide sequences, GAA repeat nucleotide sequence and the GT-rich nucleotide sequence. The intron sequence may also be located in between any of the the TC-rich nucleotide sequence, the at least 3 A-rich nucleotide sequences, the GAA repeat nucleotide sequence and the GT-rich nucleotide sequence. In an embodiment, such nucleotide sequence comprising an intron sequence and a GAA repeat nucleotide sequence located 3' of any one or more of said TC-rich nucleotide sequence, A-rich nucleotide sequences, and/or GT-rich nucleotide sequence has at least about 50, 55, 60, 65, 70, 75, 80, 85, 90, 95, 96, 97, 98, 99, 100% nucleotide sequence identity or at least 50, 55, 60, 65, 70, 75, 80, 85, 90, 95, 96, 97, 98, 99, 100% nucleotide sequence identity with the nucleotide sequence of SEQ ID NOs:30, or 31.

The nucleic acid sequences of the present invention may comprise further enhancing elements, such as TATA nucleotide sequences or CAA repeat nucleotide sequences. A TATA box often has the core DNA sequence 5'-TATAAA-3' or a variant, which is usually followed by three or more adenine nucleotides. In an embodiment, such nucleotide sequence comprising a TATA nucleotide sequence has at least about 50, 55, 60, 65, 70, 75, 80, 85, 90, 95, 96, 97, 98, 99, 100% nucleotide sequence identity or at least 50, 55, 60, 65, 70, 75, 80, 85, 90, 95, 96, 97, 98, 99, 100% nucleotide sequence identity with the nucleotide sequence of SEQ ID NOs: 32, 35, 37, 38, or 39. The sequence may comprise the sequence $(CAA)_n$, wherein n is an integer of at least 3, 4, 5, 6, 7, 8, or more (also referred to as a "perfect CAA repeat"). The CAA repeat sequence may be an imperfect $(CAA)_n$ repeat in which the repetition of the CAA repeats may be interrupted by a single nucleotide, often an adenine base. The imperfect CAA repeat may, for example, comprise the nucleotide sequence $(CAA)_k A (CAA)_l$, wherein k and l are integers of at least 2, 3, 4, 5, 6, 7, 8, or more. In an embodiment, the sequence comprises the sequence $(CAA)_3 A (CAA)_2 ACAA$. In an embodiment, such nucleotide sequence comprising a CAA repeat nucleotide sequence has at least about 50, 55, 60, 65, 70, 75, 80, 85, 90, 95, 96, 97, 98, 99, 100% nucleotide sequence identity or at least 50, 55, 60, 65, 70, 75, 80, 85, 90, 95, 96, 97, 98, 99, 100% nucleotide sequence identity with the nucleotide sequence of SEQ ID NOs:32, 33, 34, 35, 36, or 37. The TATA and/or CAA sequences may be located anywhere in the nucleic acid sequence of the invention. The TATA and/or CAA repeat sequence may be located 5' of the TC-rich nucleotide sequence, A-rich nucleotide sequences and GT-rich nucleotide sequences, or may be located 3' of the TC-rich nucleotide sequence, A-rich nucleotide sequences and GT-rich nucleotide sequences, or in between any of the TC-rich nucleotide sequence, A-rich nucleotide sequences and GT-rich nucleotide sequences. The CAA repeat sequence may be used to replace a GAA repeat nucleotide sequence, or may be used in addition to a GAA repeat nucleotide sequence.

The nucleic acid sequences may comprise further mRNA usage improving elements, such as single nucleotide transitions, increasing the stability of the mRNA, removing undesired regulating signal sequences or altering the secondary structure of the mRNA.

The nucleic acid sequences of the present invention may further comprise a second nucleotide sequence encoding a protein or polypeptide of interest that is operably linked to any one of the nucleic acid sequences as defined above. The protein or polypeptide of interest can be a homologous protein or polypeptide, but in a preferred embodiment of the invention the protein or polypeptide of interest is a heterologous protein. A second nucleotide sequence encoding a heterologous protein or polypeptide may be derived in whole or in part from any source known to the art, including a bacterial or viral genome or episome, eukaryotic nuclear or plasmid DNA, cDNA or chemically synthesised DNA. The second nucleotide sequence may constitute an uninterrupted coding region or it may include one or more introns bounded by appropriate splice junctions, it can further be composed of segments derived from different sources, naturally occurring or synthetic. The second nucleotide sequence encoding the protein or polypeptide of interest according to the method of the invention is preferably a full-length nucleotide sequence, but can also be a functionally active part or other part of said full-length nucleotide sequence. The second nucleotide sequence encoding the protein or polypeptide of interest may also comprise signal sequences directing the protein or polypeptide of interest when expressed to a specific location in the cell or tissue. Furthermore, the second nucleotide sequence encoding the protein or polypeptide of interest can also comprise sequences which facilitate protein purification and protein detection by for instance Western blotting and ELISA (e.g. c-myc or polyhistidine sequences). The nucleic acid sequences of the invention operably linked to the second nucleotide sequence may be part of a chimeric gene.

In another aspect, the present invention relates to an mRNA molecule comprising any of the transcribed nucleic acid sequences of the present invention and the transcribed second nucleotide sequence. The transcribed nucleic acid sequences of the present invention will not be translated, whereas the transcribed second nucleotide sequence will be translated.

The protein or polypeptide of interest may have industrial or medicinal (pharmaceutical) applications. Examples of proteins or polypeptides with industrial applications include enzymes such as e.g. lipases (e.g. used in the detergent industry), proteases (used inter alia in the detergent industry, in brewing and the like), cell wall degrading enzymes (such as, cellulases, pectinases, beta.-1,3/4- and beta.-1,6-glucanases, rhamnogalacturonases, mannanases, xylanases, pullulanases, galactanases, esterases and the like, used in fruit processing wine making and the like or in feed), phytases, phospholipases, glycosidases (such as amylases, beta-glucosidases, arabinofuranosidases, rhamnosidases, apiosidases and the like), dairy enzymes (e.g. chymosin). Mammalian, and preferably human, proteins or polypeptides and/or enzymes with therapeutic, cosmetic or diagnostic applications include, but are not limited to, insulin, serum albumin (HSA), lactoferrin, hemoglobin α and β, tissue plasminogen activator (tPA), erythropoietin (EPO), tumor necrosis factors (TNF), BMP (Bone Morphogenic Protein), growth factors (G-CSF, GM-CSF, M-CSF, PDGF, EGF, and the like), peptide hormones (e.g. calcitonin, somatomedin, somatotropin, growth hormones, follicle stimulating hormone (FSH), interleukins (IL-x), interferons (IFN-γ), antibodies, and phosphatases. Also included are bacterial and viral antigens, e.g. for use as vaccines, including e.g. heat-labile toxin B-subunit, cholera toxin B-subunit, envelope surface protein Hepatitis B virus, capsid protein Norwalk virus, glycoprotein B Human cytomegalovirus, glycoprotein S, interferon, and transmissible gastroenteritis corona virus-receptors and the like. Further included are genes coding for mutants or analogues of the said proteins.

The nucleic acid sequences of the present invention are preferably comprised in a nucleic acid construct. Such nucleic acid construct may further comprise a promoter for control and initiation of transcription of the second nucleotide sequence. The promoter preferably is capable of causing expression of the second nucleotide sequence in a host cell of choice. Said promoter, e.g. heterologous, is operably linked to any one of the nucleotide sequences of the invention as mentioned above. In an embodiment of the invention the promoter is a promoter capable of initiating transcription in the host cell of choice. Promoters as used herein include tissue-specific, tissue-preferred, cell-type-specific, inducible and constitutive promoters. Tissue-specific promoters are promoters which initiate transcription only in certain tissues and refer to a sequence of DNA that provides recognition signals for RNA polymerase and/or other factors required for transcription to begin, and/or for controlling expression of the coding sequence precisely within certain tissues or within certain cells of that tissue. Expression in a tissue-specific manner may be only in individual tissues or in combinations of tissues. Tissue-preferred promoters are promoters that preferentially initiate transcription in certain tissues. Cell-type-specific promoters are promoters that primarily drive expression in certain cell types. Inducible promoters are promoters that are capable of activating transcription of one or more DNA sequences or genes in response to an inducer. The DNA sequences or genes will not be transcribed when the inducer is absent. Activation of an inducible promoter is established by application of the inducer. Constitutive promoters are promoters that are active under many environmental conditions and in many different tissue types.

Promoters and/or regulating sequences that may be employed in expression of polypeptides according to the present disclosure in mammalian cells or a non-human mammal include, but are not limited to, the human cytomegalovirus (CMV) promoter, a simian virus (SV40) promoter, a human ubiquitin C promoter or a human elongation factor alpha (EF1-α) promoter. The Tet-Off promoter is an example of an inducible mammalian promoter.

Examples of suitable yeast and fungal promoters are Leu2 promoter, the galactose (Gall or Ga17) promoter, alcohol dehydrogenase I (ADH1) promoter, glucoamylase (Gla) promoter, triose phosphate isomerase (TPI) promoter, translational elongation factor EF-I alpha (TEF2) promoter, glyceraldehyde-3-phosphate dehydrogenase (gpdA) promoter, or glutamate dehydrogenase (gdhA) promoter. An example of a strong ubiquitous promoter for expression in plants is cauliflower mosaic virus (CaMV) 35S promoter.

The nucleic acid construct according to the invention is preferably a vector, in particular a plasmid, cosmid or phage or nucleotide sequence, linear or circular, of a single or double stranded DNA or RNA, derived from any source, in which a number of nucleotide sequences have been joined or recombined into a unique construction which is capable of introducing any one of the nucleotide sequences of the invention in sense or antisense orientation into a cell. The choice of vector is dependent on the recombinant procedures followed and the host cell used. The vector may be an autonomously replicating vector or may replicate together with the chromosome into which it has been integrated. Preferably, the vector contains a selection marker. Useful markers are dependent on the host cell of choice and are well known to persons skilled in the art.

The nucleic acid construct can further optionally comprise other regulating elements known in the art that are suitable in said method. These include, but are not limited to, elements present in the 5' UTR, 3' UTR and coding nucleotide sequences of homologous and/or heterologous nucleotide sequences, including the Iron Responsive Element (IRE), Translational cis-Regulatory Element (TLRE) or uORFs in 5' UTRs and poly(U) stretches in 3' UTRs. Preferably, said regulatory elements are operably linked to the nucleotide sequences and promoters according to the invention.

A recombinant host cell, such as a mammalian, including human (optionally, following EP patenting rules, with the exception of human embryonic stem), plant, animal, insect, fungal or bacterial cell, containing one or more copies of a nucleic acid construct according to the invention is an additional subject of the invention. By host cell is meant a cell which contains a nucleic acid construct such as a vector and supports the replication and/or expression of the nucleic acid construct. Examples of suitable bacteria are Gram positive bacteria such as several species of the genera *Bacillus, Streptomyces* and *Staphylococcus* or Gram negative bacteria such as several species of the genera *Escherichia* and *Pseudomonas*. Fungal cells include yeast cells. Expression in yeast can be achieved by using yeast strains such as *Pichia pastoris, Saccharomyces cerevisiae* and *Hansenula* polymorphs. Other fungal cells of interest include filamentous fungi cells as *Aspergillus niger, Trichoderma reesei*, and the like. Furthermore, insect cells such as cells from *Drosophila* and Sf9 can be used as host cells. Alternatively, a suitable expression system can be a baculovirus system or expression systems using mammalian cells such as CHO, COS, CPK (porcine kidney), MDCK, BHK, and Vero cells. A suitable human cell or human cell line is an astrocyte, adipocyte, chondrocyte, endothelial, epithelial, fibroblast, hair, keratinocyte, melanocyte, osteoblast, skeletal muscle, smooth muscle, stem, synoviocyte cell or cell line. Examples of suitable human cell lines also include HEK 293 (human embryonic kidney), HeLa, Per.C6, CAP (cell lines derived from primary human amniocytes), and Bowes melanoma cells. Following EP patentability rules, in an embodiment, a human cell is not an embryonic stem cell.

Therefore, another aspect of the invention relates to a host cell that is genetically modified, preferably by a method of the invention, in that a host cell comprises a nucleic acid construct as herein defined above. For transformation procedures in plants, suitable bacteria include *Agrobacterium tumefaciens* and *Agrobacterium rhizogenes*.

A nucleic acid construct preferably is stably maintained, either as a autonomously replicating element, or, more preferably, the nucleic acid construct is integrated into the host cell's genome, in which case the construct is usually integrated at random positions in the host cell's genome, for instance by non-homologuous recombination. Stably transformed host cells are produced by known methods. The term stable transformation refers to exposing cells to methods to transfer and incorporate foreign DNA into their genome. These methods include, but are not limited to transfer of purified DNA via microparticle bombardment, electroporation of protoplasts and microinjection or use of silicon fibers to facilitate penetration and transfer of DNA into the host cell.

Alternatively, a protein or polypeptide of interest may be expressed in a host cell, e.g., a mammalian cell, relying on transient expression from vectors.

A nucleic acid construct according to the invention preferably also comprises a marker gene which can provide selection or screening capability in a treated host cell. Selectable markers are generally preferred for host transformation events, but are not available for all host cells. A nucleic acid construct disclosed herein can also include a nucleic acid sequence encoding a marker product. A marker product can be used to determine if the construct or portion thereof has been delivered to the cell and once delivered is being expressed. Examples of marker genes include, but are not limited to the *E. coli* lacZ gene, which encodes β-galactosidase, and a gene encoding the green fluorescent protein.

Examples of suitable selectable markers for mammalian cells include, but are not limited to dihydrofolate reductase (DHFR), thymidine kinase, neomycin, neomycin analog G418, hydromycin, and puromycin.

Other suitable selectable markers include, but are not limited to antibiotic, metabolic, auxotrophic or herbicide resistant genes which, when inserted in a host cell in culture, would confer on those cells the ability to withstand exposure to an antibiotic. Metabolic or auxotrophic marker genes enable transformed cells to synthesize an essential component, usually an amino acid, which allows the cells to grow on media that lack this component. Another type of marker gene is one that can be screened by histochemical or biochemical assay, even though the gene cannot be selected for. A suitable marker gene found useful in such host cell transformation experience is a luciferase gene. Luciferase catalyzes the oxidation of luciferin, resulting in the production of oxyluciferin and light. Thus, the use of a luciferase gene provides a convenient assay for the detection of the expression of introduced DNA in host cells by histochemical analysis of the cells. In an example of a transformation process, a nucleic acid sequence sought to be expressed in a host cell could be coupled in tandem with the luciferase gene. The tandem construct could be transformed into host cells, and the resulting host cells could be analyzed for expression of the luciferase enzyme. An advantage of this marker is the non-destructive procedure of application of the substrate and the subsequent detection.

When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. Two non-limiting examples are CHO DHFR- cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin. Other useful markers are dependent on the host cell of choice and are well known to persons skilled in the art.

When a transformed host cell is obtained with a method according to the invention (see below), a host tissue may be regenerated from said transformed cell in a suitable medium, which optionally may contain antibiotics or biocides known in the art for the selection of transformed cells.

Resulting transformed host tissues are preferably identified by means of selection using a selection marker gene as present on a nucleic acid construct as defined herein.

Method for Expressing a Protein of Interest in a Cell or Organism, and Cells or Organisms Thus Obtained In an aspect, the present invention is concerned with a method for expressing a protein of interest in a cell or organism, said organism not being a human, said method comprising the steps of: a) providing a nucleic acid construct comprising: i) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence; ii) a first nucleotide sequence that comprises: a TC-rich nucleotide sequence comprising at least 8 consecutive C or T nucleotides, at least 3 A-rich nucleotide sequences comprising at least 5 consecutive A nucleotides, and a GT-rich nucleotide sequence comprising at least 10 nucleotides, at least 80% of which are G or T nucleotides, said first nucleotide sequence not comprising a GAA repeat nucleotide sequence; iii) a first nucleotide sequence that comprises: a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, said first nucleotide sequence not comprising a GAA repeat nucleotide sequence; iv) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence; or v) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, wherein said GAA repeat nucleotide sequence is located 3' of any one or more of said TC-rich nucleotide sequence, A-rich nucleotide sequences, and/or GT-rich nucleotide sequence; operably linked to a second nucleotide sequence encoding a protein or polypeptide of interest, and further operably linked to a promoter, b) contacting a cell with said nucleic acid construct to obtain a transformed cell, and c) allowing said transformed cell to express the protein or polypeptide of interest, for example, by subjecting said transformed cell to conditions leading to expression of the protein or polypeptide of interest, and optionally recovering said protein or polypeptide.

In a preferred embodiment of the method according to the invention a nucleic acid construct as defined above is used. The method of the invention may be an in vitro or ex vivo method. The method of the invention may be applied on a cell culture, organism culture, or tissue culture. The method of the invention may be performed on cultured cells.

The skilled person is capable of transforming cells in accordance with step b). Transformation methods as used in step b) include, but are not limited to transfer of purified DNA via microparticle bombardment, electroporation of protoplasts and microinjection or use of silicon fibers to facilitate penetration and transfer of DNA into the host cell.

In step c) the transformed cell is allowed to express the protein or polypeptide of interest, and optionally said protein or polypeptide is subsequently recovered. For example, the transformed cell may be subjected to conditions leading to expression of the protein or polypeptide of interest. The person skilled in the art is well aware of techniques to be used for expressing or overexpressing the protein or polypeptide of interest. Methods in which the transformed cell does not need to be subjected to specific conditions leading to expression of the protein or polypeptide of interest, but in which the protein or polypeptide of interest is automatically (e.g., constitutively) expressed, are also included in the method of the present invention.

Recovering steps depend on the expressed protein or polypeptide and the host cell used but can comprise isolation of the protein or polypeptide. When applied to a protein/polypeptide, the term "isolation" indicates that the protein is found in a condition other than its native environment. In a preferred form, the isolated protein is substantially free of other proteins, particularly other homologous proteins. It is preferred to provide the protein in a greater than 40% pure form, more preferably greater than 60% pure form. Even more preferably it is preferred to provide the protein in a highly purified form, i.e., greater than 80% pure, more preferably greater than 95% pure, and even more preferably greater than 99% pure, as determined by SDS-PAGE. If desired, the second nucleotide sequence may be ligated to a heterologous nucleotide sequence to encode a fusion protein to facilitate protein purification and protein detection on for instance Western blot and in an ELISA. Suitable heterologous sequences include, but are not limited to, the nucleotide sequences encoding for proteins such as for instance glutathione-S-transferase, maltose binding protein, metal-binding polyhistidine, green fluorescent protein, luciferase and beta-galactosidase. The protein may also be coupled to non-peptide carriers, tags or labels that facilitate tracing of the protein, both in vivo and in vitro, and allow for the identification and quantification of binding of the protein to substrates. Such labels, tags or carriers are well-known in the art and include, but are not limited to, biotin, radioactive labels and fluorescent labels.

In another aspect, the present invention pertains to a method for expressing a protein of interest in an organism, said organism not being a human, comprising the steps of: a) providing a nucleic acid construct comprising: i) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, ii) a first nucleotide sequence that comprises: a TC-rich nucleotide sequence comprising at least 8 consecutive C or T nucleotides, at least 3 A-rich nucleotide sequences comprising at least 5 consecutive A nucleotides, and a GT-rich nucleotide sequence comprising at least 10 nucleotides, at least 80% of which are G or T nucleotides, said first nucleotide sequence not comprising a GAA repeat nucleotide sequence, iii) a first nucleotide sequence that comprises: a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, said first nucleotide sequence not comprising a GAA repeat nucleotide sequence, iv) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence, or v) a first nucleotide sequence that comprises: a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, wherein said GAA repeat nucleotide sequence is located 3' of any one or more of said TC-rich nucleotide sequence, A-rich nucleotide sequences, and/or GT-rich nucleotide sequence; operably linked to a second nucleotide sequence encoding a protein or polypeptide of interest and further operably linked to a promoter, b) contacting a target cell and/or target tissue of an organism, said organism not being a human, with said nucleic acid construct to obtain a transformed target cell and/or transformed target tissue, c) optionally, allowing said transformed target cell to develop into a transformed organism, and d) allowing said transformed organism to express the protein or polypeptide of interest, for example, subjecting said transformed organism to conditions leading to expression of the protein or polypeptide of interest, and optionally recovering said protein or polypeptide.

The target cell may be an embryonal target cell, e.g., embryonic stem cell, for example, derived from a non-human mammalian, such as bovine, porcine, etcetera species. Preferably, said target cell is not a human embryonic stem cell. In the case of a multicellular fungus, such target cell may be a fungal cell that can be proliferated into said multicellular fungus. When a transformed plant tissue or plant cell (e. g., pieces of leaf, stem segments, roots, but also protoplasts or plant cells cultivated by suspension) is obtained with the method according to the invention, whole plants can be regenerated from said transformed tissue or cell in a suitable medium, which optionally may contain antibiotics or biocides known in the art for the selection of transformed cells. Furthermore, a part of the invention is a non-human transformed organism. Said organism is transformed with a nucleic acid sequence, chimeric gene, nucleic acid construct, or vector according to the present invention, and is capable of producing the polypeptide of interest. This includes a non-human transgenic organism, such as a transgenic non-human mammalian, transgenic plant (including propagation, harvest and tissue material of said transgenic plant, including, but not limited to, leafs, roots, shoots and flowers), multicellular fungus, and the like.

USES OF THE PRESENT INVENTION

It was found that the nucleotide sequences of the present invention increased integration of a nucleic acid construct comprising such nucleotide sequence into the genome of a host cell that was transformed, resulting in integration with multiple copies of said nucleotide sequence. This had a further mRNA usage-enhancing effect.

Thus, the invention is also directed to use of the nucleotide sequences of the present invention for increasing integration of a nucleic acid construct comprising said nucleotide sequence into a genome of a host cell.

Preferably, said nucleotide sequence is operably linked to a second nucleotide sequence encoding a protein or polypeptide of interest, and further operably linked to a promoter.

Thus, in an aspect, the present invention relates to use of a nucleotide sequence a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, and an intron sequence comprising at least splice sites required for splicing of the intron sequence, and optionally, a GAA repeat nucleotide sequence, in a nucleic acid construct for increasing integration of said nucleic acid construct into a genome.

It was further found that incorporation of the nucleotide sequences of the present invention into a nucleic acid construct, said nucleotide sequences not being operably linked to a nucleotide sequence encoding a protein or polypeptide of interest, and expression of said nucleic acid construct in a recombinant host cell, enhanced translation of a recombinantly expressed polypeptide (said polypeptide being expressed from a separate nucleic acid construct).

Thus, in a further aspect, the present invention is concerned with use of a nucleotide sequence having at least about 50, 55, 60, 65, 70, 75, 80, 85, 90, 95, 96, 97, 98, 99, or 100% sequence identity or at least 50, 55, 60, 65, 70, 75, 80, 85, 90, 95, 96, 97, 98, 99, or 100% sequence identity to any one of SEQ ID NOS: 1-39, or a nucleotide sequence as defined above, said nucleotide sequence being operably linked to a promoter but not to a second nucleotide sequence encoding a protein or polypeptide, for enhancing translation of a recombinantly expressed polypeptide.

In yet another aspect, the present invention relates to use of a nucleotide sequence having at least about 50% sequence identity or at least 50% sequence identity or at least 55, 60, 65, 70, 75, 80, 85, 90, 95, 96, 97, 98, 99, or 100% sequence identity to any one of SEQ ID NOS: 1-39, or a nucleotide sequence according to the present invention, for increasing the number of transformants upon transformation of a eukaryotic cell with a nucleic acid construct comprising a nucleotide sequence according to the present invention.

It is to be noted that the nucleotide sequences of the present invention may be located 3' of the second nucleotide sequence encoding a protein or polypeptide of interest. In this case, the nucleotide sequences of the present invention are not operably linked to a promoter sequence, and yet they may still have a translation-enhancing effect. Thus incorporating a GAA repeat nucleotide sequence into the 3'UTR of a nucleic acid construct further comprising a nucleotide sequence encoding a protein or polypeptide of interest also results in enhanced mRNA usage.

In yet another aspect, the present invention deals with use of a 3'untranslated region comprising a GAA repeat nucleotide sequence for enhancing mRNA usage and/or translation of a recombinantly expressed polypeptide. In an embodiment, said 3'untranslated region comprising a GAA repeat nucleotide sequence is present in a nucleic acid construct, which nucleic acid construct further comprises a 5'untranslated region lacking a GAA repeat nucleotide sequence and a translated nucleic acid sequence encoding a polypeptide of interest. Thus, in such aspect, the present invention relates to a nucleic acid construct comprising a 3'untranslated region comprising a GAA repeat nucleotide sequence, a 5'untranslated region lacking a GAA repeat nucleotide sequence, and a coding nucleic acid sequence encoding a polypeptide of interest.

The invention will be explained in more detail in the following Examples section, with reference to the appended figures. The examples serve for illustration purposes only, and do not intend to limit the present invention in any way.

FIGURES

The invention is exemplified using the appended figures, wherein

Figure 2:
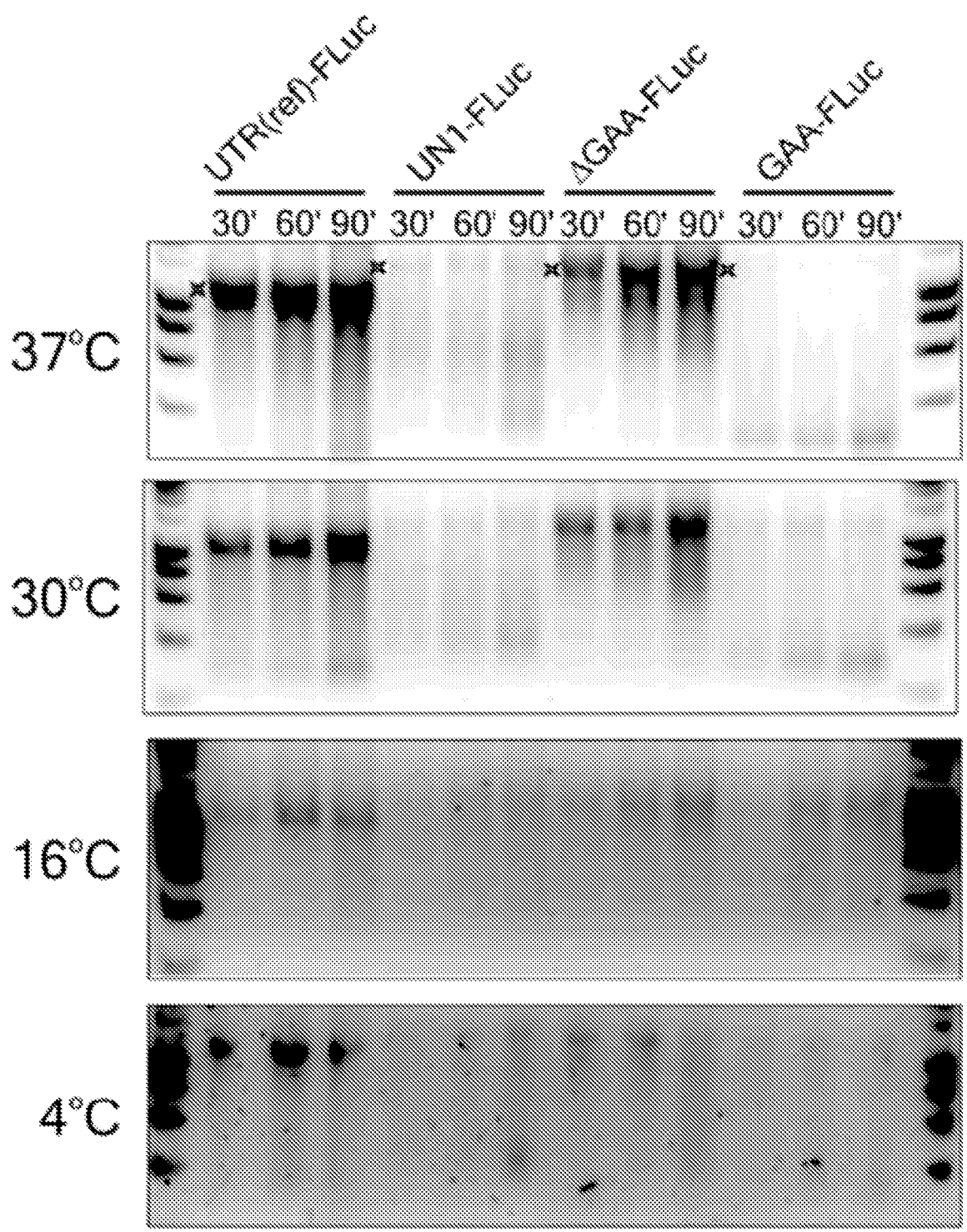
Figure 3:

FIG. 1 shows the results of translation competition using 5' capped forms of UTRREF-fluc and UTRREF-rluc mRNAs. (A) Fluc mRNA, with varying 5'UTR sequences was fixed at 10 nM final concentration, whereas competing rluc mRNA was added at increasing concentrations. This results in the increment of RLuc product (B) at the expense of FLuc (C). (D) Merger of panel B and C into one graph and plotted onto a logarithmic x-axis; closed circles: RLuc; open circles: FLuc; open squares: sum of RLuc and FLuc products. Error bars denote the averages of two independent experiments;

FIG. 2 shows the in vitro transcription mRNA yield of different DNA templates at various temperatures. Full length RNA products are highlighted with an asterisk. Smearing at the bottom of the gel is indicative of premature polymerase drop off; and FIG. 3 shows a schematic representation of pPNic174 cloning. GAL1-p: GAL1 promoter, T-CYC: Cyc1 terminator, GAL1-ds: GAL1 downstream region.

EXAMPLES

Example 1. Translational Advantage of Imperfect GAA Repeat in Mammalian Cell Extract Introduction The UN1 transcript has been shown to be pivotal for boosting protein synthesis and functions as a potent translational enhancer when coupled to other open reading frames (Hulzink et al., 2002). In vitro translation assays are powerful tools for evaluating mRNAs in translation. Generally, translation extracts that have not been treated with nucleases are considered to mimic in vivo translation reactions more closely compared to the nuclease-treated extracts (Soto et al., 2007). Others have modified the nuclease-treated translation system in order to mimic 'true' translation. Svitkin and colleagues (Svitkin et al., 2009), for instance, found that adding general RNA binding proteins to rabbit reticulocyte lysate (RRL) diminishes aberrant translation initiation and renders translation cap-dependent. Bottom line is that translation extracts do not represent a competitive environment needed for recapitulating the effect of (subtle) mRNA modifications on translation. The present inventors have developed a competitive in vitro translation assay that reproduces the in vivo translation-enhancing effect of the ntp303 5'UTR as was shown by Hulzink et al. (Hulzink et al., 2002).

Experimental

Template Preparation and Preparative In Vitro Transcription

PCR fragments were used as DNA templates. As PCR templates appropriate plasmids were used described in Hulzink et al., 2002 with following primer pairs: UN1-FLuc: PN012 (5'-CGAGGGCCCtaatacgactcactataG-GAAGCTCTAGCAG GAAGAAGAAATAA GAAGAAGAAGAAGAAGAAGAAGAAGCG-3', bacterial T7 promoter is lower case) and PN008 (5'-TCAGGCTGCGCAACTGTTGGGAAGGGCG-3'); ΔGAA-FLuc: PN014 (5'-TCGAGGGCCCtaatacgactcac-tataGGCGTCTCCTCTT CTTCTTGT-GAGAGTAAAAAATAAAACTCCC-3') and PN008 (see above); GAA-FLuc: PN012 and PN008 (see above).

PCR fragments were purified from agarose gel. For the synthesis of 5'-capped T7 transcripts, the T7 RiboMAX transcription kit (Promega) was used. The reaction was as described before (Barends et al., 2004). Non-modified RNA transcripts were obtained as described by supplier (Promega). Reference FLuc RNA was synthesized on the linear control FLuc DNA provided with the transcription kit. After 3 hrs of incubation, the reaction was terminated by the addition of RNAse-free DNAse. Transcripts were purified by phenol extraction and chromatography using a Micro Bio-Spin (P-30) column (Bio-Rad, Hercules, Calif.). The latter step was repeated once. The integrity of the RNAs was checked by agarose gel electrophoresis. The sequences of the 5'UTRs are summarized in Table 1.

In Vitro Translation

Translation experiments were performed in a 10-μl final volume of rabbit reticulocyte lysate (RRL) or wheat-germ extract (WGE), both from Promega. Standard conditions as described in supplied protocols were applied: Translation reactions were stopped in the linear phase of the reaction (30 min) by adding 10 volumes of Tris-buffered saline. RLuc and FLuc protein products were measured in a Victor reader (Perkin Elmer) using the Dual-Luciferase Reporter Assay System (Promega).

Results

FLuc transcripts that harbor the UN1 were tested in standard in vitro translation reactions using RRL and WGE. The UN1 was performing equally well or slightly better as compared to the reference fluc mRNA, in both eukaryotic translation extracts. In attempts to reveal their full potency, mRNAs were translated under the following challenging conditions: (I) elevated temperatures, (II) different mRNA concentrations, (III) initiation-factor depletion (by means of cap-analog titration), (IV) combinations of 5'cap and 3'poly (A) modifications of the mRNAs, (V) increased salt concentration, (VI) supplementing translation reactions with germinating pollen extracts, (VII) combinations with different 3'UTRs. However, none of the parameters described above resulted in a clear translational advantage of the 5'UTR as seen in vivo (data not shown).

Competitive Translation Set-Up in Nuclease-Treated RRL

We developed a competitive translation reaction using the common nuclease-treated RRL where translation potencies of 5'UTRs or any other regulating element can be measured and described in terms of relative competitiveness. This translation set-up supports translation stimulation by the cap structure (see below) and—albeit less pronounced—by poly (A) tailing of the mRNAs (not shown).

In the translation-competition set-up, a fixed concentration of fluc mRNA was allowed to compete with increasing concentrations of rluc competitor mRNA. The fluc mRNAs were generated to carry different 5'UTRs, whereas the rluc mRNA was prepared with only the reference UTR, UTR-REF (see FIG. 1A). RRL translation mixtures consist of approximately 20 nM ribosomes (not shown) and we found that for rluc and fluc mRNAs described here 10 nM is saturating. Therefore, 10 nM of the different fluc mRNAs was used in the translation reaction, competing with 0, 1, 3, 10, 30 and 100 nM of rluc mRNA. Translation reactions were performed in duplicate in 96-well plates, and from each reaction two aliquots were taken and measured. FLuc protein level measured at 10 nM fluc mRNA in the absence of rluc mRNA is maximal and was set at 1.00. RLuc expression level from reactions containing only 100 nM rluc mRNA was set at 1.00.

FIG. 1 shows the results of translation competition using 5' capped forms of UTRREF-fluc and UTRREF-rluc mRNAs. Relative FLuc levels decrease upon addition of increasing concentrations of UTRREF-rluc mRNA, resulting in an increment of RLuc product (FIGS. 1B and 1C). When both graphs are merged and plotted on logarithmic X-axis, linear fits can be calculated (FIG. 1D). If the experimental set up allows calculation of the competitive equilibrium, one would expect that the linearly fitted lines cross at 10 nM UTRREF-rluc mRNA (equimolar to the fixed concentration of UTRREF-fluc mRNA).

| | | |
|---|---|---|
| FLuc linear fit: | y = −0.34x + 089 | ($R^2$ = 1.00) |
| RLuc linear fit: | y = 0.27x + 0.24 | ($R^2$ = 0.91) |
| Equilibrium point: | 0.61x = 0.65 So x = 1.1 | |

The value of 1.1 corresponds to log 11. Apparently, 11 nM of UTRREF-rluc mRNA is needed for establishing competitive equilibrium with 10 nM UTRREF-fluc mRNA. One important aspect of establishing a competitive situation under saturating conditions is that total protein synthesis does not change. Indeed, there is no significant change in the total of synthesized protein (squares in FIG. 1D). This experimental set-up also shows that coding regions of fluc and rluc mRNAs are comparable in terms of ribosomal initiation, elongation and termination efficiencies. This allows a straight-forward screen and analysis of different regulatory sequences. We did not establish this competitive translation set-up in WGE, since even at 300 nM of either fluc or rluc mRNA, translation was still not saturating. Most likely, WGE contains a higher concentration of (active) ribosomes.

Cap Dependency

To further evaluate the competitive translation set-up, UTRREF-fluc and UN1-fluc mRNAs were tested in both 5' capped and non-modified forms. As competitor, capped UTRREF-rluc mRNA was used (see FIG. 2). At 14 nM of capped UTRREF-rluc mRNA competitive equilibrium is reached with 10 nM of capped UTRREF-fluc (Table 2). Non-capped UTRREF-fluc has a considerably lower equilibrium point (4 nM of capped UTRREF-rluc mRNA is required to compete with 10 nM of non-capped UTRREF-fluc mRNA for ribosomes). When the same experiment was repeated with non-capped UTRREF-rluc competitor mRNA, equilibrium point was restored to 12 nM (data not shown). This shows that in the competitive translation set up the cap structure has a positive effect on translation.

In parallel, capped and non-capped ntp303-fluc mRNAs were tested. More than 500 nM of UTRREF-rluc mRNA was needed to obtain a competitive equilibrium with 10 nM of ntp303-fluc mRNA, over a 50-fold excess (Table 2). Apparently, the UN1 is a translation enhancer, and competes heavily for the translation machinery. This competitive potential of the UN1 is completely cap-dependant, since non-capped version of UN1-fluc mRNAs completely abrogated the enhancing effect. The competitive potential of the UN1 is very similar to the data published on in vivo translation enhancement. In transient protein expression experiments using growing pollen tubes, Hulzink and colleagues found that the UN1 establishes a 50-fold enhancement in RLuc expression compared to an efficient reference 5'UTR (Hulzink et al., 2002).

GAA Repeat is a Translation Enhancer

The UN1 is of common length and nucleotide composition and no particular structural features are present. Two hairpin structures (HP1 and HP2) are separated by a single-stranded spacer (SS1) and just upstream of the AUG translational start codon, another stretch of single-stranded nucleotides is present (Hulzink et al., 2002). One striking feature of HP1 is that it contains an imperfect GAA repeat, $(GAA)_3ATAA(GAA)_8$. Deletion of the repeat region completely abolishes the translational potential of the 5'UTR: competitive equilibrium dropped over 30-fold to levels comparable to those of UTRREF (see Table 2). When only the $(GAA)_3ATAA(GAA)_8$ sequence was used as 5'UTR, over 1500 nM of competitor mRNA was needed in order to reach translational equilibrium with 10 nM GAA-fluc mRNA. As for the UN1, the translational enhancing mechanism of the GAA repeat involves the 5' cap structure (see Table 2). Again, data presented here closely resemble those obtained from the in vivo expression experiment (Hulzink et al., 2002). There, UN1 deprived of the $(GAA)_8$ part of the repeat had a translation efficiency comparable to the reference construct, almost a 50-fold drop compared to intact UN1.

Conclusion

A new tool is presented for assessing the effect of regulatory RNA sequences on translation by means of a competitive translation system. Using this approach we reproduced the translation-enhancing effect of the plant ntp303 5'UTR found in transient in vivo experiments. GAA repeat sequences have been reported to function as enhancers of intron splicing (Yeakley et al., 1996) but no role of GAA repeats in translation enhancement has been described. It was now found that GAA trinucleotide repeat sequence enhances protein synthesis by stimulating ribosomal protein synthesis. How the GAA repeat enhances translation is not clear, but is most likely to function during translation initiation. Fascinatingly, this mechanism is possibly evolutionary conserved since the enhancing effect found in plants is recapitulated by rabbit reticulocyte lysate.

TABLE 1

Sequences of the translation-enhancing elements in this study

| | |
|---|---|
| Ref | GGAATACAAGCTTATGCATGCGGCCGCATCTAGAGGGCCCGG ATCCAA |
| UN1 | GGAAGCTCTAGCAGGAAGAAGAAATAAGAAGAAGAAGAAGAA GAAGAAGAAGCGTCTCCTCTTCTTCTTGTGAGAGTAAAAAAT AAAACTCCCAAAAAAAAGAAAATCATCAAAAAAACAAATTTC AAAAAGAGTTTTTGTGTTTGGGGATTAAAGAATAAAAAAACA ACGTC |
| GAA | GGAAGAAGAAATAAGAAGAAGAAGAAGAAGAAGAAGAAGCGC C |
| ΔGAA | GGCGTCTCCTCTTCTTCTTGTGAGAGTAAAAAATAAAACTCC CAAAAAAAAGAAAATCATCAAAAAAACAAATTTCAAAAAGAG TTTTTGTGTTTGGGGATTAAAGAATAAAAAAACAACGTC |

TABLE 2

Competitive equilibriums measured for the different 5'translation-enhancing elements (herein also referred to as "5'UTRs")

| mRNA[1] | 5' cap structure | Competitive equilibrium |
|---|---|---|
| UTR$_{ref}$-fluc | + | 1.4 ± 0.4 |
| | − | 0.4 ± 0.0 |
| UN1-fluc | + | 53 ± 13 |
| | − | 0.7 ± 0.0 |
| ΔGAA-fluc[4] | + | 1.6 ± 0.8 |
| | − | ND[3] |
| GAA-fluc[5] | + | 160 ± 17[2] |
| | − | 3.9 ± 0.0 |

[1]RLuc mRNAs were tested at 10 nM final concentration, whereas competitor FLuc mRNA was added at 0, 1, 3, 10, 30 and 100 nM final concentration.
[2]These numbers were extrapolated from graphs such as shown in FIG. 1.
[3]ND: not determined.
[4]ΔGAA 5'UTR encompasses nts 52-173 of the ntp303 sequence, whereas
[5]GAA 5'UTR covers nts 14-51 of the ntp303 5'UTR sequence (see FIG 1).

Example 2. Improved Monoclonal Antibody Yield and mRNA Formation in Mammalian Cell Cultures by UN1 Adaptation Summary Two modified UN sequences, denoted as UN2a and UN2b, were designed for enhanced protein expression relative to the UN1. Vectors for expression of heavy and light chain antibody subunits, harboring a UCOE™ transcriptional enhancer element, were equipped with the three UN elements. CHO suspension cells were transfected as duplicates with these plasmids and stable pools were selected for each transfection. The pools transfected with UN2a and UN2b constructs produced 3.5-4 times more antibody than the UN1 cell pools. The pools contained similar copy numbers, but light and heavy chain mRNA levels were also elevated in the UN2a and UN2b pools. We conclude that the presence of the UN2a and UN2b elements results in increased transcription and/or mRNA half-life as compared to UN1 sequences.

Introduction

CHO suspension (CHO-S) cells are commonly used for production of biopharmaceuticals, including monoclonal antibodies (mAbs). These mAbs are usually produced in stable transfection pools or in single cell lines selected from these pools. Vectors for protein expression are often equipped with an element that enhances transcription, such as the immediate-early enhancer (IE) which is commonly used in combination with the human Cytomegalovirus (CMV) promoter element (Boshart et al., 1985), and a universal chromatin opening element (UCOE™) (Benton et al., 2002). We equipped mAb expression vectors harboring a UCOE™ element and IE-CMV promoter with either a UN1 for enhanced expression, or a modified UN element (UN2a or UN2b) designed to further enhance protein expression. Here we show that stable CHO-S cell pools with a UN2a and UN2b sequence produce 3.5-4 times more antibody than UN1 pools.

Experimental

Vector Construction

UN2a and UN2b and UN1 were cloned into the CET 1019 HS-puro Cabilly Chimera heavy and light chain expression vectors (Ye et al., 2010, Mann et al., 2008) using a one step plan. The UNic™ sequences (UN1, UN2a and UN2b) were ordered as synthetic DNAs (Biobasic Inc Toronto, Canada) consisting the full sequence of the UN flanked with the promoter sequence and a part of the antibody chain sequence. Thus each synthetic DNA spanned the unique NdeI site of the CMV promoter and the UNic™ sequence till the 5' to EcoRV site of the unaltered heavy or light chain sequence. The desired sequences were introduced in the starting plasmids by exchanging them via Nde I and EcoRV digestion and ligation. All plasmids digested as expected and were DNAs were sequence verified by Agencount Bioscience Corporation. These data showed that the sequences of all vectors were identical to those expected and indicated below.

Transfection

Vector DNA was linearized, purified by phenol chloroform extraction and ethanol precipitation. The amount of DNA was determined by Fluorometry. Digested DNA was checked for linearity by agarose gel electrophoresis. $1.2 \times 10^7$ CHO-S cells were transfected with 24 ug of light chain and 24 ug of heavy chain DNA using DMRIEC as per manufacturer's directions (Invitrogen). The transfection efficiency in these experiments was approximately 30%. Three replicate transfections were executed on three different days. A total of 4 different transfections (Table 3) were performed in triplicate.

Stable Pool Selection 48 hours post-transfection, cells were collected and placed under puromycin selection with 10 ug/mL puromycin. Every 2 or 3 days thereafter cells were collected, counted, viability determined and seeded into fresh selection medium. All cells were reseeded into fresh medium until cells recovered from selection. Mock-transfected cells did not survive selection and contained less than 5% viable cells after 5 days of selection. Cells transfected on all days exhibited a standard pattern of killing (viability decreased to 5-40%) following the addition of puromycin and a pattern of recovery (all cell viabilities were greater than 95% by day 17 post-transfection). Research cell banks of all 9 stable cell pools were prepared. The remaining cells were passed in selection medium for 1 week. The products of these pools were used for all the analyses described below.

Preparation of Exhaust Titers

The 9 stable pools were seeded in duplicate shaker flasks containing $2 \times 10^5$ cells/ml viable cells in 25 ml of selection medium. After 7 and 10 days post-seed, a 1 mL sample of the culture was removed and tested for cell number and cell viability. The 1 mL sample of each culture was clarified by centrifugation and analyzed for MAb titer by ELISA. The capture antibody used to this ELISA was against the heavy chain and the detection antibody has specificity for both heavy and light chains. Each ELISA was processed in triplicate. An average of all three readings was calculated and errors representing standard deviation of the three measurements determined.

IgG1 Titers of Stable Pools

The supernatants of stable pool exhaust cultures derived from transfection with UN1 vectors produce an average of 44 µg/ml mab for the six cultures assayed. The data stem from 6 supernatants for the independent duplicate titer determinations of the three separately prepared stable pools per UN. By contrast, exhaust culture supernatants of stable pools obtained from transfection with UN2a and UN2b-containing vectors yielded an average of 157 and 186 µg/ml MAb, respectively. The relative expression yields are summarized in Table 4.

These results support the notion that UN2a and UN2b promote greater gene expression when added to the 5'UTR of heavy and light chain constructs. On average, UN2a and UN2b elements produce 3.5-4× as much antibody as UN1.

mRNA Accumulation

To determine whether differences in protein expression are related to differences in mRNA level, we analyzed total cellular mRNA for light and heavy chain specific mRNA. Taqman gene expression assays were developed for human kappa and IgG1 constant regions. These assays use an RNA purification protocol from Qiagen and the high capacity Reverse transcription protocol from Applied Biosciences followed by a standard Taqman assay. (Note: These assays have been used to detect 2-fold differences of concentration in test RNA standards). We derived RNA from two of the three sets of stable pools produced in these studies. The level of heavy and light chain mRNA detected in pools from UN1 cells was used as a standard. The relative differences detected in stably-transfected cells with each UN, averaged over the two sets (Table 4), show that there is 2-3× as much heavy chain mRNA in stable pools with UN2a and UN2b, as compared to UN1. A more substantial increase of light chain mRNA was observed in stable pools with a UN2a (5×) and UN2a and UN2b (17×) in the light chain expression vector.

Gene Copy Number Determination

The three cell pools (UN1, UN2a and UN2b) were analyzed on their gene copy number (Cogenics). The copy numbers of heavy and light chain genes in the UN1 pool were not altered in comparison to the UN1 pool (Table 2). The copy numbers in the UN2b pool were altered by less than 35 percent. Thus, UN1, UN2a and UN2b all result in a similar number of gene copies integrated in the into the genome.

Conclusions

The presence of UN2a and UN2b enhances antibody production 3.5-4-fold when positioned in the 5'UTR (Table 2). This enhancement is likely due in part to the increased mRNA level (Table 2). However, the increased mRNA level is not caused by an altered gene copy number. Thus, the UN2a and UN2b sequences result in increased transcription and/or increased mRNA half-life as compared to UN1 sequences.

TABLE 3

Transfection samples

| Heavy chain | Light chain |
| --- | --- |
| Construct 1 (UN2a HC) | Construct 2 (UN2a LC) |
| Construct 3 (UN2b HC) | Construct 4 (UN2b LC) |
| Construct 5 (UN1 HC) | Construct 6 (UN1 LC) |
| Mock | Mock |

TABLE 4

Protein expression, mRNA levels and copy numbers

| | UN2a | | UN2b | |
| --- | --- | --- | --- | --- |
| | HC | LC | HC | LC |
| MAb production in stable transgenic pools[1] | 3.5 ± 0.2 | | 4.2 ± 0.4 | |
| mRNA concentration in MAb expressing pool, relative to UN1 | 2.6 ± 0.7 | 5.5 ± 0.5 | 2.7 ± 1.3 | 17 ± 4.1 |
| Average number of genome integrated LC or HC copies in stable pools, relative to UN1 | 1.2 | 0.9 | 0.7 | 1.4 |

[1]Average yield, relative to UN1, on duplicate titer determinations of 3 independently generated transgenic pools for each monoclonal expression vector pair. Protein yield was determined by ELISA Sequences HindIII (AAGCTT) site has been underlined. Character in bold indicates transcription start site.

UN1
AGATCACTAG<u>AAGCTT</u>CAAGCTCTAGCAGGAAGAAGAAATAAGAAGAAGA

AGAAGAAGAAGAAGAAGCGTCTCCTCTTCTTCTTGTGAGAGTAAAAAATA

AAACTCCCAAAAAAAGAAAATCATCAAAAAAACAAATTTCAAAAAGAGT

TTTTGTGTTTGGGGATTAAAGAATAAAAAAAACAACGCC

UN2a
AGATCACTAG<u>AAGCTT</u>CAAGCTCTAGCAGGAAGAAGAAATAAGAAGAAGA

AGAAGAAGAAGAAGAAGCGTCTCCTCTTCTTCTTGTGAGAGTAAAAAATA

AAACTCCCAAAAAAAGAAAATCATCAAAAAAACAAATTTCAAAAAGAGT

TTTTGTGTTTGGGGATTAAAGAATAAAAAAAACAACAGGTGAGTAAGCGC

AGTTGTCGTCTCTTGCGGTGCCGTTGCTGGTTCTCACACCTTTTAGGTCT

GTTCTCGTCTTCCGTTCTGACTCTCTCTTTTTCGTTGCAGGCC

UN2b
AGATCACTAG<u>AAGCTT</u>CAAGCTCTAGCAGGAAGAAGAAAGAAGAAGAAGA

AGAAGAAGAAGAAGAAGCGTCTCCTCTTCTTCTTGTGAGAGTAAAAAAGA

AAACTCCCAAAAAAAGAAAATCATCAAAAAAACAAATTTCAAAAAGAGT

TTTTGTGTTTGGGGATTAAAGAAGAAAAAAAACAACAGGTGAGTAAGCGC

AGTTGTCGTCTCTTGCGGTGCCGTTGCTGGTTCTCACACCTTTTAGGTCT

GTTCTCGTCTTCCGTTCTGACTCTCTCTTTTTCGTTGCAGGCC

Example 3. In Vitro Transcription

Summary

The role of GAA sequences on protein regulation was investigated. Data show that specific GAA-harboring DNA sequences inhibit in vitro transcription.

Introduction

GAA repeat sequences have been reported to function as enhancers of intron splicing (Yeakley et al., 1996). In humans, GAA repeats can cause Friedreich's ataxia (Babcock et al., 1997; Gibson et al., 1996; Campuzano et al., 1996; Baralle et al., 2008), a mitochondrial dysfunction especially affecting neuron and heart-muscle. In both cases the GAA repeat sequences affect nuclear events such as transcription and splicing (Grabczyk and Usdin, 2000a; Grabczyk and Usdin, 2000b; Sakamoto et al., 2001; Wells, 2008). In the case of Friedreich's ataxia, transcription of the nuclear-encoded frataxin gene is troubled as a direct consequence of GAA repeat duplication. Here we compared the transcription yield of reference and GAA-repeat modified DNA.

Experimental

Analytical In Vitro Transcription

In vitro run-off T7 transcription was performed according to protocol from Promega [Product Manual, RiboMAX™ Large Scale RNA Production Systems—SP6 and T7] on the PCR products described earlier [Example 1]. Standard transcription reactions were placed at 4° C., 16° C., 30° C. and 37° C. At 30', 60' and 120' 2-µl samples were harvested and mixed with 3 volumes of denaturing loading dye and heated for 10' at 65° C. Samples were then separated on a 1% agarose gel and visualized using SYBR-safe and BioRad.

Result

The yield of full-length product for most mRNAs was higher at higher incubation temperature (see FIG. 2). Ref RNA showed a gradually increasing signal in time, of which the vast majority (>90%) of the RNA signal migrated at the position of the full-length product, irrespective of the incubation temperature. UN1-Fluc showed a very low yield of full-length product. This yield depended on the temperature and was 10%-20% of the total RNA production. ΔGAA-Fluc had a significantly ameliorated signal (80%-90% of the total RNA transcribed). The GAA-Fluc template exhibited the lowest transcription yield.

Conclusion

Thus, the absence of the GAA-rich region increased the mRNA yield 5 to 8 fold. Also the GAA-FLuc RNA synthesis pattern showed that the transcriptional yield of UN1-FLuc is dictated by the GAA-rich region. The yields of full-length GAA-FLuc and UN1-FLuc improved when the reaction temperature was lowered to 16° C. This effect has been shown earlier (Krieg P A. 1990).

Example 4. UN Development in *A. niger*

Summary

Constructs containing UN variants and a laccase gene were used to transform *A. niger*. The transformants resulting from random integration of these constructs were subjected to high-throughput screening by micro-culturing experiments for increased secreted laccase. Individual clones producing more laccase compared to reference clones were obtained. Also, for some variants more active clones with UN technology were found.

Experimental

Constructs

Laccase expressing plasmids containing UN variants were constructed by incorporating the expression cassette consisting of the glucoamylase (gla) promoter and 5'UTR (AY250996), the enzyme coding sequence (see below), and the TrpC terminator (Cullen et al., 1987) in a bacterial kanamycin antibiotic resistance vector using PyrA (X96734.2) as the *A. niger* selection marker (Goosen et al., 1987)). The Gla promoter contains an EcoRI site which was used for UTR-sequence exchange. Thus the 5'UTR of glucoamylase was exchanged by UN1 and linked to the coding sequence of laccase (lcc-1, acc code: NT 166518) by a NcoI site. In subsequent experiments the UN1 sequence of this plasmid (pPNic153) was replaced by UN variants (Tables 7 and 8). The new constructs were sequence verified.

Protoplast Formation and Transformation

Spores were inoculated at $10^6$ spores/ml in 250 ml transformation medium (1×MMS, 1× Vishniac solution, 5 µM uridine, 0.1 M glucose) and grown overnight. Mycelium was harvested, washed in SMC buffer (1.33 M sorbitol, 20 mM MES pH=5.8, 50 mM $CaCl_2$), and protoplasts were generated in SMC buffer containing 250 mg/10 ml glucanex (Sigma) under gentle agitation at 30° C. Protoplast formation was followed microscopically in time. Protoplasts were washed three times (at 800 g) in STC buffer (1.33 M sorbitol, 10 mM Tris-HCl pH=7.5, 50 mM $CaCl_2$) and finally resuspended in the same buffer to a final concentration of $7.6×10^6$ protoplasts/ml. Transformation of $7.6×10^5$ protoplasts (in 200 µl, and otherwise the volume was adjusted to 200 µl with STC buffer), was performed by mixing them with 5 µg plasmid DNA and 50 µl PEG solution (25% (w/v) PEG-6000, 10 mM Tris-HCl [pH 7.5], 50 mM $CaCl_2$) and incubation on ice. After 20 min, 2 ml PEG solution was added and incubated for another 5 min at room temperature. Finally 4 mL STC solution was added, and 2 mL of the transformation mixture was added to 25 mL of selective transformation top agar (1× MMS, 1× Vishniac solution, 1× vitamin solution, 0.95 M sucrose, 0.6% agar; pre-incubated at 45° C.), and poured on 80 ml selective transformation medium (i.e. top agar containing 1.2% agar) in 15-cm plates. After sporulation clones were streaked out on selective multiwell 24-plates (1 clone/well) and grown at 30° C. till sporulation (5-10 days). Then the plates were placed at 4° C. until use. In order to preserve spores, spores were isolated using sterile cotton swabs in STC buffer containing 20% glycerol, transferred to cryovials and stored at −20° C.

Transformant Analysis

A high-throughput screening approach was used in which multiple clones can be grown in deep-well (microtiter-plate) format in multiple, parallel assays: Microtiter plates (1.2 ml square-well storage plate, Thermo Scientific, AB-1127) containing 0.4 ml complete medium (1×MMS, 1× Vishniac solution, 1× vitamin solution, 0.5% (w/v) yeast extract, 0.2% (w/v) casamino acids) with 50 mM xylose as carbon source were inoculated with $2.10^6$ spores per ml and sealed with gas-permeable adhesive seals (Thermo Scientific, AB-01718) and grown at 30° C. at 1000 rpm in a microtron (Infors HT, Switserland). After 22 hrs of growth, mycelium was pelleted by centrifugation at 2000 g and washed once with 800 ul induction medium (complete medium containing 10 mM maltose and 50 mM sorbitol). Mycelium was finally resuspended in 0.8 ml induction medium and incubated as described above. Laccase was determined after 23 h incubation. A laccase assay was developed for the detection of secreted laccase: 100 µl supernatant was mixed with an equal volume of a 200 mM NaAc, pH 5.0 solution containing a 0.02 volume of ABTS solution (prepared as described by supplier, Sigma). The enzymatic conversion of ABTS was determined by measuring the absorbance at 405 nm after incubating the reaction mixture in the dark.

Results

Clones showing laccase expression were collected. For UN1, UN2-AGAA and UN2-ΔGAA-cc 56, 36 and 81, respectively, transformants were obtained. During four microtron experiments, clones were monitored for growth performance and assayed for secreted laccase activity and total secreted proteins in triplicate assays. Laccase expression data, corrected for total secreted protein levels, indicated that clones containing pPNic181 (UN2-AGAA) exhibit a reproducible, increased laccase expression (Table 5). The highest laccase expressing clone containing pPNic181 (UN2-AGAR) showed a ten times higher yield laccase as compared to the background yield: Only a few clones showed increased laccase expression, but the increase was three times the level of UN1.

Clones containing pPNic182 (UN2-ΔGAA-cc) also had an increased laccase yield. Moreover, the relationship between the number of expressing clones and the yield of those transformants indicated that due to this UN2-ΔGAAcc more transformants become high-expressors.

In another experiment laccase yield measurement was used to determine the effect of moving the GAA imperfect repeat to the 3' direction of the UTR, to incorporate an extra transcription start and to change the GAA imperfect repeat into an CAA repeat sequence. These data indicate that minimizing the UTR structure, introducing an extra TATA sequence as well as replacing the GAA imperfect repeat for an CAA repeat sequence or moving that GAA rich sequence to the translation start increase the yield of the expressed laccase. Moreover, also a combination of these UN adaptations increases the yield (Table 6).

TABLE 5

Laccase yield by transformants with different UN variants

|  | Average | | | | Number of |
| --- | --- | --- | --- | --- | --- |
|  | All | Top 5 | Median | Max | transformants |
| UN1-153 | 0.45 | 0.70 | 0.43 | 1.00 | 12 |
| UN2-ΔGAA | 0.70 | 0.91 | 0.22 | 2.33 | 7 |
| UN2-ΔGAA-cc | 0.65 | 1.47 | 0.53 | 2.02 | 28 |

Activities represent averages of triplicate measurements in micro-culture format. All data relative to best yielding clone with UN1 (i.e. Max UN1 set to 1.0)

TABLE 6

Laccase yield by transformants with different UNvariants

|  | Average | | | | Number of |
| --- | --- | --- | --- | --- | --- |
|  | All | Top 5 | Median | Max | transformants |
| UN1 | 0.25 | 0.48 | 1.23 | 1.00 | 26 |
| UN1 minimal | 0.66 | 2.68 | 1.60 | 9.67 | 30 |
| UN1 shuffle | 0.29 | 0.72 | 1.48 | 1.54 | 30 |
| UN1 CAA Fl | 1.28 | 5.43 | 1.46 | 9.93 | 30 |
| UN1 min TATA CAA | 0.37 | 1.04 | 1.44 | 2.89 | 30 |

All data relative to best yielding clone with UN1 (i.e. Max UN1 set to 1.0)

TABLE 7

Translation-enhancing elements used in the study

| UN1-153 | CAAGCTCTAGCAGGAAGAAGAAATAAGAAGAAGAAGAAG<br>AAGAAGAAGAAGCGTCTCCTCTTCTTCTTGTGAGAGTAA<br>AAAATAAAACTCCCAAAAAAAAGAAAATCATCAAAAAAA<br>CAAATTTCAAAAAGAGTTTTTGTGTTTGGGGATTAAAGA<br>ATAAAAAAAACAACCTCCACC |
| --- | --- |
| UN2-<br>ΔGAA-181 | CGTCTCCTCTTCTTCTTGTGAGAGTAAAAAATAAAACTC<br>CCAAAAAAAAGAAAATCATCAAAAAAACAAATTTCAAAA<br>AGAGTTTTTGTGTTTGGGGATTAAAGAATAAAAAAAACA<br>ACCTCGTGCGTGTTGCCGATTCGCGTACGAATACGCCTT<br>GTGCTGACACTTCTGTAGCACC |
| UN2-<br>ΔGAA-cc-<br>182 | CGTCTCCTCTTCTTCTTGTGAGAGTAAAAAAGAAAACTC<br>CCAAAAAAAAGAAAATCATCAAAAAAACAAATTTCAAAA<br>AGAGTTTTTGTGTTTGGGGATTAAAGAAGAAAAAAAACA<br>ACCTCGTGCGTGTTGCCGATTCGCGTACGAATACGCCTT<br>GTGCTGACACTTCTGTAGCACC |

TABLE 8

Translation-enhancing elements used in the study

| UN1-218 | CAAGCTCTAGCAGGAAGAAGAAATAAGAAGAAGAAGAA<br>GAAGAAGAAGAAGCGTCTCCTCTTCTTCTTGTGAGAGT<br>AAAAAATAAAACTCCCAAAAAAAAGAAAATCATCAAAA<br>AAACAAATTTCAAAAAGAGTTTTTGTGTTTGGGGATTA<br>AAGAATAAAAAAAACAAGGCGGCCGCCCCCTTCACC |
| --- | --- |
| UN1-Min-<br>286 | CAACCTCTACCACCAACAACAAACAACAACAACAACAA<br>CAACAACAACAACCCTCTCCACATCTCCCTCTCAGAGT<br>AAAAAACAAAACTCCCAAAAAAAAGAAAATCATCAAAA<br>AAACAAATTTCAAAAAGACTTCTTCTCATTCCTTATTA<br>AAGAACAAAAAAAACAAGGCGGCCGCCCCCTTCACC |
| UN1-G11/<br>3-287 | CAAGCTCTAGCACGTCTCCTCTTCTTCTTGTGAGAGTA<br>AAAAATAAAACTCCCAAAAAAAAGAAAATCATCAAAAA<br>AACAAATTTCAAAAAGAGTTTTTGTGTTTGGGGATTAA<br>AGAATAAAAAAAACAAGGAAGAAGAAATAAGAAGAAGA<br>AGAAGAAGAAGAAGAAGGGCGGCCGCCCCCTTCACC |
| UN1-CAA-<br>288 | GTATTTTTACAACAATTACCAACAACAACAAACAACAA<br>ACAACATTACAATTACTATTTACAATTACAAGCGTCTC<br>CTCTTCTTCTTGTGAGAGTAAAAAATAAAACTCCCAAA<br>AAAAAGAAAATCATCAAAAAAACAAATTTCAAAAAGAG<br>TTTTTGTGTTTGGGGATTAAAGAATAAAAAAAACAAGG<br>CGGCCGCCCCCTTCACC |
| UN1-Min<br>TATA/<br>CAA-290 | CAAGCTCTACCACCAAGAACAAACAACAACAACATATA<br>TAAAACAACAACCACCATCTCCTCTTCTTCTTGTCAAC<br>TCCAAAATCAAACTCCCAAAAAAAAGCAAATCATCAAA<br>ACCACAAATTTCAAACAACAACAACAAACAACAAACAA<br>CATTAACATCATATCAAGGCGGCCGCCCCCTTCACC |

Example 5. The Effect of Different UNic™ Sequences on the Yield of Interleukin 8 Expression in Yeast Summary The effect of different UN sequences on the yield of interleukin 8 expression in yeast was measured. Data indicate that alterations in the UN sequence allow better yield.

Introduction

*S. cerevisiae* is a eukaryotic, single cellular model organism used in both research and industrial settings to produce (recombinant) proteins. We determined the single, targeted genomic integration of constructs, which encode human interleukin-8 (hIL8) as gene of interest (GeneID: 3576). This protein is naturally secreted from human leukocytes. The constructs used here integrate genomically at the GAL1 locus causing galactose deficient strains. This results in a situation where induction of the GAL1 promoter can be achieved by low levels of galactose in the medium, which can not be metabolized by the strain. This provides an advantage for production from these constructs in large-scale fermentations. The effect of different UN sequences was tested in this project. The effect on hIL8 expression in *S. cerevisiae* was determined by high throughput micro-culture screening of 48 clones per construct.

Experimental

Cloning and Transformation

The GAL promoter of plasmid pYES2 (Invitrogen) was modified by replacing the existing AgeI-HindIII sequence by a AgeI-HindIII fragment obtained by applying PCR on the pYES2 promoter using primers PN.272 and PN.273 (Table 1) The resulting sequence, Pgal-mod, is presented in Table 1. The 5'UTR- and the hIL8 sequence were introduced by replacing the HindIII-XbaI fragment of that plasmid in a triple ligation by two synthetic DNA fragments: the HindIII-EcoRV 5'UTR-SUC2 and the EcoRV-XbaI hIL8 sequence (Table 9).

A DNA fragment of the resulting plasmid was amplified by PCR using primers PN.307 and PN.308, digested with PvuII and NsiI, and ligated in vector YIplac211 (Gietz et al., 1988) after digestion with the same enzymes. The resulting plasmid was used as a template for amplification of the construct indicated in FIG. 3, using primers PN.307 and PN.316. The PCR fragment was ligated into a pCR4Blunt-TOPO vector according to the protocol supplied by the manufacturer (Invitrogen), resulting in construct pPNic174.

Plasmids pPNic175, pPNic176 and pPNic178 were constructed by replacing the 5'UTR of pPNic174 as a HindIII-EcoRV fragment of pPNic174 by a synthetic HindIII-EcoRV DNA fragment bearing UN1, UN1-cc or UN2-cc, respectively.

Next the GAA repeat was removed: Plasmids pPNic175, pPNic176 and pPNic178 were subjected to amplification by PCR using primers PN.345 and PN.346. The PCR products were digested with HindIII and XbaI and ligated into pPNic176 which was previously digested with the same enzymes. The resulting vectors bear a UN1-AGAR (pPNic198), a UN1ΔGAAcc (pPNic199), and a UN2ΔGAAcc (pPNic201), respectively (Table 10). The plasmids were sequence verified.

Transformation of S. cerevisiae strain W1588 was done as follows: O/N culture was diluted to an OD600 of 0.1 in 5 ml prewarmed YPD-medium and grow until OD600=0.5-2.0. Cells were collected by centrifugation, resuspended in 50 µl TE/LiAc (10 mM Tris-HCl [pH 8.0], 1 mM EDTA, 100 mM LiAc) and incubated for 15 minutes at 30° C. Then 50 µl cells, 25 µl of a 2 mg/ml solution of fish sperm ssDNA (prepared in TE buffer), 100 ng plasmid digested with PvuII, 300 µl TE/PEG/LiAc solution (TE/LiAc complemented with 40% PEG) were mixed and incubated at 30° C. without shaking. Transformation mixture was heat shocked at 42° C. for 30 minutes and then supplemented with sterile water up to 1 mL. Transformed cells were plated on YNB/-URA/2% glucose plates. All clones were transferred to 24 wells YNB/-URA/2% glucose plates and kept at 4° C. Cultures were maintained by weekly transferring to fresh plates.

Microtron Growth and Analysis

Yeast precultures were started with colonies from YNB-URA (2% glucose) plates. Cells of the colonies were whisked in 800 µl YPD medium in 96 wells microtron plates. Precultures were grown overnight, the $OD_{600}$ was measured of 10× diluted pre-cultures. Precultures were diluted to approximately $OD_{600}$=0.1 in a total volume of 800 µl YPD medium with 0.5% or 2% galactose added. (YPD contains 2% glucose). Cultures were grown for 24 h after which the $OD_{600}$ was measured of the 10× diluted cultures. The plates were centrifuged for 5 min at 2000 rpm and 400 µl supernatant was harvested. Care was taken to harvest supernatant without cell pellet, because this interferes with the ELISA assay. Supernatants were stored at 4° C. and assayed within a week. The hIL8 ELISA was performed according to the supplier protocol 1 (Product manual Biolegend, 2009).

Results and Discussion

Transformation of yeast cells with the four constructs provided 48 or more clones per construct in three rounds. Microtron growth was performed in four runs. All clones except a few (<5%) grew in the micro-titer plate cultures. The $OD_{600}$ of overnight pre-cultures was between 1.0 and 4.0. The clones that resulted in an $OD_{600}$ below 1.0 were considered 'not grown' and not tested for hIL8 expression. All pre-cultures were diluted to an $OD_{600}$ of 0.1 resulting in the production cultures. In the first three microtron runs, a total of 48'growing' clones containing each of the four constructs were tested. In these three runs 0.5% galactose was added to the medium of the production cultures at inoculation. The fourth microtron run consisted of a second culturing of 31 clones producing the highest amounts of hIL8 in the first runs. For this fourth run, cultures were started in both YPD/0.5% galactose and YPD/2% galactose. $OD_{600}$ of the production cultures after 24 h was between 2.5 and 5.0. All transformants were micro-cultured as described above and assayed for secreted hIL8. The amount of hIL8 present in the supernatant after 24 hours of micro-culturing in the presence of 0.5% galactose was calculated by comparison with standard hIL8, supplied with the ELISA assay kit. The combined results of three micro-culture runs, testing 48 clones per construct are shown in Table 11.

The variation in the expression profiles can be explained by a combination of single integration of the constructs at a relatively 'open' genomic location and infrequent multiple copy integrations, next to the most likely single integration at the GAL1 locus. Apparently the UN sequence influences the nature of genomic integration. The high expression events are most likely caused by a combination of the type of genomic integration and UN associated increase in protein production.

Galactose deficiency was tested on five high-producing and on several non-producing clones. Of all the tested clones approximately 50% showed the $GAL^+$ phenotype and approximately 50% a $GAL^-$ phenotype. This indicates that half of the clones have a construct integrated outside the GAL locus, i.e. located randomly or at the URA3 locus. A number of UN variants were screened in a micro-culture format, resulting in clear difference in the yield of secreted hIL8. Remarkably high producing clones were found for several UNs.

We explain the high expression profile observed for clones containing UN1ΔGAA, UN1ΔGAA-cc and UN2ΔGAA-cc by a UN associated increase in protein production. The highest h-IL8 expressor with an UN1ΔGAA is 1.7-fold higher than the highest UN1 clone.

TABLE 9

| Primer and expression cassette sequences | |
|---|---|
| PN.272 | CTCGTCTTCACCGGTCGCGTTC |
| PN.273 | CGTCGCAGCTAAGCTTTTTTGTTGATACTTTTATTACATTTGAATAAGAAGTAATACAA |
| PN.307 | GATATAATACAGCTGACGGATTAGAAGCCGCCGAG |
| PN.308 | CTTACTTGAGATGCATGCAAATTAAAGCCTTCGAGCGTCC |
| PN.345 | GCAGCGTCAGAAGCTTCGTCTCCTCTTCTTCTTGTGAGAG |
| PN.346 | CTTACTTGAGTCTAGATTATGAATTCTCAGCCCTCTTC |
| PN.316 | CAGCTGCATACAATCATTTATTAAGTAGTTGAAGCATGTATGAACTATAAAAGTGTTACTAGGCGTATCACGAGGCCAGC |
| Pgal1- AgeI - mod TSS | accggtCGCGTTCCTGAAACGCAGATGTGCCTCGCGCCGCACTGCTCCGAACAATAAAGATTCTACAATACTAGCTTTTATGGTTATGAAGAGGAAAAATTGGCAGTAACCTGGCCCCACAAACCTTCAAATGAACGAATCAAATTAACAACCATAGGATGATAATGCGATTAGTTTTTTAGCCTTATTTCTGGGGTAATTAATCAGCGAAGCGATGATTTTTGATCTATTAACAGATATATAAATGCAAAAACTGCATAACCACTTTAACTAATACTTTACAACATTTTCGGTTTGTATTACTTCTTATTCAAATGTAAT |

TABLE 9-continued

Primer and expression cassette sequences

| 5'UTR | TSS-HindIII Start codon | AAAGTATCAACAAAAaagcttGTTAATATACCTCT ATACTTTAACGTCAAGGAGAAAAAACTATA |
| --- | --- | --- |
| CDS (hIL8) | Start codon - EcoRV - XbaI | ATGATGCTTTTGCAAGCCTTCCTTTTCCTTTTGGC TGGTTTTGCAGCTAAgatatcTGCAGAAGGTGCAG TTTTGCCAAGGAGTGCTAAAGAACTTAGATGTCAG TGCATAAAGACATACTCCAAACCTTTCCACCCCAA ATTTATCAAAGAACTGAGAGTGATTGAGAGTGGAC CACACTGCGCCAACACAGAAATTATTGTAAAACTT TCTGATGGAAGAGAGCTCTGTCTGGACCCCAAGGA AAACTGGGTGCAGAGGGTTGTGGAGAAGTTTTTGA AGAGGGCTGAGAATTCATAAtctaga |

All sequences presented in 5' → 3' direction
Restriction sites in lower cast (AgeI: accggt; HindIII: aagctt; EcoRV; gatatc; XbaI: tctaga; Translation start in Italic

TABLE 10

UN sequences

| UN1 | AAAGTATCAACAAAAaagcttAGCAGGAAGAAGAAATAA GAAGAAGAAGAAGAAGAAGAAGAAGCGTCTCCTCTTCTT CTTGTGAGAGTAAAAAATAAAACTCCCAAAAAAAAGAAA ATCATCAAAAAAACAAATTTCAAAAAGAGTTTTTGTGTT TGGGGATTAAAGAATAAAAAAAACAACAAA |
| --- | --- |
| UN1 ΔGAA | AAAGTATCAACAAAAaagcttCGTCTCCTCTTCTTCTTG TGAGAGTAAAAAATAAAACTCCCAAAAAAAAGAAAATCA TCAAAAAAACAAATTTCAAAAAGAGTTTTTGTGTTTGGG GATTAAAGAATAAAAAAAACAACAAA |
| UN1 ΔGAAcc | AAAGTATCAACAAAAaagcttCGTCTCCTCTTCTTCTTG TGAGAGTAAAAAAGAAAACTCCCAAAAAAAAGAAAATCA TCAAAAAAACAAATTTCAAAAAGAGTTTTTGTGTTTGGG GATTAAAGAAGAAAAAAAACAACAAA |
| UN2 ΔGAAcc | AAAGTATCAACAAAAaagcttCGTCTCCTCTTCTTCTTG TGAGAGTAAAAAAGAAAACTCCCAAAAAAAAGAAAATCA TCAAAAAAACAAATTTCAAAAGAGTTTTTGTGTTTGTA AGTCAGGACTCTAGCTTTCTACTGTAGTATCCTCTAAAG GACTGCTGTTCTGTGCACCCCCTTCCTTTGTTTATCATA GCGCACGACAAGAGTACTAACTAATTAACTTAGGGGAT TAAAGAAGAAAAAAAACAACAAA |

TABLE 11 hIL8 yield by transformants with different UTR sequences

| | Average | | | | Number of |
| --- | --- | --- | --- | --- | --- |
| | All | Top 5 | Median | Max | transformants |
| UN1 | 12.1 | 63.4 | 5.0 | 207 | 40 |
| UN1ΔGAA | 40.0 | 204.1 | 15.1 | 358 | 45 |
| UN1ΔGAA-cc | 36.8 | 158.3 | 9.9 | 343 | 43 |
| UN2ΔGAA-cc | 15.9 | 75.6 | 6.15 | 185 | 42 |

Activities represent averages of triplicate measurements in micro-culture format. Micro-culture supernatant was assayed by ELISA for hIL8 (pg/ml).

Example 6. A Moved GAA Repeat Improves Expression in Plant Protoplasts

Summary

Tobacco protoplast transfection experiments were carried out. Comparison of the different UN designs indicate that a 3' moved GAA sequence in 3' direction results in an approximately 2-times higher expression of the reporter protein as compared to the reference UN1.

Introduction

Luciferase activity was measured after transfecting different batches of tobacco protoplasts by different batches of plasmid DNA using either multiwell plates or culture tubes.

A set of two constructs was used in these experiments. They contained an ntp303 promoter, a UN sequence, the firefly luciferase coding sequence, and the ntp303 3'UTR (Hulzink et al., 2002). The constructs differed only by the composition of the UN sequence (Table 12).

Experimental

Expression plasmids were created by replacing the XhoI-NcoI fragment of the "303 5'/303 3' luciferase (Luc+) reporter plasmid (Hulzink et al., 2002) by UN1 and R3 (Table 1). Both sequences were flanked by the same sequences containing XhoI and NcoI restriction sites and the 5' and 3' sites of the 5'UTR sequences, respectively. The 5' flanking sequence was 5'-ctcgagTAATACGACTCAC-TATAGG-3' (XhoI recognition site in lower cast); the 3' flanking sequence, here presented including the start codon, was 5'-CAccatgg-3' (NcoI in lower cast). The luciferase expression constructs were purified using the NucleoBond Xtra Midiprep kit (Macherey-Nagel) according to the instructions by the manufacturer. Two plasmid batches were made from every construct.

Tobacco leaf protoplasts were prepared as described by de Groot et al. (1992). Freshly prepared protoplasts were transfected using PEG according to the protocol by Locatelli et al. (2003). Transfections were performed in polypropylene culture tubes, using $0.25 \times 10^6$ protoplasts and 10 μg plasmid DNA per transfection.

Luciferase activity was measured using the steadylite plus reagent (PerkinElmer), according to the manufacturers protocol. Briefly, 50 μl of each protoplast sample was transferred to three wells of an OptiPlate-96 plate (PerkinElmer) and 50 μl steadylite plus reagent was added to each sample. The wells were mixed by pipetting and incubated for 10-15 min to allow complete cell lysis. Luminescence was measured using a Victor 3 plate reader (Perkin Elmer).

Results

Transfection of protoplast with the reference (UN1) construct resulted in luciferase expression that was 10 times more than the background signal measured in wells with non-transformed cells.

Luciferase activity was measured after repetitive transfection with two plasmid batches of each construct included in 4 independent transfection experiments. The average activity obtained from different batches and by different experimentators was calculated per construct for every experiment, and is presented relative to the UN1 sequence (Table 13). The average R3:UN1 ratio was 2.5, indicating that R3 samples gave more than 2-fold higher expression than UN1 samples.

Discussion

Repetitive transfection of tobacco protoplasts with two batches of UN1 and R3 luciferase constructs in two different protoplast batches, and by four different experimentators showed that results can be obtained reproducibly and accurately using the transfection method described here and a luciferase assay kit.

Transfer of the full imperfect GAA repeat (iGr) from the original position in the 5'-UTR (UN1) downstream to a position close to the start codon results in increased luciferase expression. This result indicates a position effect of the iGr and supports the hypothesis that iGr inhibits transcription when close to the transcription start site.

Conclusion

R3 enhances luciferase expression by a factor of two as compared to UN1.

TABLE 12

Sequence used in this study

| | |
|---|---|
| UN1 - 228 | CAAGCTCTAGCAGGAAGAAGAAATAAGAAGAAGAAGAAGA AGAAGAAGAAGCGTCTCCTCTTCTTCTTGTGAGAGTAAAA AATAAAACTCCCAAAAAAAAGAAAATCATCAAAAAAACAA ATTTCAAAAAGAGTTTTTGTGTTTGGGGATTAAAGAATAA AAAAAACAACCTC |
| R3 - 230 | CAAGCTCTAGCACGTCTCCTCTTCTTCTTGTGAGAGTAAA AAATAAAACTCCCAAAAAAAAGAAAATCATCAAAAAAACA AATTTCAAAAAGAGTTTTTGTGTTTGGGGATTAAAGAATA AAAAAAACAAGGAAGAAGAAATAAGAAGAAGAAGAAGAAG AAGAAGAAGCCTC |

TABLE 13

Relative luciferase yield in protoplasts transfected with either UN1 or R3 in four independent experiments

| Experiment | UN1 | R3 |
|---|---|---|
| 1 | 1.0 ± 0.4 | 2.7 ± 1.1 |
| 2 | 1.0 ± 0.4 | 1.9 ± 0.5 |
| 3 | 1.0 ± 0.2 | 2.2 ± 0.5 |
| 4 | 1.0 ± 0.1 | 2.2 ± 0.5 |

Data represent averaged R3:UN1 ratio's within one experiment and include different plasmid batches and experimentators.

Example 7. UN2 Enhances Secreted Alkaline Phosphatase and Human IL4 Yield in Cultured Mammalian Cells Summary CHO cell lines were transformed with a single copy of an expression cassette for SeAP or hIL-4. The cassettes contained either the UN1 sequence, or the UN2 sequence which contained an integrated intron sequence. The expression levels of both proteins were 4 times higher in the presence of UN2 as compared to the UN1 constructs. We conclude that UN2 has an improved enhancer functionality as compared to UN1.

Introduction

We modified the UN1 sequence to contain a tailored intron sequence. This UN with intron was integrated in expression vectors encoding secreted alkaline phosphatase (SeAP) or encoding cytokine IL-4. Vectors with the UN1 sequence were constructed as a reference. The vectors were used to generate polyclonal CHO cell lines by means of the Flp-In system (Invitrogen, Life Technologies, Carlsbad USA). For both proteins, the cell lines generated using the Flp-In system differ only by the UN sequence. This approach enables a good evaluation of the UN2 sequence relative to the UN1 sequence.

Experimental

Construction of SEAP and hIL-4 Expression Cassettes in Flp-in Vectors

The pPNic136, pPNic137, pPNic139, and pPNic140 vectors were constructed based on the SeAP expression vector pPNic004 [WO2009/154454]. The EF1-α promoter of pPNic004 was removed by digestion with Bgl II-HindIII and replaced by the 752 bp Bgl II-HindIII fragment derived from pRL-HL which contains the CMV promoter. The resulting plasmid was digested with HindIII-BamHI and ligated to synthetic HindIII-UN1-SeAP-BamHI and HindIII-UN2-seAP-BamHI DNA fragments (DNA2.0, Basel), respectively (Tables 15 and 16). The resulting SeAP expression vectors are pPNic136 and pPNic137, respectively. The SeAP gene and preceding 5'-UTR were removed from the pPNic136 vector by digesting with HindIII and BstBI and replaced by HindIII-UN1-hIL4-BstBI and HindIII-UN2-hIL4-BstBI fragments respectively. These fragments contained either a UN1 or a UN2 sequence fused to the hIL-4 gene and purchased as synthetic DNAs (DNA2.0, Basel). The resulting expression vectors are denoted to as pPNic139 and pPNic140, respectively. So the plasmids pPNic136 and pPNic139 both contain UN1, while the 5'-UTR sequences of pPNic137 and pPNic140 are both UN2. The plasmids were verified by sequencing.

Protein Expression

Transfection and Polyclonal Pool Generation

CHO Flp-In cells (Invitrogen) were seeded in 6-wells plates at a density of $3 \times 10^4$ cells per well in 2 ml HAM'S F12 medium supplemented with 10% FCS. The cells were 85-95% confluent at 24 hrs after seeding. Cells were transfected using FugeneHD reagent in the presence of one of the 4 Flp-In constructs (pPNic136, 137, 139, 140), and plasmid pOG44 (Invitrogen), which is the plasmid that encodes the Flp integrase enzyme that mediates the integration of the expression constructs into the genome of the Flp-In cell line. Every transfection was performed in triplicate wells. As a control, every expression plasmid was also transfected to a single well in the absence of pOG44.

At 24 hrs after transfection, cells were passed to new wells and Hygromycin B selection was applied after the cells had adhered. Cells were passed twice a week and kept at more than 5 percent confluency, except for control cells which were passed using the same dilution as the non-control cells. Selection was considered complete after the cells that were transfected in the presence of pOG44 were over 20 times more dense (confluent) than those transfected in the absence of pOG44. Cells from triplicate transformations of a single construct were combined in a single T25 culture flask.

SEAP Titers

Pooled Flp-In lines were seeded as duplicates at 90% confluency in 6-wells plates in 2 ml medium without Hygromycin B. Samples of the culture medium were taken at 24 hours after seeding and non-adherent cells were removed by centrifugation. Collected samples were stored frozen. Activity of the SeAP (secreted alkaline phosphatase) in the supernatant was determined in duplicate wells using a Tropix Phospha-Light™ System kit (Applied Biosystems) according to the protocol provided by the manufacturer, and a Victor plate reader (Perkin Elmer) set to measure chemiluminescence.

hIL-4 Titers

Pooled Flp-In lines were seeded as duplicates at 90% confluency in 6-wells plates in 2 ml medium without Hygromycin B. Samples of the culture medium were taken at 24 hours after seeding and non-adherent cells were removed by centrifugation. The titers of hIL-4 in the supernatant were determined using a commercial ELISA kit (eBioscience). Each sample was assayed in duplicate wells and a dilution series of rhIL-4 (eBioscience) was used as a standard. The colorimetric ELISA assay was measured using a Victor3 plate reader (Perkin Elmer).

Results

The Flp-In system was used to generate polyclonal cell lines with a single copy of a SeAP or hIL-4 expression cassette integrated at the same genomic locus. The SeAP and hIL-4 titers of the UN2 Flp-In cell lines were calculated relative to the UN1 (Table 14). The cell lines containing the UN2 sequence express approximately a 4-fold increased protein levels relative to the lines with UN1 sequences.

Conclusion

Cell lines that differ only by the 5'-UTR produce 4 times more of a recombinant protein, either SeAP or hIL-4, when the UN1 is replaced by the UN2 sequence presented here.

TABLE 14

Protein expression of UN2 cell lines relative to UN1

|  | SeAP | hIL-4 |
|---|---|---|
| UN1 | 1.0 ± 0.0 | 1.0 ± 0.1 |
| UN2 | 4.1 ± 0.1 | 3.9 ± 0.2 |

TABLE 15

Coding sequences

| seAP-BamHI | ATGCTGCTGCTGCTGCTGCTGCTGGGCCTGAGGCTACAGCT<br>CTCCCTGGGCATCATCCCAGTTGAGGAGGAGAACCCGGACT<br>TCTGGAACCGCGAGGCAGCCGAGGCCCTGGGTGCCGCCAAG<br>AAGCTGCAGCCTGCACAGACAGCCGCCAAGAACCTCATCAT<br>CTTCCTGGGCGATGGGATGGGGGTGTCTACGGTGACAGCTG<br>CCAggatcc |
|---|---|
| hIL4-BstBI | ATGGGTCTCACCTCCCAACTGCTTCCCCCTCTGTTCTTCCT<br>GCTAGCATGTGCCGGCAACTTTGTCCACGGACACAAGTGCG<br>ATATCACCTTACAGGAGATCATCAAAACTTTGAACAGCCTC<br>ACAGAGCAGAAGACTCTGTGCACCGAGTTGACCGTAACAGA<br>CATCTTTGCTGCCTCCAAGAACACAACTGAGAAGGAAACCT<br>TCTGCAGGGCTGCGACTGTGCTCCGGCAGTTCTACAGCCAC<br>CATGAGAAGGACACTCGCTGCCTGGGTGCGACTGCACAGCA<br>GTTCCACAGGCACAAGCAGCTGATCCGATTCCTGAAACGGC<br>TCGACAGGAACCTCTGGGGCCTGGCGGGCTTGAATTCCTGT<br>CCTGTGAAGGAAGCCAACCAGAGTACGTTGGAAAACTTCTT<br>GGAAAGGCTAAAGACGATCATGAGAGAGAAATATTCAAAGT<br>GTTCGAGCTGATAAttcgaa |

Restriction sites in lower case

TABLE 16

Nucleotide sequences under study

| UN1-M25 | CAAGCTCTAGCAGGAAGAAGAAATAAGAAGAAGAAGAAGAAG<br>AAGAAGAAGCGTCTCCTCTTCTTCTTGTGAGAGTAAAAATA<br>AAACTCCCAAAAAAAGAAAATCATCAAAAAAACAAATTTCA<br>AAAAGAGTTTTTGTGTTTGGGGATTAAAGAATAAAAAAAACA<br>ACGCC |
|---|---|
| UN2-M25 | CAAGCTCTAGCAGGAAGAAGAAATAAGAAGAAGAAGAAGAAG<br>AAGAAGAAGCGTCTCCTCTTCTTCTTGTGAGAGTAAAAATA<br>AAACTCCCAAAAAAAGAAAATCATCAAAAAAACAAATTTCA<br>AAAAGAGTTTTTGTGTTTGGGGATTAAAGAATAAAAAAAACA<br>GGTGAGTAAGCGCAGTTGTCGTCTCTTGCGGTGCCGTTGCTG<br>GTTCTCACACCTTTTAGGTCTGTTCTCGTCTTCCGTTCTGAC<br>TCTCTCTTTTTCGTTGCAGGCC |

Example 8. Enhanced Production of a Recombinant Protein Using Free UN1

Summary

Intracellular expression of free UN1-RNA results in selection of clones with enhanced production of a recombinant protein from a UN expression cassette.

Introduction

Transfection of CHO cells with an expression cassette containing UN results in enhanced protein titers of a recombinant protein. It was determined whether addition of a free UN1 (fUN) cassette, which produces UN transcript but not a translation product, results into clones with further improved protein titers.

Experimental

Vector Construction

The human IL-4 cDNA sequence (genbank: NM000589) was removed from plasmid pCMV6-XL5mod_IL4_NM_000589 (OriGene Technologies, Rockville Md.) after restriction with SacI and HindIII, and ligated into mammalian expression vector pCMV6-neo (OriGene Technologies) after restriction with the same enzymes. The UN1 sequence with bordering fragments of the CMV promoter and hIL-4 gene was PCR amplified. The SacI and NheI sites present in the CMV promoter and hIL-4 gene, respectively, were used to introduce the UN1 sequence in the hIL-4 expression vector. The resulting vector was pPNic126 (UN1).

The fUN sequence (Table 17), consisting of a CMV promoter, the UN1 sequence and the SV40 p(A) sequence was ligated into the BstZ17I-digested pPNic126 vector. The resulting expression vector was pPNic129 (UN1+fUN).

Antibody Labeling

A human IL-4 specific mouse monoclonal antibody (Abazyme) was labeled with DyLight 488 (Pierce), according to the manufacturers instructions. A spectrophotometer (Genesys 10uv scanning) was used to confirm proper labeling as concluded from the calculated degree of labeling (3.6 mol label/mol antibody).

Transfection

Serum-free adapted CHO-k1 cells were transfected with the Amaxa Nucleofector II. Duplicate transfections were performed, using 10E6 cells and 4 µg linearized plasmid DNA. After transfection, cells were seeded in T25 flasks.

Selection and Screening

At 24 hrs post transfection, cells were transferred to single black-well plates with semi-solid medium containing Neomycin (1 µg/ml) and the Dylight 488-labeled hIL-4 antibody (8 µg/ml). The highest producer lines were selected based on colony size and fluorescence using a ClonePixFL device. At 10 and 12 days after transfection, a total of at least 25 colonies per transfection were picked by the ClonePixFL. Selected cell lines were seeded in 96-wells plates in selective medium. One week after seeding six clones per construct were selected based on high fluorescence (ClonePixFL) and normal growth and appearance (96-wells plate). The selected clones were transferred to 24-wells plates, seeded at 2.0E4 viable cells per well (Guava ViaCount) in non-selective medium. At 48 hours after seeding, hIL-4 titers were determined by ELISA (eBioscience human IL-4 ELISA kit) and cells were counted (Guava ViaCount).

Results

Serum-free adapted CHO-k1 cells were stably transfected with two constructs for the expression of the human cytokine IL-4. Both expression vectors contained the UN1 translation enhancer element, but one vector contained an additional cassette to drive transcription of free (untranslated) UN1. A high-throughput ClonePixFL device was used to screen colonies for the highest IL-4 expression. The 6 clones per construct that performed best in the ClonePixFL selection and in growth characteristics in medium were transferred to 24-wells plates to determine hIL-4 titers (Table 18). The 3 best clones with fUN element (UN1+fUN) produced 150 to 500 percent of hIL-4 levels as compared to the best clone without fUN element (UN1).

Conclusion

The presence of a UNic™ element for production of free UN1 mRNA results in enhanced production of recombinant hIL-4 in stably transfected CHO-k1 cells. When grown under production conditions, the best clone with fUN produces up to 5 times more hIL-4 than the clone without fUN.

TABLE 17

| Nucleotide sequences under study | |
|---|---|
| fUN1 | GGCCGCAATAAAATATCTTTATTTTCATTACATCTGTGTGTT |
| | GGTTTTTTGTGTGAATCGATAGTACTAACATACGCTCTCCAT |

TABLE 17-continued

| Nucleotide sequences under study |
|---|
| CAAAACAAAACGAAACAAAACAAACTAGCAAAATAGGCTGTC |
| CCCAGTGCAAGTGCAGGTGCCAGAACATTTCTCTATCGATAG |
| GTACCGAGCTCGTTGACATTGATTATTGACTAGTTATTAATA |
| GTAATCAATTACGGGGTCATTAGTTCATAGCCCATATATGGA |
| GTTCCGCGTTACATAACTTACGGTAAATGGCCCGCCTGGCTG |
| ACCGCCCAACGACCCCCGCCCATTGACGTCAATAATGACGTA |
| TGTTCCCATAGTAACGCCAATAGGGACTTTCCATTGACGTCA |
| ATGGGTGGACTATTTACGGTAAACTGCCCACTTGGCAGTACA |
| TCAAGTGTATCATATGCCAAGTACGCCCCCTATTGACGTCAA |
| TGACGGTAAATGCCCGCCTGGCATTATGCCCAGTACATGAC |
| CTTATGGGACTTTCCTACTTGGCAGTACATCTACGTATTAGT |
| CATCGCTATTACCATGGTGATGCGGTTTTGGCAGTACATCAA |
| TGGGCGTGGATAGCGGTTTGACTCACGGGATTTCCAAGTCT |
| CCACCCCATTGACGTCAATGGGAGTTTGTTTTGGCACCAAAA |
| TCAACGGGACTTTCCAAAATGTCGTAACAACTCCGCCCCATT |
| GACGCAAATGGGCGGTAGGCGTGTACGGTGGGAGGTCTATAT |
| AAGCAGAGCTGGTTTAGTGAACCGTGGATCCCAAGCTCTAGC |
| AGGAAGAAGAAATAAGAAGAAGAAGAAGAAGAAGAAGAAGCG |
| TCTCCTCTTCTTCTTGTGAGAGTAAAAAATAAAACTCCCAAA |
| AAAAAGAAAATCATCAAAAAAACAAATTTCAAAAAGAGTTTT |
| TGTGTTTGGGGATTAAAGAATAAAAAAAACAACGTCCCTCTA |

TABLE 17-continued

| Nucleotide sequences under study |
|---|
| GAGTCGGGGCGGCCGGCCGCTTCGAGCAGACATGATAAGATA |
| CATTGATGAGTTTGGACAAACCACAACTAGAATGCAGTGAAA |
| AAAATGCTTTATTTGTGAAATTTGTGATGCTATTGCTTTATT |
| TGTAACCATTATAAGCTGCAATAAACAAGTTAACAACAACAA |
| TTGCATTCATTTTATGTTTCAGGTTCAGGGGGAGGTGTGGGA |
| GGTTTTTTAAAGCAAGTAAAACCTCTACAAATGTGGTAAAAT |
| CGATAAGGATCCG |

TABLE 18 hIL-4 titers

| | UN1 | | | | | | UN1 + fUN | | | | | |
|---|---|---|---|---|---|---|---|---|---|---|---|---|
| Clone Number | | | | | | | | | | | | |
| | 1 | 2 | 3 | 4 | 5 | 6 | 1 | 2 | 3 | 4 | 5 | 6 |
| Relative yield[1] | 1.0 | 0.36 | 0.27 | 0.13 | 0.09 | 0.05 | 4.8 | 3.7 | 1.6 | 0.32 | 0.06 | 0.03 |

[1]Data of best six of each construct after correction for cell numbers in the supernatant of stably transformed CHO-k1 cells, selected in a high-throughput screening program. The relative expression of UN1 clones is compared to those with an additional fUN element (UN1 + fUN).

REFERENCES

Babcock M, de Silva D, Oaks R, Davis-Kaplan S, Jiralerspong S, Montermini L, Pandolfo M, Kaplan J. 1997. Regulation of mitochondrial iron accumulation by Yfh1p, a putative homolog of frataxin. Science 276: 1709-1712.

Baralle M, Pastor T, Bussani E, Pagani F. 2008. Influence of Friedreich ataxia GAA noncoding repeat expansions on pre-mRNA processing. Am J Hum Genet 83: 77-88.

Barends S, Rudinger-Thirion J, Florentz C, Giege R, Pleij C W, Kraal B. 2004. tRNA-like structure regulates translation of Brome mosaic virus RNA. J Virol 78: 4003-4010.

Benton, T, Chen, T, McEntee M. Fox B, King D, Crombie R, Thomas T. C, Bebbington C, 2002 The use of UCOE vectors in combination with a preadapted serum free, suspension cell line allows for rapid production of large quantities of protein. Cytotechnology 38(1-3):43-46.

Boshart, M.; Weber, F.; Jahn, G.; Dorsch-Hasler, K.; Fleckenstein, B.; Schaffner, W. 1985 A very strong enhancer is located upstream of an immediate early gene of human cytomegalovirus. Cell 41(2):521-530.

Campuzano V, Montermini L, Molto M D, Pianese L, Cossee M, Cavalcanti F, Monros E, Rodius F, Duclos F, Monticelli A, et al. 1996. Friedreich's ataxia: autosomal recessive disease caused by an intronic GAA triplet repeat expansion. Science 271: 1423-1427.

Cullen et al., 1987: Gene 57:21-26

Gibson T J, Koonin E V, Musco G, Pastore A, Bork P. 1996. Friedreich's ataxia protein: phylogenetic evidence for mitochondrial dysfunction. Trends Neurosci 19: 465-468.

Gietz, D. and Sugino, A. New yeast-*Escherichia coli* shuttle vectors constructed with in vitro mutagenized yeast genes lacking six-base pair restriction sites. Gene 1988; 74:527-534.

Goosen T, Bloemheuvel G, Gysler C, de Bie D A, van den Broek H W, Swart K. Transformation of *Aspergillus niger* using the homologous orotidine-5'-phosphate-decarboxylase gene. Curr. Genet. 11: 499-503, 1987

Grabczyk E, Usdin K. 2000a. Alleviating transcript insufficiency caused by Friedreich's ataxia triplet repeats. Nucleic Acids Res 28: 4930-4937.

Grabczyk E, Usdin K. 2000b. The GAA*TTC triplet repeat expanded in Friedreich's ataxia impedes transcription elongation by T7 RNA polymerase in a length and supercoil dependent manner. Nucleic Acids Res 28: 2815-2822.

Groot M J A de, Offringa R, Does M P, Hooykaas P J, van den Elzen P J. Mechanisms of intermolecular homologous recombination in plants as studied with single- and double-stranded DNA molecules. Nucleic Acids Res. 20(11): 2785-2794 (1992).

Honda M, Kaneko S, Matsushita E, Kobayashi K, Abell G A, Lemon S M. Cell cycle regulation of hepatitis C virus internal ribosomal entry site-directed translation. Gastroenterology 118: 152-62, 2000.

Hulzink R J M, de Groot P F M, Croes A F, Quadvlieg W, Twell W, van Herpen M M A, Wullems G J. The 5'-untranslated region of the ntp303 gene strongly enhances translation during pollen tube growth, but not during pollen maturation. Plant Physiology 129:342-353 (2002).

Kim Mann, Anjali Verma, Joe Orlando, Ela Puchacz. 2008 Advanced Method of Cell Line Generation Using UCOE® Technology, Millipore Corporation, Bioprocess Division, Bedford, Mass., USA, https://www.millipore.com/techpublications/tech1/ucoe_poster Krieg P A. 1990. Improved synthesis of full-length RNA probe at reduced incubation temperatures. Nucleic Acids Res. 18: 6463.

Locatelli F, Vannini C, Magnani E, Coraggio I, Bracale M. Efficiency of transient transformation in tobacco protoplasts is independent of plasmid amount. Plant Cell Rep. 21: 865-71 (2003).

Pelham H R, Jackson R J. 1976. An efficient mRNA-dependent translation system from reticulocyte lysates. Eur J Biochem 67: 247-256.

Product Manual, Human IL-8 ELISA MAX™ Set Deluxe Protocol, BioLegend, 1 Jun. 2009.

Sakamoto N, Ohshima K, Montermini L, Pandolfo M, Wells R D. 2001. Sticky DNA, a self-associated complex formed at long GAA*TTC repeats in intron 1 of the frataxin gene, inhibits transcription. J Biol Chem 276: 27171-27177.

Soto R R, Ricci E P, Decimo D, Moncorge O, Ohlmann T. 2007. Back to basics: the untreated rabbit reticulocyte lysate as a competitive system to recapitulate cap-poly(A) synergy and the selective advantage of IRES-driven translation. Nucleic Acids Res 35: e121.

Svitkin Y V, Evdokimova V M, Brasey A, Pestova T V, Fantus D, Yanagiya A, Imataka H, Skabkin M A, Ovchinnikov L P, Merrick W C, et al. 2009. General RNA-binding proteins have a function in poly(A)-binding protein-dependent translation. EMBO J 28: 58-68.

Wells R D. 2008. DNA triplexes and Friedreich ataxia. FASEB J 22: 1625-1634.

Ye, J., Alvin, K., Latif, H., Hsu, A., Parikh, V., Markusen J. F. 2010 Cell Culture and Tissue Engineering. Rapid protein production using CHO stable transfection pools. Biotechnology Progress.

Yeakley J M, Morfin J P, Rosenfeld M G, Fu X D. 1996. A complex of nuclear proteins mediates SR protein binding to a purine-rich splicing enhancer. Proc Natl Acad Sci USA 93: 7582-7587.

The invention claimed is:

1. A nucleic acid molecule comprising a first nucleotide sequence which comprises from its 5' end to its 3' end:
   i) a TC-rich nucleotide sequence comprising at least 12 consecutive C or T nucleotides,
   ii) 4 A-rich nucleotide sequences comprising at least 5 consecutive A nucleotides,
   iii) a GT-rich nucleotide sequence comprising at least 12 nucleotides, all of which are G or T nucleotides, and
   iv) a GAA repeat nucleotide sequence comprising the structure $(GAA)_n$ wherein n is an integer of 6 or more, wherein the first nucleotide sequence has at least 90% sequence identity with SEQ ID NO:5.

2. A nucleic acid construct comprising a first nucleotide sequence according to claim 1, wherein said first nucleotide sequence is operably linked to a second nucleotide sequence encoding a protein or polypeptide of interest, and further operably linked to a promoter.

3. A host cell or a non-human organism transformed with a nucleic acid construct according to claim 2.

4. The host cell according to claim 3, being selected from the group consisting of an animal cell, plant cell, fungal cell, yeast cell and prokaryotic cell.

5. The organism according to claim 3, said organism being a plant.

6. The nucleic acid molecule according to claim 1, wherein the first nucleotide sequence has 100% sequence identity with SEQ ID NO: 5.

7. The nucleic acid molecule according to claim 1, wherein the first nucleotide sequence has 90% sequence identity with SEQ ID NO: 75.

8. The nucleic acid molecule according to claim 1, wherein the first nucleotide sequence has 100% sequence identity with SEQ ID NO: 75.

9. The nucleic acid molecule according to claim 1, further comprising an intron sequence comprising at least splice sites required for splicing of the intron sequence, wherein said intron sequence is at the 3'end of the first nucleotide sequence.

10. The nucleic acid molecule according to claim 9, wherein the intron sequence comprises the splice site GT at the 5' end of the nucleotide sequence of the intron, and the splice site AG at the 3' end of the nucleotide sequence of the intron.

11. The nucleic acid molecule according to claim 10, wherein the splice site AG is preceded by a TC-rich nucleotide sequence.

12. The nucleic acid molecule according to claim 11, wherein the intron sequence further comprises a branch site comprising the sequence (C/T)T(A/G)A(C/T), at the 5' side of the TC-rich nucleotide sequence.

13. The nucleic acid molecule according to claim 12, wherein the branch site comprises the nucleotide sequence CTGAC.

14. The nucleic acid molecule according to claim 9, wherein the intron sequence comprises a nucleotide sequence having at least 80% sequence identity with nucleotides 171-274 of SEQ ID NO: 7.

15. The nucleic acid molecule according to claim 14, wherein the first nucleotide sequence and the intron sequence together have at least 90% sequence identity with SEQ ID NO: 30.

16. A method for expressing a protein of interest in a cell or organism, said organism not being a human, said method comprising the steps of:
   a) providing a nucleic acid construct according to claim 2,
   b) contacting a cell with said nucleic acid construct to obtain a transformed cell, and
   c) allowing said transformed cell to express the protein or polypeptide of interest, and optionally recovering said protein or polypeptide.

17. The method according to claim 16, wherein the protein is expressed in an organism, said method further comprising the steps of:
   a) contacting a target cell and/or target tissue of said organism with said nucleic acid construct to obtain a transformed target cell and/or transformed target tissue and/or transformed organism, and
   b) optionally, allowing said transformed target cell and/or transformed target tissue to develop into a transformed organism, and
   c) allowing said transformed organism to express the protein or polypeptide of interest, and optionally recovering said protein or polypeptide.

18. The method according to claim 16, wherein the cell is selected from the group consisting of an animal cell, plant cell, fungal cell, yeast cell, and prokaryotic cell, or wherein the organism is selected from the group consisting of a non-human animal, and a plant.

* * * * *

SEQUENCE LISTING

```
<160> NUMBER OF SEQ ID NOS: 80

<210> SEQ ID NO 1
<211> LENGTH: 173
<212> TYPE: DNA
<213> ORGANISM: Nicotiana tabacum

<400> SEQUENCE: 1
caagctctag caggaagaag aaakaagaag aagaagaaga agaagaagaa gcgtctcctc      60
ttcttcttgt gagagtaaaa aakaaaactc ccaaaaaaaa kaaaatcatc aaaaaaacaa     120
atttcaaaaa gagtttttgt gtttggggat taaagaakaa aaaaaacaac gtc            173

<210> SEQ ID NO 2
<211> LENGTH: 274
<212> TYPE: DNA
<213> ORGANISM: Artificial sequence
<220> FEATURE:
<223> OTHER INFORMATION: Synthetic; UN2 polynucleotide

<400> SEQUENCE: 2
caagctctag caggaagaag aaakaagaag aagaagaaga agaagaagaa gcgtctcctc      60
ttcttcttgt gagagtaaaa aakaaaactc ccaaaaaaaa kaaaatcatc aaaaaaacaa     120
atttcaaaaa gagtttttgt gtttggggat taaagaakaa aaaaaacaac aggtgagtaa     180
gcgcagttgt cgtctcttgc ggtgccgttg ctggttctca cacctttag gtctgttctc      240 gtcttccgtt ctgactctct cttttcgtt gcag                                  274

<210> SEQ ID NO 3
```

<211> LENGTH: 123
<212> TYPE: DNA
<213> ORGANISM: Artificial sequence
<220> FEATURE:
<223> OTHER INFORMATION: Synthetic; UN1dGAA polynucleotide

<400> SEQUENCE: 3

```
ggcgtctcct cttcttcttg tgagagtaaa aaataaaact cccaaaaaaa akaaaatcat    60
caaaaaaaca aatttcaaaa agagttttttg tgtttgggga ttaaagaaka aaaaaacaac   120
gtc                                                                 123
```

<210> SEQ ID NO 4
<211> LENGTH: 257
<212> TYPE: DNA
<213> ORGANISM: Artificial sequence
<220> FEATURE:
<223> OTHER INFORMATION: Synthetic; UN2dGAA polynucleotide

<400> SEQUENCE: 4

```
aaagtatcaa caaaaaagct tcgtctcctc ttcttcttgt gagagtaaaa akaaaactc     60
ccaaaaaaaa kaaatcatc aaaaaaaca atttcaaaaa gagttttttgt gtttgtaagt   120
caggactcta gctttctact gtagtatcct ctaaggact gctgttctgt gcacccctt    180
cctttgttta tcatagcgca cgacaagagt actaactaat taacttaggg ggattaaaga   240
akaaaaaaaa caacaaa                                                 257
```

<210> SEQ ID NO 5
<211> LENGTH: 173
<212> TYPE: DNA
<213> ORGANISM: Artificial sequence
<220> FEATURE:
<223> OTHER INFORMATION: Synthetic; R3 polynucleotide

<400> SEQUENCE: 5

```
caagctctag cacgtctcct cttcttcttg tgagagtaaa aaakaaaact cccaaaaaaa    60
akaaaatcat caaaaaaaca aatttcaaaa agagttttttg tgtttgggga ttaaagaaka   120
aaaaaaacaa ggaagaagaa akaagaagaa gaagaagaag aagaagaagc ctc           173
```

<210> SEQ ID NO 6
<211> LENGTH: 384
<212> TYPE: DNA
<213> ORGANISM: Artificial sequence
<220> FEATURE:
<223> OTHER INFORMATION: Synthetic; fUN1 polynucleotide

<400> SEQUENCE: 6

```
caagctctag caggaagaag aaataagaag aagaagaaga agaagaagaa gcgtctcctc    60
ttcttcttgt gagagtaaaa aataaaactc ccaaaaaaaa gaaaatcatc aaaaaaacaa   120
atttcaaaaa gagttttttgt gtttgggggat taaagaataa aaaaaacaac gtctggacaa   180
accacaacta gaatgcagtg aaaaaaatgc tttatttgtg aaatttgtga tgctattgct   240
ttatttgtaa ccattataag ctgcaataaa caagttaaca acaacaattg cattcatttt   300
atgtttcagg ttcagggggga ggtgtgggag gttttttaaa gcaagtaaaa cctctacaaa   360
tgtggtaaaa tcgataagga tccg                                          384
```

<210> SEQ ID NO 7
<211> LENGTH: 277
<212> TYPE: DNA
<213> ORGANISM: Artificial sequence

```
<220> FEATURE:
<223> OTHER INFORMATION: Synthetic; UN2-2 polynucleotide

<400> SEQUENCE: 7
caagctctag caggaagaag aaakaagaag aagaagaaga agaagaagaa gcgtctcctc     60
ttcttcttgt gagagtaaaa aakaaaactc ccaaaaaaaa gaaaatcatc aaaaaaacaa    120
atttcaaaaa gagttttgt gtttggggat taaagaagaa aaaaaacaac aggtgagtaa    180
gcgcagttgt cgtctcttgc ggtgccgttg ctggttctca cacctttag gtctgttctc    240 gtcttccgtt ctgactctct cttttcgtt gcaggcc                              277

<210> SEQ ID NO 8
<211> LENGTH: 252
<212> TYPE: DNA
<213> ORGANISM: Artificial sequence
<220> FEATURE:
<223> OTHER INFORMATION: Synthetic; UN2-3 polynucleotide

<400> SEQUENCE: 8
aagctctagc aggaagaaga aakaagaaga agaagaagaa gaagaagaag cgtctcctct     60
tcttcttgtg agagtaaaaa akaaaactcc caaaaaaak aaaatcatca aaaaacaaa    120 tttcaaaaag agtaggtaag attatctctt cccaaaattg attactttt tattgaacaa    180 ttattaacca atcatggctt aacgaaaaac aggttttgtg tttggggatt aaagaakaaa    240
aaaaacaaaa ca                                                        252

<210> SEQ ID NO 9
<211> LENGTH: 254
<212> TYPE: DNA
<213> ORGANISM: Artificial sequence
<220> FEATURE:
<223> OTHER INFORMATION: Synthetic; UN2-4 polynucleotide

<400> SEQUENCE: 9
caagctctag caggaagaag aaakaagaag aagaagaaga agaagaagaa gcgtctcctc     60
ttcttcttgt gagagtaaaa aakaaaactc ccaaaaaaaa kaaaatcatc aaaaaaacaa    120
atttcaaaaa gagtaggtaa gattatctct tcccaaaatt gattactttt attattgaac    180
aattactaac atttcatggc ttaacgaaaa acaggttttg tgtttgggga ttaaagaaka    240
aaaaaaacaa aaca                                                      254

<210> SEQ ID NO 10
<211> LENGTH: 266
<212> TYPE: DNA
<213> ORGANISM: Artificial sequence
<220> FEATURE:
<223> OTHER INFORMATION: Synthetic; UN2-5 polynucleotide

<400> SEQUENCE: 10
caagctctag caggaagaag aaakaagaag aagaagaaga agaagaagaa gcgtctcctc     60
ttcttcttgt gagagtaaaa aakaaaactc ccaaaaaaaa kaaaatcatc aaaaaaacaa    120
atttcaaaaa gagtgaggta agattatcga tatttaaatt atttatttct tcttttccat    180 tttttggct aacattttcc atggttttat gatatcatgc aggtacgttt tgtgtttggg    240
gattaaagaa kaaaaaaaac aaaaca                                         266

<210> SEQ ID NO 11
<211> LENGTH: 266
<212> TYPE: DNA
```

<213> ORGANISM: Artificial sequence
<220> FEATURE:
<223> OTHER INFORMATION: Synthetic; UN2-6 polynucleotide

<400> SEQUENCE: 11

| | | | | | |
|---|---|---|---|---|---|
| caagctctag | caggaagaag | aaakaagaag | aagaagaaga | agaagaagaa | gcgtctcctc | 60 |
| ttcttcttgt | gagagtaaaa | aakaaaactc | ccaaaaaaaa | kaaaatcatc | aaaaaaacaa | 120 |
| atttcaaaaa | gagtgaggta | agattatcga | tatttaaatt | atttatttct | tcttttccat | 180 |
| tttttggct | aacatttcc | taggttttat | tatatctagc | aggtacgttt | tgtgtttggg | 240 |
| gattaaagaa | kaaaaaaaac | aaaaca | | | | 266 |

<210> SEQ ID NO 12
<211> LENGTH: 265
<212> TYPE: DNA
<213> ORGANISM: Artificial sequence
<220> FEATURE:
<223> OTHER INFORMATION: Synthetic; UN2-7 polynucleotide

<400> SEQUENCE: 12

| | | | | | |
|---|---|---|---|---|---|
| aagctctagc | aggaagaaga | aakaagaaga | agaagaagaa | gaagaagaag | cgtctcctct | 60 |
| tcttcttgtg | agagtaaaaa | akaaaactcc | caaaaaaak | aaaatcatca | aaaaaacaaa | 120 |
| tttcaaaaag | agtgaggtaa | gattatcgat | atttaaatta | tttatttctt | cttttccatt | 180 |
| tttttggcta | acattttcct | aggttttatt | atatctagca | ggtacgtttt | gtgtttgggg | 240 |
| attaaagaak | aaaaaaaaca | aaaca | | | | 265 |

<210> SEQ ID NO 13
<211> LENGTH: 266
<212> TYPE: DNA
<213> ORGANISM: Artificial sequence
<220> FEATURE:
<223> OTHER INFORMATION: Synthetic; UN2-8 polynucleotide

<400> SEQUENCE: 13

| | | | | | |
|---|---|---|---|---|---|
| caagctctag | caggaagaag | aaakaagaag | aagaagaaga | agaagaagaa | gcgtctcctc | 60 |
| ttcttcttgt | gagagtaaaa | aakaaaactc | ccaaaaaaaa | kaaaatcatc | aaaaaaacaa | 120 |
| atttcaaaaa | gagtgaggta | agattatcga | tatttaaatt | atttatttct | tcttttccat | 180 |
| tttttggct | aacatttcc | taggttttat | tatatctagc | aggtacgttt | tgtgtttggg | 240 |
| gattaaagaa | kaaaaaaaac | aaaacc | | | | 266 |

<210> SEQ ID NO 14
<211> LENGTH: 287
<212> TYPE: DNA
<213> ORGANISM: Artificial sequence
<220> FEATURE:
<223> OTHER INFORMATION: Synthetic; UN2-9 polynucleotide

<400> SEQUENCE: 14

| | | | | | |
|---|---|---|---|---|---|
| caagctctag | caggaagaag | aaakaagaag | aagaagaaga | agaagaagaa | gcgtctcctc | 60 |
| ttcttcttgt | gagagtaaaa | aakaaaactc | ccaaaaaaaa | kaaaatcatc | aaaaaaacaa | 120 |
| atttcaaaaa | gagtttttgt | gtttgtaagt | caggactcta | gctttctact | gtagtatcct | 180 |
| ctaaaggact | gctgttctgt | gcacccctt | cctttgttta | tcatagcgca | cgacaagagt | 240 |
| actaactaat | taacttaggg | ggattaaaga | akaaaaaaaa | caacaaa | | 287 |

<210> SEQ ID NO 15
<211> LENGTH: 251

```
<212> TYPE: DNA
<213> ORGANISM: Artificial sequence
<220> FEATURE:
<223> OTHER INFORMATION: Synthetic; UN2-10 polynucleotide

<400> SEQUENCE: 15
caagctctag caggaagaag aaakaagaag aagaagaaga agaagaagaa gcgtctcctc      60
ttcttcttgt gagagtaaaa aakaaaactc ccaaaaaaaa kaaatcatc aaaaaaacaa     120 atttcaaaaa gagttttgt gtttgggtaa gtaattgcct tactcggaaa ataatcaatc     180
atcatactaa cgcaagaggc gctgatattg cggttataca gggattaaag aakaaaaaaa    240
acaacgtcac c                                                         251

<210> SEQ ID NO 16
<211> LENGTH: 143
<212> TYPE: DNA
<213> ORGANISM: Artificial sequence
<220> FEATURE:
<223> OTHER INFORMATION: Synthetic; UN1dGAA-2 polynucleotide

<400> SEQUENCE: 16
aaagtatcaa caaaaaagct tcgtctcctc ttcttcttgt gagagtaaaa aakaaaactc      60
ccaaaaaaaa kaaatcatc aaaaaaacaa atttcaaaaa gagttttgt gtttggggat     120 taaagaakaa aaaaaacaac aaa                                            143

<210> SEQ ID NO 17
<211> LENGTH: 143
<212> TYPE: DNA
<213> ORGANISM: Artificial sequence
<220> FEATURE:
<223> OTHER INFORMATION: Synthetic; UN1dGAA-3 polynucleotide

<400> SEQUENCE: 17
aaagtatcaa caaaaaagct tcgtctcctc ttcttcttgt gagagtaaaa aakaaaactc      60
ccaaaaaaaa kaaatcatc aaaaaaacaa atttcaaaaa gagttttgt gtttggggat     120 taaagaakaa aaaaaacaac gtc                                            143

<210> SEQ ID NO 18
<211> LENGTH: 134
<212> TYPE: DNA
<213> ORGANISM: Artificial sequence
<220> FEATURE:
<223> OTHER INFORMATION: Synthetic; UN1dGAA-4 polynucleotide

<400> SEQUENCE: 18
caagctctag cacgtctcct cttcttcttg tgagagtaaa aaakaaaact cccaaaaaaa      60
akaaaatcat caaaaaaaca aatttcaaaa agagttttg tgtttgggga ttaaagaaka     120
aaaaaaacaa cgcc                                                      134

<210> SEQ ID NO 19
<211> LENGTH: 140
<212> TYPE: DNA
<213> ORGANISM: Artificial sequence
<220> FEATURE:
<223> OTHER INFORMATION: Synthetic; UN1dGAA-5 polynucleotide

<400> SEQUENCE: 19
ggcaagctct agcacgtctc ctcttcttct tgtgagagta aaaakaaaaa ctcccaaaaa      60
aaakaaaatc atcaaaaaaa caatttcaa aaagagttt tgtgtttggg gattaaagaa     120
```
kaaaaaaaac aacctccacc                                              140

<210> SEQ ID NO 20
<211> LENGTH: 130
<212> TYPE: DNA
<213> ORGANISM: Artificial sequence
<220> FEATURE:
<223> OTHER INFORMATION: Synthetic; UN1dGAA-6 polynucleotide

<400> SEQUENCE: 20
caagcgtctc ctcttcttct tgtgagagta aaaakaaaa ctcccaaaaa aaakaaaatc      60
atcaaaaaaa caaatttcaa aaagagttttt tgtgtttggg gattaaagaa kaaaaaaaac   120
aacctccacc                                                         130

<210> SEQ ID NO 21
<211> LENGTH: 178
<212> TYPE: DNA
<213> ORGANISM: Artificial sequence
<220> FEATURE:
<223> OTHER INFORMATION: Synthetic; UN2dGAA-2 polynucleotide

<400> SEQUENCE: 21
cgtctcctct tcttcttgtg agagtaaaaa akaaaactcc caaaaaaaak aaaatcatca     60
aaaaaacaaa tttcaaaaag agttttttgtg tttggggatt aaagaakaaa aaaaacaacc   120
tcgtgcgtgt tgccgattcg cgtacgaata cgccttgtgc tgacacttct gtagcacc     178

<210> SEQ ID NO 22
<211> LENGTH: 238
<212> TYPE: DNA
<213> ORGANISM: Artificial sequence
<220> FEATURE:
<223> OTHER INFORMATION: Synthetic; UN2dGAA-3 polynucleotide

<400> SEQUENCE: 22
caagctctag cacgtctcct cttcttcttg tgagagtaaa aaakaaaact cccaaaaaaa     60
akaaaatcat caaaaaaaca aatttcaaaa agagtttttg tgtttgggga ttaaagaaka   120
aaaaaaacaa caggtgagta agcgcagttg tcgtctcttg cggtgccgtt gctggttctc   180
acacctttta ggtctgttct cgtcttccgt tctgactctc tcttttttcgt tgcaggcc    238

<210> SEQ ID NO 23
<211> LENGTH: 229
<212> TYPE: DNA
<213> ORGANISM: Artificial sequence
<220> FEATURE:
<223> OTHER INFORMATION: Synthetic; UN2dGAA-4 polynucleotide

<400> SEQUENCE: 23
atcaagctct agcacgtctc ctcttcttct tgtgagagta aaaakaaaa ctcccaaaaa     60 aaakaaaatc atcaaaaaaa caaatttcaa aaagagtgag gtaagattat cgatatttaa   120
attatttatt tcttcttttc catttttttg gctaacattt tcctaggttt tattatatct   180
agcaggtacg ttttgtgttt ggggattaaa gaakaaaaaa aacaaaaca              229

<210> SEQ ID NO 24
<211> LENGTH: 188
<212> TYPE: DNA
<213> ORGANISM: Artificial sequence
<220> FEATURE:
<223> OTHER INFORMATION: Synthetic; UN1shuffle polynucleotide

<400> SEQUENCE: 24

```
caagctctag cacgtctcct cttcttcttg tgagagtaaa aaakaaaact cccaaaaaaa      60
akaaaatcat caaaaaaaca aatttcaaaa agagtttttg tgtttgggga ttaaagaaka     120
aaaaaaacaa ggaagaagaa akaagaagaa gaagaagaag aagaagaagg gcggccgccc    180
ccttcacc                                                              188
```

```
<210> SEQ ID NO 25
<211> LENGTH: 173
<212> TYPE: DNA
<213> ORGANISM: Artificial sequence
<220> FEATURE:
<223> OTHER INFORMATION: Synthetic; UN1shuffle-2 polynucleotide

<400> SEQUENCE: 25
caagctctag cacgtctcct cttcttcttg tgagagtaaa aaakaaaact cccaaaaaaa      60
akaaaatcat caaaaaaaca aatttcaaaa agagtttttg tgtttgggga ttaaagaaka     120
aaaaaaacaa ggaagaagaa akaagaagaa gaagaagaag aagaagaagc gcc            173
```

```
<210> SEQ ID NO 26
<211> LENGTH: 154
<212> TYPE: DNA
<213> ORGANISM: Artificial sequence
<220> FEATURE:
<223> OTHER INFORMATION: Synthetic; UN1shuffle-3 polynucleotide

<400> SEQUENCE: 26
gaagctctag cacgtctcct cttcttcttg tgagagtaaa aaakaaaact cccaaaaaaa      60
akaaaatcat caaaaaaaca aatttcaaaa agagtttttg tgtttgggga ttaaagaaka     120
aaaaaaacaa ggaagaagaa gaagaagaag cgcc                                 154
```

```
<210> SEQ ID NO 27
<211> LENGTH: 179
<212> TYPE: DNA
<213> ORGANISM: Artificial sequence
<220> FEATURE:
<223> OTHER INFORMATION: Synthetic; UN1shuffle-4 polynucleotide

<400> SEQUENCE: 27
ggcaagctct agcacgtctc ctcttcttct tgtgagagta aaaaakaaaa ctcccaaaaa      60
aaakaaaatc atcaaaaaaa caaatttcaa aaagagtttt tgtgtttggg gattaaagaa     120
kaaaaaaaac aaggaagaag aaakaagaag aagaagaaga agaagaagaa gcctccacc     179
```

```
<210> SEQ ID NO 28
<211> LENGTH: 160
<212> TYPE: DNA
<213> ORGANISM: Artificial sequence
<220> FEATURE:
<223> OTHER INFORMATION: Synthetic; UN1shuffle-5 polynucleotide

<400> SEQUENCE: 28
ggcaagctct agcacgtctc ctcttcttct tgtgagagta aaaaataaaa ctcccaaaaa      60
aaagaaaatc atcaaaaaaa caaatttcaa aaagagtttt tgtgtttggg gattaaagaa     120
taaaaaaaac aaggaagaag aagaagaaga agcctccacc                           160
```

```
<210> SEQ ID NO 29
<211> LENGTH: 177
<212> TYPE: DNA
<213> ORGANISM: Artificial sequence
<220> FEATURE:
```

<223> OTHER INFORMATION: Synthetic; UN1shuffle-6 polynucleotide

<400> SEQUENCE: 29

```
caagctctag cacgtctcct cttcttcttg tgagagtaaa aaakaaaact cccaaaaaaa      60
akaaaatcat caaaaaaaca aatttcaaaa agagtttttg tgtttgggga ttaaagaaka     120
aaaaaaacaa ggaagaagaa akaagaagaa gaagaagaag aagaagaagc ctccacc       177
```

<210> SEQ ID NO 30
<211> LENGTH: 277
<212> TYPE: DNA
<213> ORGANISM: Artificial sequence
<220> FEATURE:
<223> OTHER INFORMATION: Synthetic; UN2shuffle-1 polynucleotide

<400> SEQUENCE: 30

```
caagctctag cacgtctcct cttcttcttg tgagagtaaa aaakaaaact cccaaaaaaa      60
akaaaatcat caaaaaaaca aatttcaaaa agagtttttg tgtttgggga ttaaagaaka     120
aaaaaaacaa ggaagaagaa akaagaagaa gaagaagaag aagaagaagc aggtgagtaa    180
gcgcagttgt cgtctcttgc ggtgccgttg ctggttctca cccttttag gtctgttctc     240
gtcttccgtt ctgactctct cttttttcgtt gcaggcc                            277
```

<210> SEQ ID NO 31
<211> LENGTH: 267
<212> TYPE: DNA
<213> ORGANISM: Artificial sequence
<220> FEATURE:
<223> OTHER INFORMATION: Synthetic; UN2shuffle-2 polynucleotide

<400> SEQUENCE: 31

```
atcaagctct agcacgtctc ctcttcttct tgtgagagta aaaakaaaa ctcccaaaaa       60
aaakaaaatc atcaaaaaaa caaatttcaa aaagagtgag gtaagattat cgatatttaa    120
attatttatt tcttcttttc cattttttttg gctaacattt tcctaggttt tattatatct   180
agcaggtacg ttttgtgttt ggggattaaa gaakaaaaaa aacaaggaag aagaaakaag    240
aagaagaaga agaagaagaa gaaaaca                                        267
```

<210> SEQ ID NO 32
<211> LENGTH: 264
<212> TYPE: DNA
<213> ORGANISM: Artificial sequence
<220> FEATURE:
<223> OTHER INFORMATION: Synthetic; CAA1 polynucleotide

<400> SEQUENCE: 32

```
caagctctac caccaagaac aaacaacaac aacatatata aaacaacaac caccatctcc      60
tcttcttctt gtcaactcca aaatcaaact cccaaaaaaa agcaaatcat caaaagtgag    120
gtaagattat cgatatttaa attatttatt tcttcttttc cattttttttg gctaacattt   180
tcctaggttt tattatatct agcaggtacg aaatttcaaa caacaacaac aaacaacaaa   240
caacattaac atcatatcaa aacc                                           264
```

<210> SEQ ID NO 33
<211> LENGTH: 188
<212> TYPE: DNA
<213> ORGANISM: Artificial sequence
<220> FEATURE:
<223> OTHER INFORMATION: Synthetic; CAA2 polynucleotide

<400> SEQUENCE: 33

```
caacctctac caccaacaac aaacaacaac aacaacaaca acaacaacaa ccctctccac    60
atctccctct cagagtaaaa aacaaaactc ccaaaaaaaa gaaaatcatc aaaaaaacaa   120
atttcaaaaa gacttcttct cattccttat taaagaacaa aaaaaacaag gcggccgccc   180
ccttcacc                                                            188
```

<210> SEQ ID NO 34
<211> LENGTH: 207
<212> TYPE: DNA
<213> ORGANISM: Artificial sequence
<220> FEATURE:
<223> OTHER INFORMATION: Synthetic; CAA3 polynucleotide

<400> SEQUENCE: 34

```
gtatttttac aacaattacc aacaacaaca aacaacaaac aacattacaa ttactattta    60
caattacaag cgtctcctct tcttcttgtg agagtaaaaa ataaaactcc caaaaaaaag   120
aaaatcatca aaaaaacaaa tttcaaaaag agttttgtg tttggggatt aaagaataaa   180
aaaaacaagg cggccgcccc cttcacc                                       207
```

<210> SEQ ID NO 35
<211> LENGTH: 188
<212> TYPE: DNA
<213> ORGANISM: Artificial sequence
<220> FEATURE:
<223> OTHER INFORMATION: Synthetic; CAA4 polynucleotide

<400> SEQUENCE: 35

```
caagctctac caccaagaac aaacaacaac aacatatata aaacaacaac caccatctcc    60
tcttcttctt gtcaactcca aaatcaaact cccaaaaaaa agcaaatcat caaaaccaca   120
aatttcaaac aacaacaaca aacaacaaac aacattaaca tcatatcaag gcggccgccc   180
ccttcacc                                                            188
```

<210> SEQ ID NO 36
<211> LENGTH: 175
<212> TYPE: DNA
<213> ORGANISM: Artificial sequence
<220> FEATURE:
<223> OTHER INFORMATION: Synthetic; CAA5 polynucleotide

<400> SEQUENCE: 36

```
caacctctac caccaacaac aaacaacaac aacaacaaca acaacaacaa ccctctccac    60
atctccctct cagagtaaaa aacaaaattg acaaaaaaaa gattttataa taaaaacaaa   120
tttcaaaaag aattcaactc attcaatatt acaacaagaa caaggaggt cacat         175
```

<210> SEQ ID NO 37
<211> LENGTH: 177
<212> TYPE: DNA
<213> ORGANISM: Artificial sequence
<220> FEATURE:
<223> OTHER INFORMATION: Synthetic; CAA6 polynucleotide

<400> SEQUENCE: 37

```
caagctctac caccaagaac aaacaacaac aacatatata aaacaacaac caccatctcc    60
tcttcttctt gtcaactcca aaatcaaact cccaaaaaaa agcaaatcat caaaaccaca   120
aatttcaaac aacaacaaca aacaacaaac aacattaaca tcatatcaac ctccacc      177
```

<210> SEQ ID NO 38

```
<211> LENGTH: 175
<212> TYPE: DNA
<213> ORGANISM: Artificial sequence
<220> FEATURE:
<223> OTHER INFORMATION: Synthetic; TATA1 polynucleotide

<400> SEQUENCE: 38
caagctctag caggaagaag aaataagaag aagaagaaga agaagaagaa gcgtctcctc    60
ttcttcttga cagagtaaaa aataacttttt ataataaaga aaatcatcaa aaaaacaaat   120
ttcaaaaaga gttttttgtgt ttggggatta aagaataaaa aaaaggaggt cacat        175

<210> SEQ ID NO 39
<211> LENGTH: 177
<212> TYPE: DNA
<213> ORGANISM: Artificial sequence
<220> FEATURE:
<223> OTHER INFORMATION: Synthetic; TATA2 polynucleotide

<400> SEQUENCE: 39
caagctctag caggaagaag aaataagaag aagtatataa aagaagaaga agcgtctcct    60
cttcttcttg tgaagtaaaa aataaaactc ccaaaaaaaa gaaaatcatc aaaaaaacaa   120
atttcaaaaa gagttttttgt gtttggggat taaagaataa aaaaaacaac ctccacc      177

<210> SEQ ID NO 40
<211> LENGTH: 37
<212> TYPE: DNA
<213> ORGANISM: Artificial sequence
<220> FEATURE:
<223> OTHER INFORMATION: Synthetic; GAA1 repeat polynucleotide

<400> SEQUENCE: 40
gaagaagaaa kaagaagaag aagaagaaga agaagaa                             37

<210> SEQ ID NO 41
<211> LENGTH: 18
<212> TYPE: DNA
<213> ORGANISM: Artificial sequence
<220> FEATURE:
<223> OTHER INFORMATION: Synthetic; GAA2 repeat polynucleotide

<400> SEQUENCE: 41
gaagaagaag aagaagaa                                                  18

<210> SEQ ID NO 42
<211> LENGTH: 80
<212> TYPE: DNA
<213> ORGANISM: Artificial sequence
<220> FEATURE:
<223> OTHER INFORMATION: Synthetic; primer PN012

<400> SEQUENCE: 42
cgagggccct aatacgactc actataggaa gctctagcag gaagaagaaa taagaagaag    60
aagaagaaga agaagaagcg                                                80

<210> SEQ ID NO 43
<211> LENGTH: 28
<212> TYPE: DNA
<213> ORGANISM: Artificial sequence
<220> FEATURE:
<223> OTHER INFORMATION: Synthetic; Primer PN008

<400> SEQUENCE: 43
tcaggctgcg caactgttgg gaagggcg                                       28
```

<210> SEQ ID NO 44
<211> LENGTH: 70
<212> TYPE: DNA
<213> ORGANISM: Artificial sequence
<220> FEATURE:
<223> OTHER INFORMATION: Synthetic; Primer PN014

<400> SEQUENCE: 44
tcgagggccc taatacgact cactataggc gtctcctctt cttcttgtga gagtaaaaaa    60
taaaactccc                                                            70

<210> SEQ ID NO 45
<211> LENGTH: 48
<212> TYPE: DNA
<213> ORGANISM: Artificial sequence
<220> FEATURE:
<223> OTHER INFORMATION: Synthetic; polynucleotide Reference Example 1

<400> SEQUENCE: 45
ggaatacaag cttatgcatg cggccgcatc tagagggccc ggatccaa                   48

<210> SEQ ID NO 46
<211> LENGTH: 173
<212> TYPE: DNA
<213> ORGANISM: Artificial sequence
<220> FEATURE:
<223> OTHER INFORMATION: Synthetic; UN1 polynucleotide Example 1

<400> SEQUENCE: 46
ggaagctcta gcaggaagaa gaaataagaa gaagaagaag aagaagaaga agcgtctcct    60
cttcttcttg tgagagtaaa aaataaaact cccaaaaaaa agaaaatcat caaaaaaaca   120
aatttcaaaa agagttttg tgtttgggga ttaaagaata aaaaaacaac gtc            173

<210> SEQ ID NO 47
<211> LENGTH: 43
<212> TYPE: DNA
<213> ORGANISM: Artificial sequence
<220> FEATURE:
<223> OTHER INFORMATION: Synthetic; GAA polynucleotide Example 1

<400> SEQUENCE: 47
ggaagaagaa ataagaagaa gaagaagaag aagaagaagc gcc                       43

<210> SEQ ID NO 48
<211> LENGTH: 123
<212> TYPE: DNA
<213> ORGANISM: Artificial sequence
<220> FEATURE:
<223> OTHER INFORMATION: Synthetic; dGAA polynucleotide Example 1

<400> SEQUENCE: 48
ggcgtctcct cttcttcttg tgagagtaaa aaataaaact cccaaaaaaa agaaaatcat    60
caaaaaaaca aatttcaaaa agagttttg tgtttgggga ttaaagaata aaaaaacaac   120
gtc                                                                  123

<210> SEQ ID NO 49
<211> LENGTH: 189
<212> TYPE: DNA
<213> ORGANISM: Artificial sequence
<220> FEATURE:
<223> OTHER INFORMATION: Synthetic; UN1 polynucleotide Example 2

<400> SEQUENCE: 49

```
agatcactag aagcttcaag ctctagcagg aagaagaaat aagaagaaga agaagaagaa      60
gaagaagcgt ctcctcttct tcttgtgaga gtaaaaaata aaactcccaa aaaaaagaaa     120
atcatcaaaa aaacaaattt caaaagagt ttttgtgttt ggggattaaa gataaaaaaa     180
aacaacgcc                                                             189
```

<210> SEQ ID NO 50
<211> LENGTH: 293
<212> TYPE: DNA
<213> ORGANISM: Artificial sequence
<220> FEATURE:
<223> OTHER INFORMATION: Synthetic; UN2a polynucleotide Example 2

<400> SEQUENCE: 50

```
agatcactag aagcttcaag ctctagcagg aagaagaaat aagaagaaga agaagaagaa      60
gaagaagcgt ctcctcttct tcttgtgaga gtaaaaaata aaactcccaa aaaaaagaaa     120
atcatcaaaa aaacaaattt caaaagagt ttttgtgttt ggggattaaa gataaaaaaa     180
aacaacaggt gagtaagcgc agttgtcgtc tcttgcggtg ccgttgctgg ttctcacacc    240
ttttaggtct gttctcgtct tccgttctga ctctctcttt ttcgttgcag gcc            293
```

<210> SEQ ID NO 51
<211> LENGTH: 293
<212> TYPE: DNA
<213> ORGANISM: Artificial Sequence
<220> FEATURE:
<223> OTHER INFORMATION: Synthetic; UN2b polynucleotide Example 2

<400> SEQUENCE: 51

```
agatcactag aagcttcaag ctctagcagg aagaagaaag aagaagaaga agaagaagaa      60
gaagaagcgt ctcctcttct tcttgtgaga gtaaaaaaga aaactcccaa aaaaaagaaa    120
atcatcaaaa aaacaaattt caaaagagt ttttgtgttt ggggattaaa gagaaaaaa     180
aacaacaggt gagtaagcgc agttgtcgtc tcttgcggtg ccgttgctgg ttctcacacc    240
ttttaggtct gttctcgtct tccgttctga ctctctcttt ttcgttgcag gcc            293
```

<210> SEQ ID NO 52
<211> LENGTH: 177
<212> TYPE: DNA
<213> ORGANISM: Artificial sequence
<220> FEATURE:
<223> OTHER INFORMATION: Synthetic; UN1-153 polynucleotide

<400> SEQUENCE: 52

```
caagctctag caggaagaag aaataagaag aagaagaaga agaagaagaa gcgtctcctc      60
ttcttcttgt gagagtaaaa aataaaactc ccaaaaaaaa gaaaatcatc aaaaaaacaa    120
atttcaaaaa gagttttgt gtttggggat taagaataa aaaaacaac ctccacc          177
```

<210> SEQ ID NO 53
<211> LENGTH: 178
<212> TYPE: DNA
<213> ORGANISM: Artificial sequence
<220> FEATURE:
<223> OTHER INFORMATION: Synthetic; UN2-dGAA-181 polynucleotide

<400> SEQUENCE: 53

```
cgtctcctct tcttcttgtg agagtaaaaa ataaaactcc caaaaaaaag aaaatcatca      60
aaaaaacaaa tttcaaaaag agttttgtg tttggggatt aagaataaa aaaacaacc      120
```
tcgtgcgtgt tgccgattcg cgtacgaata cgccttgtgc tgacacttct gtagcacc        178

<210> SEQ ID NO 54
<211> LENGTH: 178
<212> TYPE: DNA
<213> ORGANISM: Artificial sequence
<220> FEATURE:
<223> OTHER INFORMATION: Synthetic; UN2-dGAA-cc-182 polynucleotide

<400> SEQUENCE: 54
cgtctcctct tcttcttgtg agagtaaaaa agaaaactcc caaaaaaaag aaaatcatca        60
aaaaaacaaa tttcaaaaag agttttttgtg tttggggatt aaagaagaaa aaaaacaacc      120
tcgtgcgtgt tgccgattcg cgtacgaata cgccttgtgc tgacacttct gtagcacc        178

<210> SEQ ID NO 55
<211> LENGTH: 188
<212> TYPE: DNA
<213> ORGANISM: Artificial sequence
<220> FEATURE:
<223> OTHER INFORMATION: Synthetic; UN1-218 polynucleotide

<400> SEQUENCE: 55
caagctctag caggaagaag aaataagaag aagaagaaga agaagaagaa gcgtctcctc        60
ttcttcttgt gagagtaaaa aataaaactc ccaaaaaaaa gaaaatcatc aaaaaaacaa      120
atttcaaaaa gagttttttgt gtttggggat taaagaataa aaaaaacaag gcggccgccc      180
ccttcacc                                                                188

<210> SEQ ID NO 56
<211> LENGTH: 188
<212> TYPE: DNA
<213> ORGANISM: Artificial sequence
<220> FEATURE:
<223> OTHER INFORMATION: Synthetic; UN1-Min-286 polynucleotide

<400> SEQUENCE: 56
caacctctac caccaacaac aaacaacaac aacaacaaca caacaacaa ccctctccac        60 atctccctct cagagtaaaa aacaaaactc ccaaaaaaaa gaaaatcatc aaaaaaacaa      120
atttcaaaaa gacttcttct cattccttat taaagaacaa aaaaaacaag gcggccgccc      180
ccttcacc                                                                188

<210> SEQ ID NO 57
<211> LENGTH: 188
<212> TYPE: DNA
<213> ORGANISM: Artificial sequence
<220> FEATURE:
<223> OTHER INFORMATION: Synthetic; UN1-G11/3-287 polynucleotide

<400> SEQUENCE: 57
caagctctag cacgtctcct cttcttcttg tgagagtaaa aataaaact cccaaaaaaa        60 agaaaatcat caaaaaaaca aatttcaaaa agagttttttg tgtttgggga ttaaagaata    120
aaaaaaacaa ggaagaagaa ataagaagaa gaagaagaag aagaagagg gcggccgccc      180 ccttcacc                                                                188

<210> SEQ ID NO 58
<211> LENGTH: 207
<212> TYPE: DNA
<213> ORGANISM: Artificial sequence
<220> FEATURE:

<223> OTHER INFORMATION: Synthetic; UN1-CAA-288 polynucleotide

<400> SEQUENCE: 58

```
gtattttac  aacaattacc  aacaacaaca  aacaacaaac  aacattacaa  ttactattta    60
caattacaag  cgtctcctct  tcttcttgtg  agagtaaaaa  ataaaactcc  caaaaaaag   120
aaaatcatca  aaaaacaaa   tttcaaaaag  agttttgtg   tttggggatt  aaagaataaa   180
aaaaacaagg  cggccgcccc  cttcacc                                          207
```

<210> SEQ ID NO 59
<211> LENGTH: 188
<212> TYPE: DNA
<213> ORGANISM: Artificial sequence
<220> FEATURE:
<223> OTHER INFORMATION: Synthetic; UN1-Min/TATA/CAA-290 polynucleotide

<400> SEQUENCE: 59

```
caagctctac  caccaagaac  aaacaacaac  aacatatata  aaacaacaac  caccatctcc    60
tcttcttctt  gtcaactcca  aaatcaaact  cccaaaaaaa  agcaaatcat  caaaaccaca   120
aatttcaaac  aacaacaaca  aacaacaaac  aacattaaca  tcatatcaag  gcggccgccc   180
ccttcacc                                                                 188
```

<210> SEQ ID NO 60
<211> LENGTH: 22
<212> TYPE: DNA
<213> ORGANISM: Artificial sequence
<220> FEATURE:
<223> OTHER INFORMATION: Synthetic; Primer PN.272

<400> SEQUENCE: 60

```
ctcgtcttca  ccggtcgcgt  tc                                                22
```

<210> SEQ ID NO 61
<211> LENGTH: 59
<212> TYPE: DNA
<213> ORGANISM: Artificial sequence
<220> FEATURE:
<223> OTHER INFORMATION: Synthetic; Primer PN.273

<400> SEQUENCE: 61

```
cgtcgcagct  aagcttttt  gttgatactt  ttattacatt  tgaataagaa  gtaatacaa     59
```

<210> SEQ ID NO 62
<211> LENGTH: 35
<212> TYPE: DNA
<213> ORGANISM: Artificial sequence
<220> FEATURE:
<223> OTHER INFORMATION: Synthetic; Primer PN.307

<400> SEQUENCE: 62

```
gatataatac  agctgacgga  ttagaagccg  ccgag                                 35
```

<210> SEQ ID NO 63
<211> LENGTH: 40
<212> TYPE: DNA
<213> ORGANISM: Artificial sequence
<220> FEATURE:
<223> OTHER INFORMATION: Synthetic; Primer PN.308

<400> SEQUENCE: 63

```
cttacttgag  atgcatgcaa  attaaagcct  tcgagcgtcc                             40
```

```
<210> SEQ ID NO 64
<211> LENGTH: 40
<212> TYPE: DNA
<213> ORGANISM: Artificial sequence
<220> FEATURE:
<223> OTHER INFORMATION: Synthetic; Primer PN.345

<400> SEQUENCE: 64
gcagcgtcag aagcttcgtc tcctcttctt cttgtgagag                           40

<210> SEQ ID NO 65
<211> LENGTH: 38
<212> TYPE: DNA
<213> ORGANISM: Artificial sequence
<220> FEATURE:
<223> OTHER INFORMATION: Synthetic; Primer PN.346

<400> SEQUENCE: 65
cttacttgag tctagattat gaattctcag ccctcttc                             38

<210> SEQ ID NO 66
<211> LENGTH: 80
<212> TYPE: DNA
<213> ORGANISM: Artificial sequence
<220> FEATURE:
<223> OTHER INFORMATION: Synthetic; Primer PN.316

<400> SEQUENCE: 66
cagctgcata caatcattta ttaagtagtt gaagcatgta tgaactataa aagtgttact     60
aggcgtatca cgaggccagc                                                 80

<210> SEQ ID NO 67
<211> LENGTH: 321
<212> TYPE: DNA
<213> ORGANISM: Artificial sequence
<220> FEATURE:
<223> OTHER INFORMATION: Synthetic; Pgal1-mod polynucleotide Example 5

<400> SEQUENCE: 67
accggtcgcg ttcctgaaac gcagatgtgc ctcgcgccgc actgctccga acaataaaga     60
ttctacaata ctagctttta tggttatgaa gaggaaaaat tggcagtaac ctggccccac    120
aaaccttcaa atgaacgaat caaattaaca accataggat gataatgcga ttagtttttt    180
agccttattt ctggggtaat taatcagcga agcgatgatt tttgatctat taacagatat    240
ataaatgcaa aaactgcata accactttaa ctaatacttt caacattttc ggtttgtatt    300
acttcttatt caaatgtaat a                                              321

<210> SEQ ID NO 68
<211> LENGTH: 65
<212> TYPE: DNA
<213> ORGANISM: Artificial sequence
<220> FEATURE:
<223> OTHER INFORMATION: Synthetic; 5'UTR polynucleotide Example 5

<400> SEQUENCE: 68
aaagtatcaa caaaaaagct tgttaatata cctctatact ttaacgtcaa ggagaaaaaa     60
ctata                                                                 65

<210> SEQ ID NO 69
<211> LENGTH: 306
<212> TYPE: DNA
<213> ORGANISM: homo sapiens
```

<400> SEQUENCE: 69

```
atgatgcttt tgcaagcctt ccttttcctt ttggctggtt ttgcagctaa gatatctgca    60
gaaggtgcag ttttgccaag gagtgctaaa gaacttagat gtcagtgcat aaagacatac   120
tccaaacctt tccaccccaa atttatcaaa gaactgagag tgattgagag tggaccacac   180
tgcgccaaca cagaaattat tgtaaaactt tctgatggaa gagagctctg tctggacccc   240
aaggaaaact gggtgcagag ggttgtggag aagttttga agagggctga gaattcataa    300
tctaga                                                              306
```

<210> SEQ ID NO 70
<211> LENGTH: 186
<212> TYPE: DNA
<213> ORGANISM: Artificial sequence
<220> FEATURE:
<223> OTHER INFORMATION: Synthetic; UN1 polynucleotide Example 5

<400> SEQUENCE: 70

```
aaagtatcaa caaaaaagct tagcaggaag aagaaataag aagaagaaga agaagaagaa    60
gaagcgtctc ctcttcttct tgtgagagta aaaaataaaa ctcccaaaaa aagaaaatc    120 atcaaaaaaa caaatttcaa aaagagtttt tgtgtttggg gattaaagaa taaaaaaac    180 aacaaa                                                              186
```

<210> SEQ ID NO 71
<211> LENGTH: 143
<212> TYPE: DNA
<213> ORGANISM: Artificial sequence
<220> FEATURE:
<223> OTHER INFORMATION: Synthetic; UN1-dGAA polynucleotide Example 5

<400> SEQUENCE: 71

```
aaagtatcaa caaaaaagct tcgtctcctc ttcttcttgt gagagtaaaa aataaaactc    60
ccaaaaaaaa gaaaatcatc aaaaaaacaa atttcaaaaa gagttttgt gtttggggat   120 taaagaataa aaaaacaac aaa                                            143
```

<210> SEQ ID NO 72
<211> LENGTH: 143
<212> TYPE: DNA
<213> ORGANISM: Artificial sequence
<220> FEATURE:
<223> OTHER INFORMATION: Synthetic; UN1-dGAAcc polynucleotide Example 5

<400> SEQUENCE: 72

```
aaagtatcaa caaaaaagct tcgtctcctc ttcttcttgt gagagtaaaa aagaaaactc    60
ccaaaaaaaa gaaaatcatc aaaaaaacaa atttcaaaaa gagttttgt gtttggggat   120 taaagaagaa aaaaacaac aaa                                            143
```

<210> SEQ ID NO 73
<211> LENGTH: 257
<212> TYPE: DNA
<213> ORGANISM: Artificial sequence
<220> FEATURE:
<223> OTHER INFORMATION: Synthetic; UN2-dGAAcc polynucleotide

<400> SEQUENCE: 73

```
aaagtatcaa caaaaaagct tcgtctcctc ttcttcttgt gagagtaaaa aagaaaactc    60
ccaaaaaaaa gaaaatcatc aaaaaaacaa atttcaaaaa gagttttgt gtttgtaagt   120 caggactcta gctttctact gtagtatcct ctaaaggact gctgttctgt gcacccctt    180
```

```
cctttgttta tcatagcgca cgacaagagt actaactaat taacttaggg ggattaaaga    240
agaaaaaaaa caacaaa                                                  257
```

<210> SEQ ID NO 74
<211> LENGTH: 173
<212> TYPE: DNA
<213> ORGANISM: Artificial sequence
<220> FEATURE:
<223> OTHER INFORMATION: Synthetic; UN1-228 polynucleotide

<400> SEQUENCE: 74

```
caagctctag caggaagaag aaataagaag aagaagaaga agaagaagaa gcgtctcctc    60
ttcttcttgt gagagtaaaa aataaaactc ccaaaaaaaa gaaaatcatc aaaaaaacaa    120
atttcaaaaa gagttttgt gtttggggat taaagaataa aaaaaacaac ctc            173
```

<210> SEQ ID NO 75
<211> LENGTH: 173
<212> TYPE: DNA
<213> ORGANISM: Artificial sequence
<220> FEATURE:
<223> OTHER INFORMATION: Synthetic; R3-230 polynucleotide

<400> SEQUENCE: 75

```
caagctctag cacgtctcct cttcttcttg tgagagtaaa aataaaaact cccaaaaaaa    60
agaaaatcat caaaaaaaca aatttcaaaa agagttttg tgtttgggga ttaaagaata    120
aaaaaaacaa ggaagaagaa ataagaagaa gaagaagaag aagaagaagc ctc            173
```

<210> SEQ ID NO 76
<211> LENGTH: 214
<212> TYPE: DNA
<213> ORGANISM: homo sapiens

<400> SEQUENCE: 76

```
atgctgctgc tgctgctgct gctgggcctg aggctacagc tctccctggg catcatccca    60
gttgaggagg agaacccgga cttctggaac cgcgaggcag ccgaggccct gggtgccgcc    120
aagaagctgc agcctgcaca gacagccgcc aagaacctca tcatcttcct gggcgatggg    180 atggggtgt ctacggtgac agctgccagg atcc                                 214
```

<210> SEQ ID NO 77
<211> LENGTH: 471
<212> TYPE: DNA
<213> ORGANISM: homo sapiens

<400> SEQUENCE: 77

```
atgggtctca cctcccaact gcttcccct ctgttcttcc tgctagcatg tgccggcaac    60
tttgtccacg gacacaagtg cgatatcacc ttacaggaga tcatcaaaac tttgaacagc    120
ctcacagagc agaagactct gtgcaccgag ttgaccgtaa cagacatctt tgctgcctcc    180
aagaacacaa ctgagaagga aaccttctgc agggctgcga ctgtgctccg gcagttctac    240
agccaccatg agaaggacac tcgctgcctg ggtgcgactg cacagcagtt ccacaggcac    300
aagcagctga tccgattcct gaaacggctc gacaggaacc tctggggcct ggcgggcttg    360
aattcctgtc ctgtgaagga agccaaccag agtacgttgg aaaacttctt ggaaaggcta    420
aagacgatca tgagagagaa atattcaaag tgttcgagct gataattcga a             471
```

<210> SEQ ID NO 78

<211> LENGTH: 173
<212> TYPE: DNA
<213> ORGANISM: Nicotiana tabacum

<400> SEQUENCE: 78

```
caagctctag caggaagaag aaataagaag aagaagaaga agaagaagaa gcgtctcctc    60
ttcttcttgt gagagtaaaa aataaaactc ccaaaaaaaa gaaaatcatc aaaaaaacaa   120
atttcaaaaa gagttttgt gtttggggat taaagaataa aaaaaacaac gcc           173
```

<210> SEQ ID NO 79
<211> LENGTH: 277
<212> TYPE: DNA
<213> ORGANISM: Artificial sequence
<220> FEATURE:
<223> OTHER INFORMATION: Synthetic; UN2-M25 polynucleotide Example 7

<400> SEQUENCE: 79

```
caagctctag caggaagaag aaataagaag aagaagaaga agaagaagaa gcgtctcctc    60
ttcttcttgt gagagtaaaa aataaaactc ccaaaaaaaa gaaaatcatc aaaaaaacaa   120
atttcaaaaa gagttttgt gtttggggat taaagaataa aaaaaacaac aggtgagtaa   180
gcgcagttgt cgtctcttgc ggtgccgttg ctggttctca cccttttag gtctgttctc   240
gtcttccgtt ctgactctct cttttcgtt gcaggcc                             277
```

<210> SEQ ID NO 80
<211> LENGTH: 1231
<212> TYPE: DNA
<213> ORGANISM: Artificial sequence
<220> FEATURE:
<223> OTHER INFORMATION: Synthetic; fUN1 polynucleotide Example 8

<400> SEQUENCE: 80

```
ggccgcaata aaatatcttt attttcatta catctgtgtg ttggtttttt gtgtgaatcg    60
atagtactaa catacgctct ccatcaaaac aaaacgaaac aaaacaaact agcaaaatag   120
gctgtcccca gtgcaagtgc aggtgccaga acatttctct atcgataggt accgagctcg   180
ttgacattga ttattgacta gttattaata gtaatcaatt acggggtcat tagttcatag   240
cccatatatg gagttccgcg ttacataact tacggtaaat ggcccgcctg gctgaccgcc   300
caacgacccc cgcccattga cgtcaataat gacgtatgtt cccatagtaa cgccaatagg   360
gactttccat tgacgtcaat gggtggacta tttacggtaa actgcccact tggcagtaca   420
tcaagtgtat catatgccaa gtacgccccc tattgacgtc aatgacggta atggcccgc   480
ctggcattat gcccagtaca tgaccttatg gactttcct acttggcagt acatctacgt   540
attagtcatc gctattacca tggtgatgcg gttttggcag tacatcaatg ggcgtggata   600
gcggtttgac tcacggggat ttccaagtct ccaccccatt gacgtcaatg ggagtttgtt   660
ttggcaccaa aatcaacggg actttccaaa atgtcgtaac aactccgccc cattgacgca   720
aatgggcggt aggcgtgtac ggtgggaggt ctatataagc agagctggtt tagtgaaccg   780
tggatcccaa gctctagcag gaagaagaaa taagaagaag aagaagaaga agaagaagcg   840
tctcctcttc ttcttgtgag agtaaaaaat aaaactccca aaaaaagaa aatcatcaaa   900
aaacaaattt caaaaagag ttttgtgtt tggggattaa agaataaaaa aaacaacgtc   960
cctctagagt cggggcggcc ggccgcttcg agcagacatg ataagataca ttgatgagtt  1020
tggacaaacc acaactagaa tgcagtgaaa aaaatgcttt atttgtgaaa tttgtgatgc  1080
tattgcttta tttgtaacca ttataagctg caataaacaa gttaacaaca acaattgcat  1140
```

```
tcattttatg tttcaggttc aggggggaggt gtgggaggtt ttttaaagca agtaaaacct    1200
ctacaaatgt ggtaaaatcg ataaggatcc g                                   1231
```